(12) United States Patent
Mach et al.

(10) Patent No.: US 11,964,938 B2
(45) Date of Patent: Apr. 23, 2024

(54) 3-PHENYL-4-HEXYNOIC ACID DERIVATIVES AS GPR40 AGONISTS

(71) Applicant: CELON PHARMA S.A., Kielpin/Lomianki (PL)

(72) Inventors: Mateusz Mach, Warsaw (PL); Radoslaw Dzida, Czechowice-Dziedzice (PL); Damian Smuga, Nowy Dwor Mazowiecki (PL); Filip Stelmach, Lomianki (PL); Mikolaj Matloka, Leszno (PL); Katarzyna Bazydlo, Warsaw (PL); Krzysztof Dubiel, Babice Nowe (PL); Maciej Wieczorek, Kielpin/Lomianki (PL); Jerzy Pieczykolan, Warsaw (PL)

(73) Assignee: CELON PHARMA S.A., Kielpin/Lomianki (PL)

( * ) Notice: Subject to any disclaimer, the term of this patent is extended or adjusted under 35 U.S.C. 154(b) by 809 days.

(21) Appl. No.: 16/960,700

(22) PCT Filed: Jan. 7, 2019

(86) PCT No.: PCT/EP2019/050194
§ 371 (c)(1),
(2) Date: Jul. 8, 2020

(87) PCT Pub. No.: WO2019/134984
PCT Pub. Date: Jul. 11, 2019

(65) Prior Publication Data
US 2020/0399198 A1  Dec. 24, 2020

(30) Foreign Application Priority Data

Jan. 8, 2018 (PL) .......................................... 424227
May 18, 2018 (PL) .......................................... 425625

(51) Int. Cl.
*C07C 59/68* (2006.01)
*A61P 3/10* (2006.01)

(52) U.S. Cl.
CPC ................ *C07C 59/68* (2013.01); *A61P 3/10* (2018.01); *C07B 2200/07* (2013.01)

(58) Field of Classification Search
CPC ......... C07C 59/68; A61P 3/10; C07B 2200/07
See application file for complete search history.

(56) References Cited

U.S. PATENT DOCUMENTS

2007/0066647 A1  3/2007  Akerman et al.
2012/0004166 A1  1/2012  Keil et al.

FOREIGN PATENT DOCUMENTS

| EP | 3 207 928 A2 | 8/2017 | |
| EP | 3207928 A2 * | 8/2017 | ........... A61K 31/192 |
| WO | 2005/086661 A2 | 9/2005 | |
| WO | WO-2005086661 A2 * | 9/2005 | ........... C07D 277/24 |

OTHER PUBLICATIONS

PubChem SID 344303732 <https://pubchem.ncbi.nlm.nih.gov/substance/344303732> Oct. 7, 2017. Accessed Jul. 19, 2023. (Year: 2017).*
PubChem CID 130351151 <https://pubchem.ncbi.nlm.nih.gov/compound/130351151> ) Oct. 7, 2017. Accessed Jul. 19, 2023. (Year: 2017).*
International Search Report issued by the International Searching Authority (ISA/O.E.P.M.) dated Mar. 4, 2019 in connection with International Application No. PCT/EP2019/050194.
Mach M. et al., Discovery and development of CPL207280 as new GPR40/FFA1 agonist. European Journal of Medicinal Chemistry vol. 226, Dec. 15, 2021, 113810.
Bazydlo-Guzenda et al., CPL207280—a novel GPR40/FFA1—specific agonist shows a favorable safety profile and exerts antidiabetic effects in type 2 diabetic animals. Molecular Pharmacology Oct. 2021, 100 (4) 335-347.
Bazydlo-Guzenda et al., Evaluation of the hepatotoxicity of the novel GPR40 (FFAR1) agonist CPL207280 in the rat and monkey. PLOS One Sep. 23, 2021;16(9):e0257477.
Juszczyk E. et al., Development and Bio-Predictive Evaluation of Biopharmaceutical Properties of Sustained-Release Tablets with a Novel GPR40 Agonist for a First-in-Human Clinical Trial. Pharmaceutics 2021, 13(6), 804.
Pawel Buda et al., Novel GPR40 agonist CPL207-280CA independently improves glycaemia and mitigates neuropathic pain in diabetic rodents; Oct. 3, 2018, European Association for the Study of Diabetes, Session: Tackling glucose and fat with novel agents.

(Continued)

*Primary Examiner* — Michael Barker
*Assistant Examiner* — Jed A Kucharczk
(74) *Attorney, Agent, or Firm* — Gary J. Gershik

(57) ABSTRACT

A compound of the formula (I) wherein R represents a straight or branched, primary or secondary acyclic hydrocarbyl C3-C15 group, which can be saturated or unsaturated, or a straight or branched, primary or secondary acyclic hydrocarbyl C3-C15 group, which can be saturated or unsaturated and wherein one or more of hydrogen atoms is replaced with fluorine atom; X represents hydrogen atom or halogen atom, and * denotes chiral center, and salts thereof. The compound is useful for the treatment of diseases mediated by GPR40, in particular type II diabetes. (I)

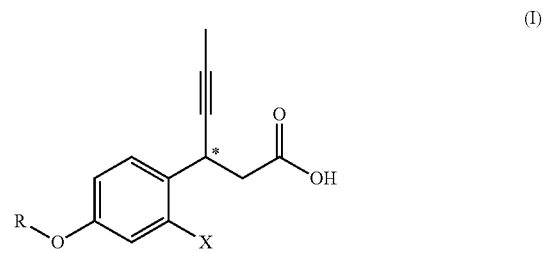

23 Claims, No Drawings

(56) References Cited

OTHER PUBLICATIONS

Katarzyna Bazydlo-Guzenda et al., Safety and pharmacokinetic study of CPL207280, a novel GPR40 receptor agonist after a multiple-dose in healthly volunteers; Oct. 1, 2021, European Association for the Study of Diabetes, Session: OP 38 Novel agents.
T. Jaworski et al., Preclinical efficacy of the novel GPR40 agonist CPL207-280 in neuropathy; Oct. 5, 2023.

* cited by examiner

3-PHENYL-4-HEXYNOIC ACID DERIVATIVES AS GPR40 AGONISTS

RELATED APPLICATIONS

This application is a § 371 national stage of PCT International Application No. PCT/EP2019/050194, filed Jan. 7, 2019, designating the United States and claiming priority of Polish Application Nos. PL425625, filed May 18, 2018 and PL424227, filed Jan. 8, 2018, the contents of each of which are hereby incorporated by reference into this application.

FIELD OF THE INVENTION

The invention relates to novel 3-phenyl-4-hexynoic acid derivatives exhibiting the activity as GPR40 receptor agonists, pharmaceutical compositions comprising said derivatives and their use in the treatment of GPR40 mediated diseases, in particular type 2 diabetes.

BACKGROUND ART

G-protein coupled receptors (GPCRs) are integral membrane proteins responsible for transduction of the signal through double lipid layer to effector sites inside a cell. They participate in signaling cascades through many signaling molecules: hormones, neuronal transmitters, small proteins, short peptide chains, amines, lipids, nucleotides or amino acids and fatty acids derivatives. For each of the signaling molecules a receptor or group of receptors exists that is able to bind a specific molecule thus initiating signal transduction through cell membrane. GPCRs play a key role in many physiological processes involved in the regulation of cell work, metabolism, growth and immunological defense.

G-protein coupled receptor 40 (GPR40), also known as free fatty acid receptor 1 (FFA1), is a protein expressed in pancreatic beta islets cells and to a lesser extent in the brain. This receptor is activated by fatty acids and mediates insulinotropic activity exerted by fatty acids directly on pancreatic beta cells. Insulinotropic action of GPR40 is insulin-dependent. Activation thereof results in enhancement of insulin secretion by beta cells only in the presence of elevated glucose levels, thereby the risk of hypoglycemia is diminished.

Intensive research works are underway to find small-molecule GPR40 ligands and to use them in pharmacological therapy, primarily in type 2 diabetes (Takafumi Hara, Ligands at Free Fatty Acid Receptor 1, Handbook of Experimental Pharmacology, Springer International Publishing AG 2016). Such ligands could be potentially anti-diabetic agents acting as anti-hyperglycemics without the risk of hypoglycemia. Some compounds were brought to the phase of clinical trials, however regardless their activity with respect to GPR40, they were found potentially hepatotoxic or exerted other side effects or caused elevation of insulin level without reduction of glucose level. Since GPR40 is not expressed in the liver, molecular mechanism of hepatoxicity is probably not associated directly with GPR40 activation but may probably take place downwards in the signaling cascade activated after ligand binding. This mechanism is assumingly associated with bile acids transport inhibiting activity and disturbance of bile acids homeostasis.

The compounds having GPR40 modulating activity typically comprise as common structural moiety an acidic head group, usually carboxylic group, in the phenylpropanoic acid skeleton, believed to be responsible for receptor binding, and hydrophobic tail group, usually aromatic fragment, connected with head group through a linker, typically having the length of 2-4 carbon atoms, and preferably with ether linkage. In this way, structure of fatty acids, natural GPR40 ligands, is mimicked by synthetic modulators. In the prior known compounds tail group may be a monocyclic or bicyclic group.

WO2004/041266 discloses as GPR40 function regulators compounds defined solely by the presence of an aromatic ring moiety and a group capable to release cation, in particular carboxy group.

WO2004/106276 discloses as GPR40 function regulators carboxylic acids wherein head group is a bicyclic group of the formula:

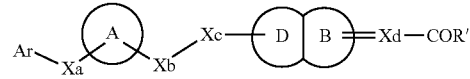

wherein A may be benzene ring, Xc may represent oxygen atom, D may represent phenyl, thienyl or thiazole ring, B is a 5-7 membered non-aromatic ring, and Xd may represent a bond, CH or $CH_2$.

WO2005/086661 discloses GPR40 modulators for controlling insulin levels of the formula:

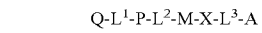

In particular, WO2005/086661 discloses as GPR40 modulators among others carboxylic acids based on phenylpropanoic acid skeleton comprising ethynyl substituent in the position beta in relation to carboxy group of the formula:

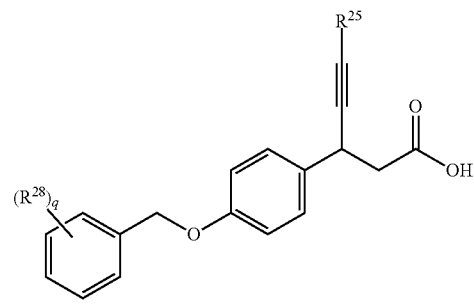

wherein $R^{25}$ is hydrogen or alkyl, oxyalkyl, aryl or heteroaryl group, especially methyl group, and $R^{28}$ is phenyl or benzyl group optionally substituted with various substituents, or pyridyl or pyryl group. WO2005/086661 discloses also the compound (3R/S)-3-[4-(prop-2-yn-1-yloxy)phenyl] hex-4-ynoic acid (compound No. 17.38) that is not encompassed by the above formulas and for which no information on biological activity is presented.

One of the compounds specifically disclosed in WO2005/086661 is (3S)-1-propyn-1-yl-4-[[4'-(trifluoromethyl)[1,1'-biphenyl]-3-yl]methoxy]benzenepropanoic acid (also known under code AMG-837) of the following structural formula:

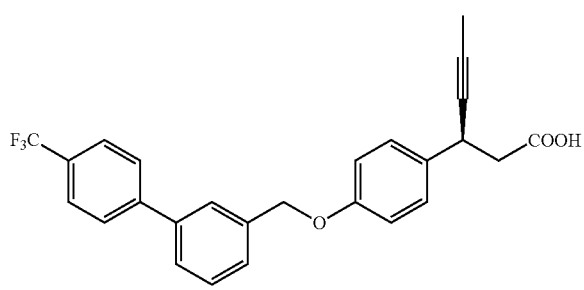 [SMILES: CC#C[C@@H](CC(=O)O)c1ccc(OCc2cccc(-c3ccc(C(F)(F)F)cc3)c2)cc1]

Reportedly this compound in the I phase of clinical trials enhanced insulin plasma level ("Free Fatty Acid Receptors" Handbook of Experimental Pharmacology, vol. 236, ISBN 978-3-319-50692-0, DOI 10.1007/978-3-319-50693-7, Springer International Publishing AG 2017, page 11). However, further development was abandoned.

WO2005/063729 discloses as GPR40 modulators the compounds with non-bicyclic head group of the formula:

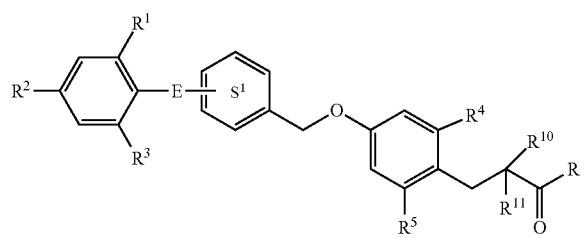

WO2005/087710 discloses compounds with bicyclic head group and nitrogen linker of the formula:

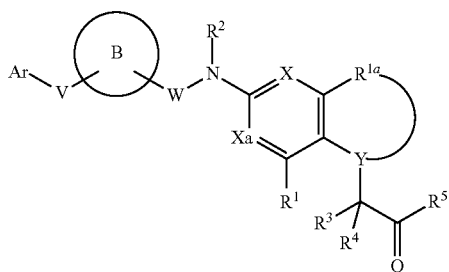

WO2008/001931 discloses as GPR40 function modulators compounds of the formula:

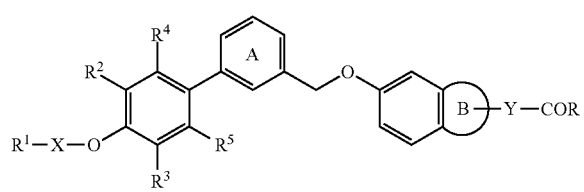

with bicyclic head group, wherein $R^1$ is alkylsulfonyl group, R is hydroxy group, and B is preferably a tetrahydropyran ring. One of the described compounds is 2-[(3S)-6-[[3-[2,6-dimethyl-4-(3-methylsulfonylpropoxy)phenyl]phenyl]methoxy]-2,3-dihydro-1-benzofuran-3-yl]acetic acid (also known as fasiglifam or TAK-875) of the following structural formula:

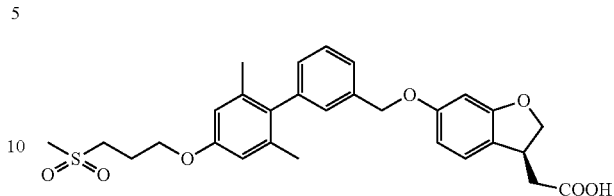

In phase 3 clinical trials this compound exhibited the ability to reduce glucose levels in type 2 diabetes patients. However, further development has been abandoned because of side effects on the liver, associated with inhibiting activity on bile acids transport and disturbance of bile acids homeostasis (A. Mancini et al., "GPR40 agonists for the treatment of type 2 diabetes: life after "TAKing" a hit", Diabetes Obesity and Metabolism 2015 vol. 17 p. 622-629).

WO2013/128378 discloses as GPR40 function modulators the compounds based on phenylpropanoic acid skeleton, having heterocyclic substituent in the position beta in relation to carboxy group, of the formula:

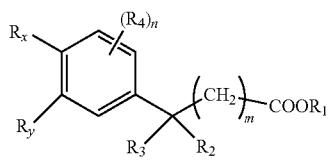

WO2011/046851 discloses as GPR40 activators carboxylic acid compounds based on phenylpropanoic acid skeleton, having ethynyl substituent in the position beta in relation to carboxy group and spiropiperidine substituent of aromatic tail fragment, of the formula:

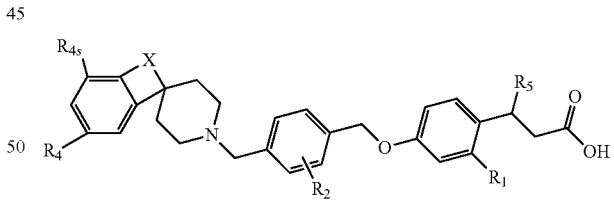

WO2013/025424 discloses GPR40 activators based on phenylpropanoic acid skeleton, having ethynyl substituent in the position beta in relation to carboxy group and 1-(thiophen-2-ylmethyl)-1,2,3,4-tetrahydroquinoline as the aromatic fragment.

WO2015/105786 discloses GPR40 activators based on phenylpropanoic acid skeleton, having ethynyl substituent in the position beta in relation to carboxy group and bicyclic triazolopyridine moiety as the aromatic fragment.

WO2012/011125 discloses GPR40 activators based on phenylpropanoic acid skeleton, having cyano substituent in the position beta in relation to carboxy group and aromatic fragment with oxime functionality.

WO2010/143733 discloses GPR40 activators of the formula:

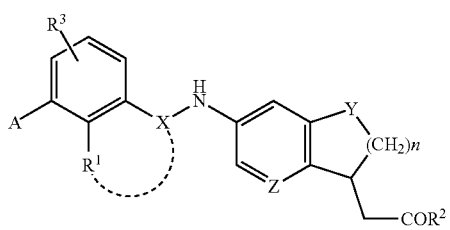

wherein ether type linker is replaced with amine type linker, Y is $CH_2$, NH or O, Z is CH or N, and X is $CH_2$ or together with R1 may form alicyclic ring.

WO2013/0125732 discloses ghrelin O-acetyltransferase (GOAT) inhibitors of the formula:

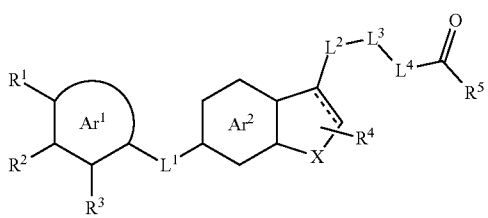

US2009/0111859 discloses as GPR40 inhibitors the compounds of the formula:

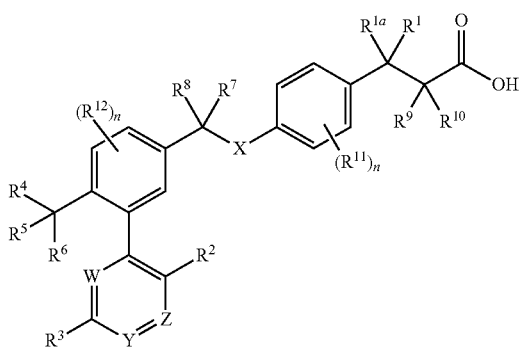

US2008/0090840 discloses as GPR40 modulators the compounds of the formula:

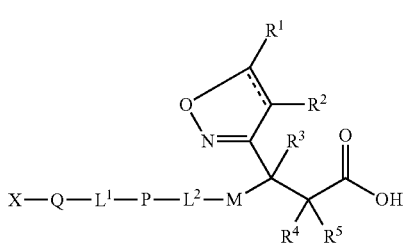

US2008/0176912 discloses as GPR40 modulators the compounds of the formula:

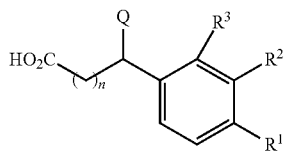

wherein Q represents phenyl or 5-membered heterocyclic ring.

WO2012/136221 discloses as GPR40 modulators the compounds of the formula:

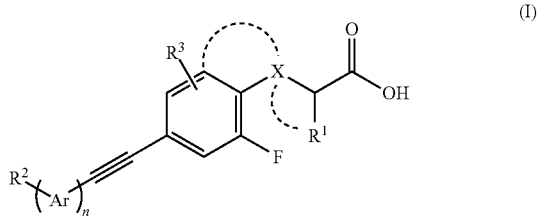

(I)

US2012/004166 discloses aryloxyalkylene-substituted hydroxyphenylhexynoic acid derivatives of the following formula, wherein A represents (C6-C10)-aryl, (C3-C10) cycloalkyl or 4 to 12-membered heterocycle, and specifically phenyl or pyridyl, having GPR40 activating and glucose plasma lowering activity, of potential utility in diabetes treatment.

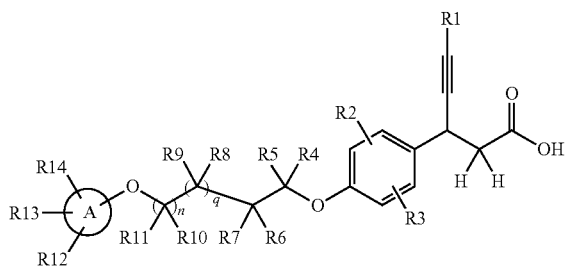

There is a need of new compounds exhibiting GPR40 receptor agonistic activity and potentially useful in the treatment of metabolic diseases, especially type 2 diabetes, preferably without exerting liver effects, especially without inhibition of bile acids secretion.

SUMMARY OF THE INVENTION

The object of the invention is a compound of the formula (I):

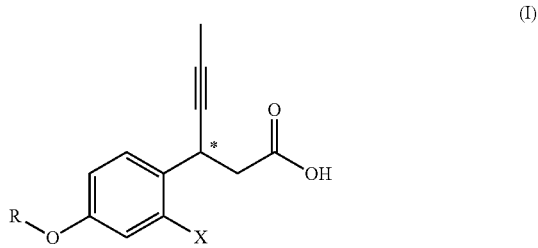

(I)

wherein:
R represents:
a straight or branched, primary or secondary acyclic hydrocarbyl C3-C15 group, which can be saturated or unsaturated, or
a straight or branched, primary or secondary acyclic hydrocarbyl C3-C15 group, which can be saturated or unsaturated and wherein one or more of hydrogen atoms is replaced with fluorine atom;
X represents hydrogen atom or halogen atom,
* denotes chiral center,
and salts thereof, especially pharmaceutically acceptable salts,
with the proviso that formula (I) excludes 3-(4-{[(2E,3Z)-2-propylidenepent-3-en-1-yl]oxy}phenyl)hex-4-ynoic acid and (3R/S)-3-[4-(prop-2-yn-1-yloxy)phenyl]hex-4-ynoic acid.

3-(4-{[(2E,3Z)-2-Propylidenepent-3-en-1-yl]oxy}phenyl)hex-4-ynoic acid is the compound included in the National Center for Biotechnology Information database. PubChem Substance Database; SID=344303732, https://pubchem.ncbi.nlm.nih.gov/substance/344303732 (access of 20 Oct. 2017). No information on its biological activity or its use has been provided. (3R/S)-3-[4-(Prop-2-yn-1-yloxy)phenyl]hex-4-ynoic acid is disclosed in WO2005/086661, although its activity has not been reported.

Contrary to the GPR40 modulators known from the prior art, compounds of the invention do not possess aromatic or (hetero)cyclic ring in the tail moiety, while exhibiting GPR40 receptor modulating activity. Compounds of the invention do not exhibit the activity of bile acids transporters inhibition, hence can be free of hepatotoxic action.

Compounds of the invention, being the compounds with free carboxy group, can exist as liquids in normal condition (syrups, oils), therefore there is no risk of their crystallization in hepatocytes, what had happen in the case of prior GPR40 activators of high molecular weight, as in the case of TAK-875 (Wolenski F. S., 2017, "Fasiglifam (TAK-875) Alters Bile Acid Homeostasis in Rats and Dogs: A Potential Cause of Drug Induced Liver Injury", TOXICOLOGICAL SCIENCES, 157(1), 2017, 50-61).

Simultaneously, the same compounds can be converted into suitable, pharmaceutically acceptable solid salts, which due to their physical state are more convenient and practical form for manufacturing and purification of the compounds of the invention to the form of the active ingredient of pharmaceutical composition (API).

Compounds of the invention possess reduced molecular weight (MW) with respect to the reference compound (fasiglifam, TAK-875), while having comparable or higher activity (EC50 value) than said reference compound. This means better "molecular yield" (i.e. ligand efficiency (LE) value). In other words, using lower number of atoms for the construction of a GPR40 agonist ligand than in the reference compound, compounds of the invention allow to obtain comparable or better biological effect. This also means that from the one side the economy of manufacturing is better, and from the other side the number of the side effects may potentially be lower number due to simultaneous decrease of the lipophilicity associated with the reduction of molecular weight.

Compounds of formula (I), as GPR40 receptors ligands, possess the GPR40 receptor modulating ability activity (they are agonists) and can find use in the treatment of GPR40 mediated diseases.

In another aspect, the object of the invention is also the compound of formula (I) as defined above for use as a medicament.

In a further aspect, the object of the invention is also a pharmaceutical composition comprising the compound of formula (I) as defined above together with pharmaceutical excipients.

In a further aspect, the object of the invention is also a use of the compound of formula (I) as defined above for the preparation of a medicament for the treatment of GPR40 mediated diseases.

In a further aspect, the object of the invention is also a method of treatment of diseases mediated by GPR40 in a subject in need thereof, said method comprising administering to said subject an effective amount of the compound of the formula (I) as defined above.

In a further aspect, the object of the invention is the compound of the formula (I) as defined above for use in a method of treatment of diseases mediated by GPR40 in a subject in need thereof, said method comprising administering to said subject an effective amount of the said compound.

Diseases mediated by GPR40 include cancers and metabolic diseases, including diseases such as diabetes, type 2 diabetes, obesity, hyperglycemia, glucose intolerance, insulin resistance, hyperinsulinemia, hypercholesterolemia, neuropathies and metabolic syndrome.

DETAILED DESCRIPTION OF THE INVENTION

Preferred embodiments of the invention are described in the following detailed description and appended claims. Various aspects of the invention are defined more precisely herein. Each of the aspects so defined can be combined with any other aspect or aspects, unless expressly indicated otherwise. In particular, any of the features indicated as preferred or advantageous can be combined with any other feature or features indicated as preferred or advantageous.

Reference throughout the description to "one of embodiments" or "an embodiment" means that specific feature, structure or characteristics described in connection with this embodiment is comprised in at least one embodiment of the present invention. Thus the appearance of expressions "in one of embodiments" or "in an embodiment" in various places of this description not necessarily relates to the same embodiment, but it can. Furthermore, specific features, structures or characteristics can be combined in any suitable manner, as it will be appreciated by a person skilled in the art, in one or more embodiments. Furthermore, although some of the embodiments described herein comprise some but not other features comprised in other embodiments, combinations of features of various embodiments can be encompassed by the scope of the invention and form various examples of realization of the invention, as it will be appreciated by a skilled person. For example, in the appended claims any of the claimed embodiments can be used in any combination.

In the first aspect, the object of the invention is a compound of the formula (I)

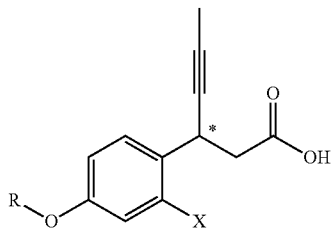

(I)

wherein:
R represents:
  a straight or branched, primary or secondary acyclic hydrocarbyl C3-C15 group, which can be saturated or unsaturated, or
  a straight or branched, primary or secondary acyclic hydrocarbyl C3-C15 group, which can be saturated or unsaturated and wherein one or more of hydrogen atoms is replaced with fluorine atom;
X represents hydrogen atom or halogen atom,
* denotes chiral center,
and salts thereof, especially pharmaceutically acceptable salts,
with the proviso that formula (I) excludes 3-(4-{[(2E,3Z)-2-propylidenepent-3-en-1-yl]oxy}phenyl)hex-4-ynoic acid and (3R/S)-3-[4-(prop-2-yn-1-yloxy)phenyl]hex-4-ynoic acid.

In a further aspect, the object of the invention is a compound of the formula (I)

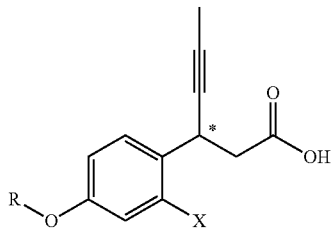

(I)

wherein:
R represents:
  a straight or branched, primary or secondary acyclic hydrocarbyl C4-C15 group, which can be saturated or unsaturated, or
  a straight or branched, primary or secondary acyclic hydrocarbyl C4-C15 group, which can be saturated or unsaturated and wherein one or more of hydrogen atoms is replaced with fluorine atom;
X represents hydrogen atom or halogen atom,
* denotes chiral center,
and salts thereof, especially pharmaceutically acceptable salts,
with the proviso that formula (I) excludes 3-(4-{[(2E,3Z)-2-propylidenepent-3-en-1-yl]oxy}phenyl)hex-4-ynoic acid.

In one of the embodiments of both aspects of the compounds of formula (I) R represents a straight or branched acyclic hydrocarbyl C4-C15 group, especially, C4-C12 group, that may be saturated or unsaturated.

In one of the embodiments of both aspects of the compounds of formula (I) R represents a straight or branched saturated acyclic hydrocarbyl C4-C15 group, especially C4-C12 group.

A preferred straight saturated hydrocarbyl group is n-butyl.

Another preferred straight saturated hydrocarbyl group is n-pentyl.

Another preferred straight saturated hydrocarbyl group is n-hexyl.

Another preferred straight saturated hydrocarbyl group is n-heptyl.

A preferred branched saturated hydrocarbyl group is 3-methylbutyl.

Another preferred branched saturated hydrocarbyl group is iso-butyl.

Another preferred branched saturated hydrocarbyl group is sec-butyl.

Another preferred branched saturated hydrocarbyl group is 2-methyl-1-butyl.

Another preferred branched saturated hydrocarbyl group is 2-ethyl-1-butyl.

Another preferred branched saturated hydrocarbyl group is 2-pentyl.

Another preferred branched saturated hydrocarbyl group is 3-methyl-2-butyl.

In one of the embodiments of both aspects of the compounds of formula (I) of the invention R represents a straight or branched unsaturated acyclic hydrocarbyl C4-C15 group, especially C4-C12 group.

Said straight or branched unsaturated acyclic hydrocarbyl C3-C15 or C4-C15 group, especially C4-C12 group, may comprise one double bond or more than one double bond in a conjugated or non-conjugated system in the stereochemical configuration E or Z. Preferably, said hydrocarbyl C3-C15 or C4-C15 group, especially C4-C12 group, comprises two double bonds in a non-conjugated or conjugated system. Said straight or branched unsaturated acyclic hydrocarbyl C3-C15 or C4-C15 group, especially C4-C12 group, may also comprise one or more triple bonds, preferably one triple bond.

Preferably, in all groups, subgroups and embodiments described above said unsaturated acyclic hydrocarbyl group as unsaturated bonds comprises solely double bonds.

Preferred unsaturated acyclic hydrocarbyl C3-C15 and C4-C15 groups are (2E)-2-hexen-1-yl, (2E,4E)-2,4-hexadien-1-yl, 3-methyl-2-buten-1-yl, 3-methyl-3-buten-1-yl, 2,3-dimethyl-2-buten-1-yl, and (2E)-3,7-dimethyl-2,6-octadien-1-yl.

In one of the embodiments one or more of hydrogen atoms at the saturated or unsaturated carbon atoms of the acyclic hydrocarbyl C3-C15 or C4-C15 group, especially C4-C12 group, may be replaced with one or more than one fluorine atom, for example one, two or three hydrogen atoms at the same carbon atom may be replaced with one, two or three fluorine atoms to form $CH_2F$, $CHF_2$ or $CF_3$ group, respectively.

Examples of partially fluorinated and perfluorinated commercially available compounds (alcohols and alkyl halides) that can be used as a source for the preparation of acyclic, partially fluorinated or perfluorinated R group of the compound of formula (I) are presented in Table 1. A skilled person will appreciate that structural motifs of partial substitution with fluorine atom or atoms for smaller fragments presented in Table 1 may be analogously repeated for any structural part the acyclic hydrocarbyl C3-C15 or C4-C15 group.

TABLE 1

| Structure | CAS No. or supplier | Name |
|---|---|---|
| (F-CH2-CH2-CH2-OH) | Sigma-Aldrich | 3-Fluoro-1-propanol |
| (CHF2-CF2-CH2-OH) | 76-37-9 | 2,2,3,3-Tetrafluoro-1-propanol |
| (CF3-CH2-CH2-OH) | Sigma-Aldrich | 3,3,3-Trifluoro-1-propanol |
| (CF3-CF2-CH2-OH) | 422-05-9 | 2,2,3,3,3-Pentafluoro-1-propanol |
| (CF3-CF2-CF2-I) | 754-34-7 | Perfluoropropyl iodide |
| (CF3-CH2-CH(OH)-CH3) | Sigma-Aldrich | 4,4,4-Trifluoro-2-butanol |
| (CF3-CH2-CH2-CH2-OH) | 461-18-7 | 4,4,4-Trifluoro-1-butanol |
| (CF3-CH2-CH(CH3)-CH2-OH) | Sigma-Aldrich | 4,4,4-Trifluoro-2-methylo-1-butanol |
| (CF3-CF2-CH2-CH2-OH) | Sigma-Aldrich | 3,3,4,4,4-Pentafluoro-1-butanol |
| (CF3-CF2-CF2-CF2-I) | 423-39-2 | Nonafluoro-1-iodobutane |
| (CF3-C(CF3)(F)-CH2-CH2-OH) | Sigma-Aldrich | 3,4,4,4-Tetrafluoro-3-(trifluoromethyl)butan-1-ol |
| (CF3-CF2-CF2-CHF-CH2-OH) | 375-01-9 | 2,2,3,3,4,4,4-Heptafluoro-1-butanol |

TABLE 1-continued

| Structure | CAS No. or supplier | Name |
|---|---|---|
| 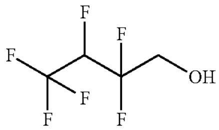 [SMILES: OCC(F)(F)C(F)C(F)(F)F] | 382-31-0 | 2,2,3,4,4,4-Hexafluoro-1-butanol |
| 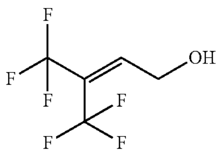 [SMILES: OCC=C(C(F)(F)F)C(F)(F)F] | 102710-48-5 | 4,4,4-Trifluoro-3-(trifluoromethyl)-2-buten-1-ol |
| 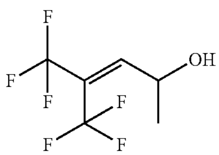 | 656-80-4 | 5,5,5-Trifluoro-4-trifluoromethyl-3-penten-2-ol |
| 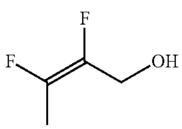 | 123028-48-8 | (Z)-3-Methyl-2,3-difluoroallyl alcohol |
| 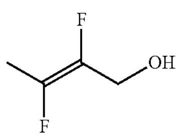 | 123028-47-7 | (E)-3-Methyl-2,3-difluoroallyl alcohol |
| 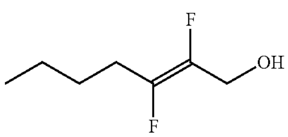 | 123028-51-3 | (E)-3-butyl-2,3-difluoroallyl alcohol |
| 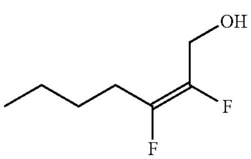 | 123028-52-4 | (Z)-3-butyl-2,3-difluoroallyl alcohol |
| 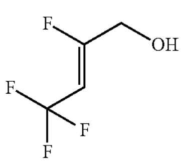 | 91600-37-2 | 2,4,4,4-Tetrafluoro-2-buten-1-ol |
| 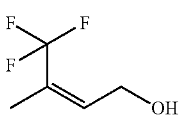 | 59867-95-7 | 4,4,4-Trifluoro-3-methyl-2-buten-1-ol |
| 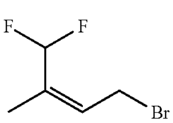 | 104715-02-8 | (Z)-1-Bromo-3-(difluoromethyl)-2-buten |
| 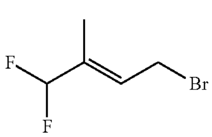 | 104715-03-9 | (E)-1-Bromo-3-(difluoromethyl)-2-buten |

TABLE 1-continued

| Structure | CAS No. or supplier | Name |
|---|---|---|
| 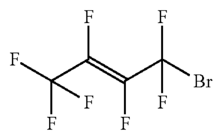 | 72990-82-0 | trans-1-Bromoheptafluoro-2-butene |
| 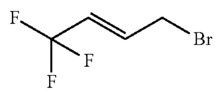 | 31450-13-2 | 1,1,1-Trifluoro-4-bromo-2-butene |
| 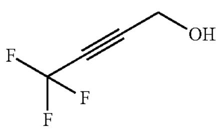 | 113439-92-2 | 4,4,4-Trifluoro-2-butyn-1-ol |
| 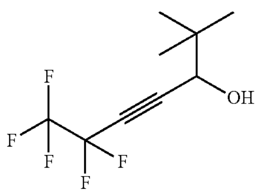 | 103245-51-8 | 6,6,7,7,7-Pentafluoro-2,2-dimethyl-4-heptyn-3-ol |
| 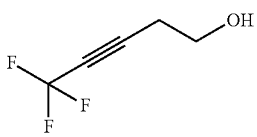 | 27611-20-7 | 5,5,5-Trifluoro-3-pentyn-1-ol |

In one of the embodiments X represents hydrogen atom.

In another embodiment X represents halogen atom, especially preferred is fluorine atom.

The invention encompasses compound of the formula (I) in the form of a single enantiomer, single diastereoisomer, racemate or a mixture of enantiomers or diastereoisomers.

In a particular and preferred embodiment the compound as defined above is a single enantiomer or diastereoisomer having the structure (Ia)

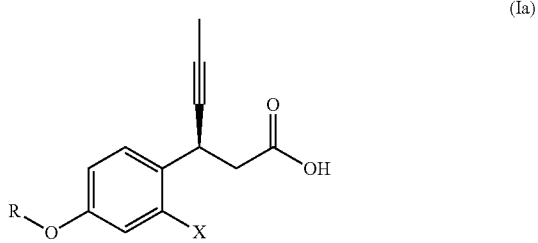

(Ia)

Definitions

The term "straight or branched acyclic hydrocarbyl group" as used herein relates to hydrocarbyl group having the straight- or branched chain connected with single carbon-carbon bonds, with the number of carbon atoms as indicated in respective definition. The number or range of numbers given after the carbon atom symbol (C) relates to the number of carbon atoms that the group may contain. For example, C3-C15 alkyl means acyclic hydrocarbyl group with 3 to 15 carbon atoms, C4-C15 alkyl means acyclic hydrocarbyl group with 4 to 15 carbon atoms, C4-C12 alkyl means acyclic hydrocarbyl group with 4 to 12 carbon atoms, and C4-C10 alkyl means acyclic hydrocarbyl group with 4 to 10 carbon atoms, etc. Said term excludes hydrocarbyl groups having the ring structure. It will be obvious for a skilled person that primary acyclic hydrocarbyl group is a group wherein carbon atom of its attachment is connected only with one other carbon atoms, and secondary acyclic hydrocarbyl group is a group wherein carbon atom of its attachment is connected only with two other carbon atoms. Carbon atoms in a chain of acyclic hydrocarbyl group are connected only with single carbon-carbon bonds in case of saturated acyclic hydrocarbyl group, and may contain one or more double or triple carbon-carbon bonds in case of unsaturated acyclic hydrocarbyl group. Excluded are tertiary acyclic hydrocarbyl groups wherein carbon atom of its attachment point is connected with three other carbon atoms.

Exemplary saturated acyclic hydrocarbyl C3-C15 groups are propyl, iso-propyl, n-butyl, iso-butyl, sec-butyl, n-pentyl, 3-methylbut-1-yl, 2-methylbut-1-yl, pent-2-yl, pent-3-yl, 3-methyl-but-2-yl, 2,2-dimethylprop-1-yl (neo-pentyl), n-hexyl, hex-2-yl, hex-3-yl, 2-methylpent-1-yl, 3-methylpent-1-yl, 4-methylpent-1-yl, 3-methyl-pent-2-yl, 4-methylpent-2-yl, 2-methylpent-3-yl, 2,2-dimethylbut-1-yl, 2,3-dimethylbut-1-yl, 3,3-dimethylbut-1-yl, 3,3-dimethylbut-2-yl, 2-ethylbut-1-yl, and analogous feasible C7-C15 isomers, with the exclusion of tertiary groups.

Exemplary unsaturated acyclic hydrocarbyl C3-C15 groups are allyl, 2-propyn-1-yl, 3-buten-1-yl, (2E)-2-buten-1-yl, (2Z)-2-buten-1-yl, 3-buten-2-yl, 3-butyn-1-yl, 2-butyn-1-yl, 3-butyn-2-yl, 4-penten-1-yl, (3E)-3-penten-1-yl, (3Z)-3-penten-1-yl, (2E)-2-penten-1-yl, (2Z)-2-penten-1-yl, (2E)-2,4-pentadien-1-yl, (2Z)-2,4-pentadien-1-yl, 3-methyl-3-buten-1-yl, 3-methyl-2-buten-1-yl, 2-methyl-3-buten-1-yl, (2E)-2-methyl-2-buten-1-yl, (2Z)-2-methyl-2-buten-1-yl, 2-methylidenebutan-1-yl, 4-penten-2-yl, (3E)-3-penten-2-yl, (3Z)-3-penten-2-yl, 3-methyl-3-buten-2-yl, 1-penten-3-yl, 1,4-pentadien-3-yl, 4-pentyn-1-yl, 3-pentyn-1-yl, 2-pentyn-1-yl, (2E)-pent-2-en-4-yn-1-yl, (2Z)-pent-2-en-4-yn-1-yl, pent-4-en-2-yn-1-yl, 2-methyl-3-butyn-1-yl, 2-methylidene-3-butyn-1-yl, 4-pentyn-2-yl, 3-pentyn-2-yl, 1-pentyn-3-yl, 1,4-pentadiyn-3-yl, 5-hexen-1-yl, (4E)-4-hexen-1-yl, (4Z)-4-hexen-1-yl, (3E)-3-hexen-1-yl, (3Z)-3-hexen-1-yl, (2E)-2-hexen-1-yl, (2Z)-2-hexen-1-yl, (3E)-3,5-hexadien-1-yl, (3Z)-3,5-hexadien-1-yl, (2E,4E)-2,4-hexadien-1-yl, (2Z,4Z)-2,4-hexadien-1-yl, (2E,4Z)-2,4-hexadien-1-yl, (2Z,4E)-2,4-hexadien-1-yl, (2E)-2,5-hexadien-1-yl, (2Z)-2,5-hexadien-1-yl, 5-hexen-2-yl, (4E)-4-hexen-2-yl, (4Z)-4-hexen-2-yl, (3E)-3-hexen-2-yl, (3Z)-3-hexen-2-yl, (3E)-3,5-hexadien-2-yl, (3Z)-3,5-hexadien-2-yl, 5-hexen-3-yl, (4E)-4-hexen-3-yl, (4Z)-4-hexen-3-yl, 1-hexen-3-yl, 1,5-hexadien-3-yl, (4E)-1,4-hexadien-3-yl, 2-methyl-4-penten-1-yl, (3E)-2-methyl-3-penten-1-yl, (3Z)-2-methyl-3-penten-1-yl, (2E)-2-methyl-2-penten-1-yl, (2Z)-2-methyl-2-penten-1-yl, 2-methylidenepentan-1-yl, (2E)-2-methyl-2,4-pentadien-1-yl, (2Z)-2-methyl-2,4-pentadien-1-yl, 2-methylidene-4-penten-1-yl, (3E)-2-methylidene-3-penten-1-yl, (3Z)-2-methylidene-3-penten-1-yl, 3-methyl-4-penten-1-yl, (3E)-3-methyl-3-penten-1-yl, (3Z)-3-methyl-3-penten-1-yl, (2E)-3-methyl-2-penten-1-yl, (2Z)-3-methyl-2-penten-1-yl, 3-methylidenepentan-1-yl, 3-methyliden-4-penten-1-yl, (2E)-3-methyl-2,4-pentadien-1-yl, (2Z)-3-methyl-2,4-pentadien-1-yl, 4-methyl-4-penten-1-yl, 4-methyl-3-penten-1-yl, (2E)-4-methyl-2-penten-1-yl, (2Z)-4-methyl-2-penten-1-yl, (2E)-4-methyl-2,4-pentadien-1-yl, (2Z)-4-methyl-2,4-pentadien-1-yl, 3-methyl-4-penten-2-yl, (3E)-3-methyl-3-penten-2-yl, (3Z)-3-methyl-3-penten-2-yl, 3-methylidenepentan-2-yl, 3-methylidene-4-penten-2-yl, 4-methyl-4-penten-2-yl, 4-methyl-3-penten-2-yl, 4-methyl-1-penten-3-yl, 2-methyl-1-penten-3-yl, 2-methyl-1,4-pentadien-3-yl, 2,2-dimethyl-3-buten-1-yl, 2,3-dimethyl-3-buten-1-yl, 2,3-dimethyl-2-buten-1-yl, 3-methyl-2-methylidenebutan-1-yl, 3-methyl-2-methylidene-3-buten-1-yl, 2-ethyl-3-buten-1-yl, (2E)-2-ethyl-2-buten-1-yl, (2Z)-2-ethyl-2-buten-1-yl, (2E)-2-ethylidene-3-buten-1-yl, (2Z)-2-ethylidene-3-buten-1-yl, 2-ethenyl-3-buten-1-yl, 5-hexyn-1-yl, 4-hexyn-1-yl, 3-hexyn-1-yl, 2-hexyn-1-yl, 3,5-hexadiyn-1-yl, 2,5-hexadiyn-1-yl, 2,4-hexadiyn-1-yl, (3E)-hex-3-en-5-yn-1-yl, (3Z)-hex-3-en-5-yn-1-yl, (2E)-hex-2-en-5-yn-1-yl, (2Z)-hex-2-en-5-yn-1-yl, (2E)-hex-2-en-4-yn-1-yl, hex-5-en-3-yn-1-yl, hex-5-en-2-yn-1-yl, (4E)-hex-4-en-2-yn-1-yl, (4Z)-hex-4-en-2-yn-1-yl, 5-hexyn-2-yl, 4-hexyn-2-yl, 3-hexyn-2-yl, 3,5-hexadiyn-2-yl, (3E)-hex-3-en-5-yn-2-yl, (3Z)-hex-3-en-5-yn-2-yl, hex-5-en-3-yn-2-yl, 5-hexyn-3-yl, 4-hexyn-3-yl, 1-hexyn-3-yl, 1,5-hexadiyn-3-yl, 1,4-hexadiyn-3-yl, hex-1-en-5-yn-3-yl, hex-5-en-1-yn-3-yl, (4E)-hex-4-en-1-yn-3-yl, (4Z)-hex-4-en-1-yn-3-yl, hex-1-en-4-yn-3-yl, 2-methyl-4-pentyn-1-yl, 2-methyl-3-pentyn-1-yl, (2E)-2-methylpent-2-en-4-yn-1-yl, (2Z)-2-methylpent-2-en-4-yn-1-yl, 2-methylidene-4-pentyn-1-yl, 2-methylidene-3-pentyn-1-yl, 3-methyl-4-pentyn-1-yl, 3-methylidene-4-pentyn-1-yl, (2E)-3-methylpent-2-en-4-yn-1-yl, (2Z)-3-methylpent-2-en-4-yn-1-yl, 4-methyl-2-pentyn-2-yl, 4-methylpent-4-en-2-yn-1-yl, 3-methyl-4-pentyn-2-yl, 3-methylidenepent-4-yn-2-yl, 4-methyl-1-pentyn-3-yl, 2-methylpent-1-en-4-yn-3-yl, 2,2-dimethyl-3-butyn-1-yl, 2-ethyl-3-butyn-1-yl, 2-ethynyl-3-butyn-1-yl, (2E)-2-ethynyl-2-buten-1-yl, (2Z)-2-ethynyl-2-buten-1-yl, 2-ethynyl-3-buten-1-yl, and analogous feasible C7-C15 isomers, with the exclusion of tertiary groups.

Halogen means fluorine (F), chlorine (Cl), bromine (Br) or iodine atom, especially fluorine atom.

Compounds of the formula (I) comprise carboxy group and may form salts with metals, ammonia and with organic bases, including but without such limitation, pharmaceutically acceptable salts and salts with basic ion exchange resins (for example cholestyramine). Metal salts comprise in particular alkali metal salts, including sodium, potassium and lithium salt, alkaline earth metal salts, including in particular calcium, magnesium and barium salt. Salts with organic bases include salts with amines, especially with aliphatic amines, such as trimethylamine, triethylamine, cyclohexylamine, tert-butylamine, N-(phenylmethyl)benzene-ethylamine, N,N'-dibenzylethylenediamine, choline, 2-(dimethylamino)ethanol, diethanoloamine, diethylamine, 2-(diethylamino)ethanol, ethanoloamine, ethylenediamine, N-methylglucamine, hydrabamine, morpholine, 4-(2-hydroxy-ethyl)morpholine, piperazine, 1-(2-hydroxyethyl)pyrrolidine, triethanoloamine, 2-amino-2-(hydroxymethyl)propano-1,3-diol, amino acids, such arginine, lysine, histidine or ornithine, aromatic amines, such as aniline, methylaniline, naphthyl-amine, or heterocyclic amines, such as for example 1H-imidazole or pyridine.

It should be understood that the scope of the invention encompasses also salts other than pharmaceutically acceptable ones, that can be useful especially as intermediate products in the processes of manufacture, isolation and purification of the compounds of the invention. Salts of the compounds of formula (I) can be obtained by direct combination of the compound of formula (I) with an amine (aliphatic, aromatic, heterocyclic) in a protic or aprotic solvent or mixture of solvents, for example in acetone, acetonitrile or toluene. In the case of spontaneous crystallization under such conditions, solid precipitate is filtered-off and dried. In the case of lack of spontaneous crystallization under such conditions, the solution of a salt can be concentrated or evaporate to dryness. Such a process can be also performed without a solvent, by direct trituration of respective components. Inorganic salts of the compounds of formula (I) can be also obtained by dissolving of the starting acid of formula (I) in aqueous or containing water solution of respective hydroxide, for example sodium or potassium hydroxide, or ammonium hydroxide, or also respective unstable alkali metal carbonates or bicarbonates. Desired salt may be obtained from such a solution in a similar manner as in the case of organic amines, or such a solution can be combined with another salt (inorganic or organic) to obtain desired salt in the exchange reaction. In the case of reactive metals, such as sodium or potassium, it is possible to obtain respective salt by direct reaction of the compound of formula (I) with metal, in the presence of inert solvent or without a solvent. Salts of the compounds of formula (I) may be converted into compounds of formula (I) with free carboxy group by acidification of the salt solution with an acid, for example hydrochloric, sulfuric, phosphoric, or citric acid and subsequent extraction with suitable organic solvent, for example diethyl ether, ethyl acetate, chloroform, or dichloromethane. In the extraction process salt of the compound of formula (I) neutralized to the free acid form passes to the organic phase which is then separated, dried an concentrated.

Compounds of the invention include chiral center at the carbon atom to which propyn-1-yl (methylacetylene) substituent is attached. Therefore, the compounds may exist in the form of enantiomers or mixtures of enantiomers at various ratios, in particular racemic mixtures (racemates). It should be understood that enantiomer of the compound of formula (I) will be substantially optically pure, but usually may contain some percentage of the opposite enantiomer, such as for example up to 10%, 5%, 3%, 2%, 1% or 0.5% of the opposite enantiomer.

Compounds of the invention include further prochiral center(s) present in the hydrocarbyl group C3-C15 and therefore may exist in the form of enantiomers, mixtures of enantiomers at various ratios, in particular racemic mixtures (racemates), as well as in the form of diastereoisomers and their mixtures.

Enantiomers of the compounds of the formula (I) may be obtained by asymmetric synthesis, starting from suitable chiral starting material. Alternatively, enantiomers of the compounds of the formula (I) may be obtained by resolution of racemic mixture using methods well known for a skilled person, including preparative high-performance liquid chromatography (HPLC), HPLC chromatographic resolution on chiral stationary phase or by formation of optically active diastereoisomeric derivatives with chiral auxiliaries and fractionated crystallization of diastereoisomeric pairs and removal of chiral auxiliary. For example, racemic mixture may be resolved by chiral HPLC into two enantiomers, enantiomer A with shorter retention time and enantiomer B with longer retention time. Retention time in a chiral chromatography process in a given system of stationary phase and an eluent is a physical parameter that identifies enantiomer. Absolute stereochemistry of an enantiomer can be subsequently determined using known methods.

Specific compounds of the invention are selected from the group consisting of the following compounds and their salts, especially pharmaceutically acceptable salts:

1) (3S)-3-(4-propoxyphenyl)hex-4-ynoic acid
2) (3R)-3-(4-propoxyphenyl)hex-4-ynoic acid
3) (3S)-3-(4-butoxyphenyl)hex-4-ynoic acid
4) (3R)-3-(4-butoxyphenyl)hex-4-ynoic acid
5) (3S)-3-[4-(pentyloxy)phenyl]hex-4-ynoic acid
6) (3R)-3-[4-(pentyloxy)phenyl]hex-4-ynoic acid
7) (3S)-3-[4-(hexyloxy)phenyl]hex-4-ynoic acid
8) (3R)-3-[4-(hexyloxy)phenyl]hex-4-ynoic acid
9) (3S)-3-[4-(heptyloxy)phenyl]hex-4-ynoic acid
10) (3R)-3-[4-(heptyloxy)phenyl]hex-4-ynoic acid
11) (3S)-3-(4-{[(2E)-3,7-dimethylocta-2,6-dien-1-yl]oxy}phenyl)hex-4-ynoic acid
12) (3R)-3-(4-{[(2E)-3,7-dimethylocta-2,6-dien-1-yl]oxy}phenyl)hex-4-ynoic acid
13) (3S)-3-(4-{[(3R)-3,7-dimethyloct-6-en-1-yl]oxy}phenyl)hex-4-ynoic acid
14) (3R)-3-(4-{[(3R)-3,7-dimethylocta-6-en-1-yl]oxy}phenyl)hex-4-ynoic acid
15) (3S)-3-(4-{[(3S)-3,7-dimethyloct-6-en-1-yl]oxy}phenyl)hex-4-ynoic acid
16) (3R)-3-(4-{[(3S)-3,7-dimethyloct-6-en-1-yl]oxy}phenyl)hex-4-ynoic acid
17) (3S)-3-(4-{[(2Z)-3,7-dimethylocta-2,6-dien-1-yl]oxy}phenyl)hex-4-ynoic acid
18) (3R)-3-(4-{[(2Z)-3,7-dimethylocta-2,6-dien-1-yl]oxy}phenyl)hex-4-ynoic acid
19) (3R)-3-(4-{[(2E,6E)-3,7,11-trimethyldodeca-2,6,10-trien-1-yl]oxy}phenyl)-hex-4-ynoic acid
20) (3S)-3-(4-{[(2E,6E)-3,7,11-trimethyldodeca-2,6,10-trien-1-yl]oxy}phenyl)hex-4-ynoic acid
21) (3S)-3-[4-(2-methylpropoxy)phenyl]hex-4-ynoic acid
22) (3R)-3-[4-(2-methylpropoxy)phenyl]hex-4-ynoic acid
23) (3S)-3-(4-{[(2R)-3-methylbutan-2-yl]oxy}phenyl)hex-4-ynoic acid
24) (3R)-3-(4-{[(2R)-3-methylbutan-2-yl]oxy}phenyl)hex-4-ynoic acid
25) (3S)-3-(4-{[(2S)-3-methylbutan-2-yl]oxy}phenyl)hex-4-ynoic acid
26) (3R)-3-(4-{[(2S)-3-methylbutan-2-yl]oxy}phenyl)hex-4-ynoic acid
27) (3S)-3-{4-[(2R)-butan-2-yloxy]phenyl}hex-4-ynoic acid
28) (3R)-3-{4-[(2R)-butan-2-yloxy]phenyl}hex-4-ynoic acid
29) (3S)-3-{4-[(2S)-butan-2-yloxy]phenyl}hex-4-ynoic acid
30) (3R)-3-{4-[(2S)-butan-2-yloxy]phenyl}hex-4-ynoic acid
31) (3S)-3-{4-[(2S)-pentan-2-yloxy]phenyl}hex-4-ynoic acid
32) (3R)-3-{4-[(2S)-pentan-2-yloxy]phenyl}hex-4-ynoic acid
33) (3S)-3-{4-[(2R)-pentan-2-yloxy]phenyl}hex-4-ynoic acid
34) (3R)-3-{4-[(2R)-pentan-2-yloxy]phenyl}hex-4-ynoic acid
35) (3S)-3-[4-(pentan-3-yloxy)phenyl]hex-4-ynoic acid
36) (3R)-3-[4-(pentan-3-yloxy)phenyl]hex-4-ynoic acid
37) (3S)-3-{4-[(2E)-hex-2-en-1-yloxy]phenyl}hex-4-ynoic acid
38) (3R)-3-{4-[(2E)-hex-2-en-1-yloxy]phenyl}hex-4-ynoic acid
39) (3S)-3-{4-[(2E,4E)-hexa-2,4-dien-1-yloxy]phenyl}hex-4-ynoic acid
40) (3R)-3-{4-[(2E,4E)-hexa-2,4-dien-1-yloxy]phenyl}hex-4-ynoic acid
41) (3S)-3-[4-(pent-4-en-1-yloxy)phenyl]hex-4-ynoic acid
42) (3R)-3-[4-(pent-4-en-1-yloxy)phenyl]hex-4-ynoic acid
43) (3S)-3-[4-(pent-3-yn-1-yloxy)phenyl]hex-4-ynoic acid
44) (3R)-3-[4-(pent-3-yn-1-yloxy)phenyl]hex-4-ynoic acid
45) (3S)-3-[4-(pent-2-yn-1-yloxy)phenyl]hex-4-ynoic acid
46) (3R)-3-[4-(pent-2-yn-1-yloxy)phenyl]hex-4-ynoic acid
47) (3R)-3-[4-(3-methylbutoxy)phenyl]hex-4-ynoic acid
48) (3S)-3-[4-(3-methylbutoxy)phenyl]hex-4-ynoic acid
49) (3S)-3-[4-(2-ethylbutoxy)phenyl]hex-4-ynoic acid
50) (3R)-3-[4-(2-ethylbutoxy)phenyl]hex-4-ynoic acid
51) (3R)-3-[4-(2,2-dimethylpropoxy)phenyl]hex-4-ynoic acid
52) (3S)-3-[4-(2,2-dimethylpropoxy)phenyl]hex-4-ynoic acid
53) (3S)-3-[4-(3,3-dimethylbutoxy)phenyl]hex-4-ynoic acid
54) (3R)-3-[4-(3,3-dimethylbutoxy)phenyl]hex-4-ynoic acid
55) (3S)-3-{4-[(3-methylbut-2-en-1-yl)oxy]phenyl}hex-4-ynoic acid
56) (3R)-3-{4-[(3-methylbut-2-en-1-yl)oxy]phenyl}hex-4-ynoic acid
57) (3S)-3-{4-[(3-methylbut-3-en-1-yl)oxy]phenyl}hex-4-ynoic acid
58) (3R)-3-{4-[(3-methylbut-3-en-1-yl)oxy]phenyl}hex-4-ynoic acid
59) (3R)-3-{2-fluoro-4-[(3-methylbut-2-en-1-yl)oxy]phenyl}hex-4-ynoic acid
60) (3S)-3-{2-fluoro-4-[(3-methylbut-2-en-1-yl)oxy]phenyl}hex-4-ynoic acid
61) (3S)-3-{4-[(2,3-dimethylbut-2-en-1-yl)oxy]phenyl}hex-4-ynoic acid
62) (3R)-3-{4-[(2,3-dimethylbut-2-en-1-yl)oxy phenyl}hex-4-ynoic acid 63) (3S)-3-(4-{[(2E)-4-methylpenta-2,4-dien-1-yl]oxy}phenyl)hex-4-ynoic acid
64) (3R)-3-(4-{[(2E)-4-methylpenta-2,4-dien-1-yl]oxy}phenyl)hex-4-ynoic acid
65) (3S)-3-{4-[(2R)-2-methylbutoxy]phenyl}hex-4-ynoic acid
66) (3R)-3-{4-[(2R)-2-methylbutoxy]phenyl}hex-4-ynoic acid
67) (3S)-3-{4-[(2S)-2-methylbutoxy]phenyl}hex-4-ynoic acid
68) (3R)-3-{4-[(2S)-2-methylbutoxy]phenyl}hex-4-ynoic acid
69) (3S)-3-{4-[(2R)-2,3-dimethylbutoxy]phenyl}hex-4-ynoic acid
70) (3R)-3-{4-[(2R)-2,3-dimethylbutoxy]phenyl}hex-4-ynoic acid
71) (3S)-3-{4-[(2S)-2,3-dimethylbutoxy]phenyl}hex-4-ynoic acid
72) (3R)-3-{4-[(2S)-2,3-dimethylbutoxy]phenyl}hex-4-ynoic acid
73) (3S)-3-(4-{[(3R)-3-methylpentyl]oxy}phenyl)hex-4-ynoic acid
74) (3R)-3-(4-{[(3R)-3-methylpentyl]oxy}phenyl)hex-4-ynoic acid
75) (3S)-3-(4-{[(3S)-3-methylpentyl]oxy}phenyl)hex-4-ynoic acid
76) (3R)-3-(4-{[(3S)-3-methylpentyl]oxy}phenyl)hex-4-ynoic acid
77) (3S)-3-[4-(4,4,4-trifluorobutoxy)phenyl]hex-4-ynoic acid
78) (3R)-3-[4-(4,4,4-trifluorobutoxy)phenyl]hex-4-ynoic acid
79) (3S)-3-{4-[(5,5,5-trifluoropentyl)oxy]phenyl}hex-4-ynoic acid, and
80) (3R)-3-{4-[(5,5,5-trifluoropentyl)oxy]phenyl}hex-4-ynoic acid.

In a further aspect, the object of the invention is therefore also the compound of formula (I) as defined above according to any of the described embodiments for use as a medicament.

In a further aspect, the object of the invention is therefore also a pharmaceutical composition comprising the compound of formula (I) as defined above according to any of the described embodiments as the active ingredient, in the combination with pharmaceutically acceptable excipients.

The compounds of the formula (I) as defined above can find use in the treatment of GPR40 mediated diseases.

Therefore, the object of the invention is therefore also the compound of formula (I) as defined above according to any of the described embodiments for use in a method of treatment of GPR40 mediated diseases in mammals, including humans.

The object of the invention is also the use of the compound of formula (I) as defined above according to any of the described embodiments for the preparation of a medicament for the treatment of GPR40 mediated diseases in mammals, including humans.

The object of the invention is also the method of treatment of GPR40 mediated diseases in mammals, including humans, which comprises administering of a therapeutically effective amount of the compound of formula (I) as defined above according to any of the described embodiments or a pharmaceutical composition comprising said compound, as defined above.

Compounds of the invention can be prepared using the method outlined in Scheme 1.

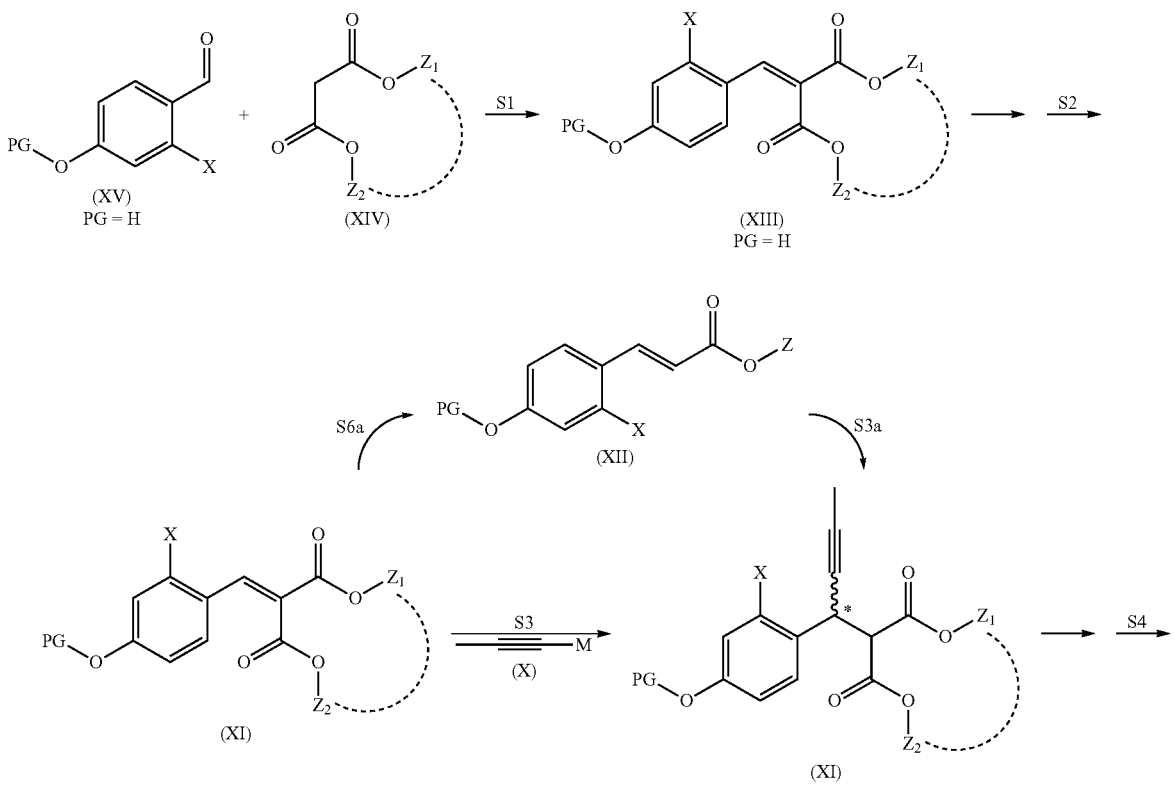

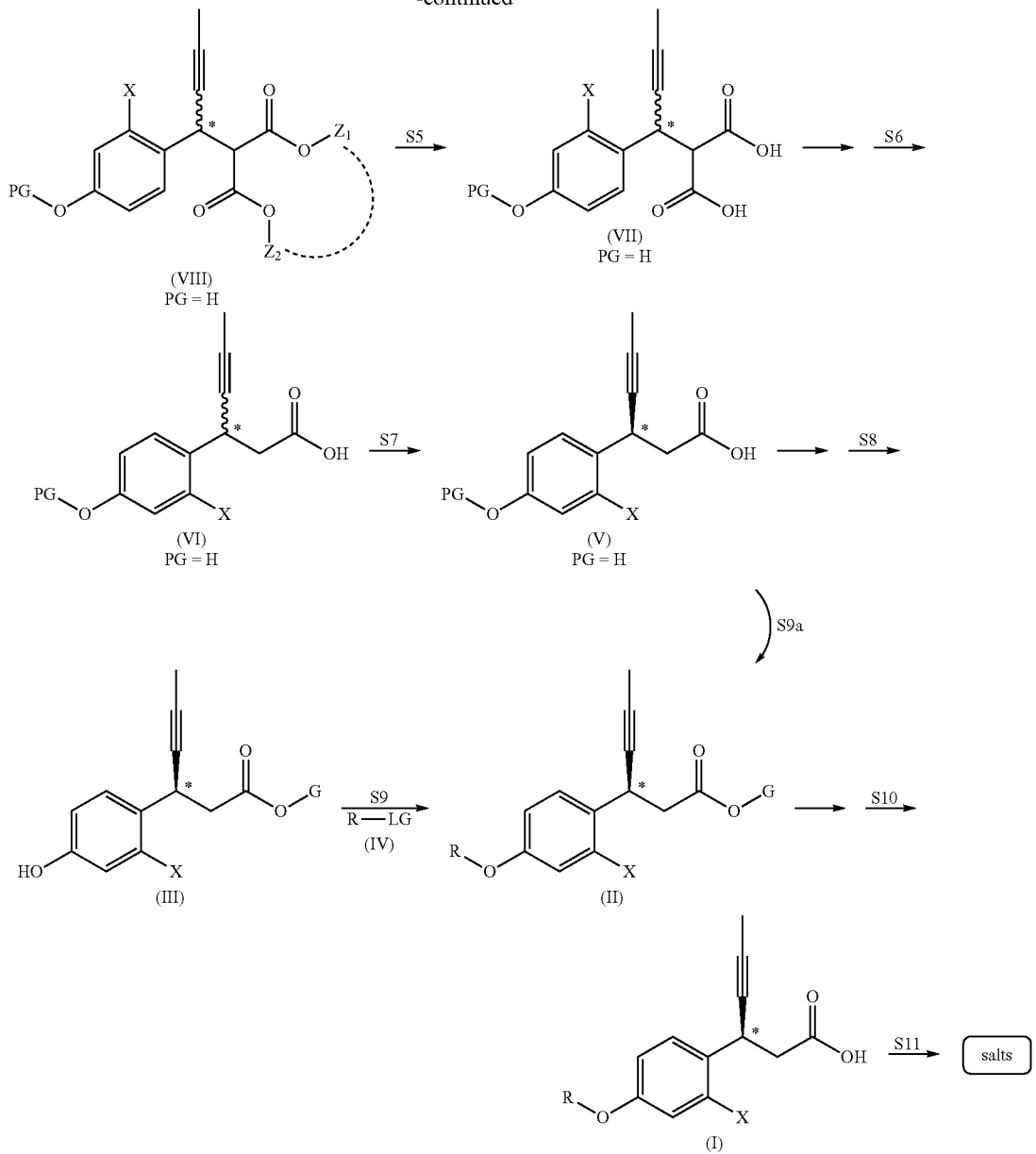

Compound of formula (I) wherein R is as defined above, can be obtained by hydrolysis of ester group in the compound of formula (II), presented as step (S10) in Scheme 1.

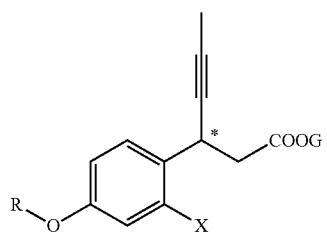

In the compound of formula (I) G, together with oxygen atom to which it is attached, represents synthetically useful alcoholic rest of ester group. Preferred are esters with low molecular weight, for example alkyl groups C1-C4, since they possess low molecular weight and are economically cost-effective, as well as those that due to advantageous physicochemical properties, for example crystallizability, can be applied in the manufacturing process and at the same time facilitate isolation or purification process.

Depending on the applied hydrolysis conditions, the product thereof can be the compound of the formula (I) with free carboxy group or the compound in the form of a salt, for example metal salt. Typically, hydrolysis reaction is carried out in a protic solvent, for example an alcohol, such as methanol, ethanol or iso-propanol, often with the addition of water and other solvents that improve solubility such as for example tetrahydrofuran, acetonitrile, N,N-dimethylformamide, dioxane, in basic environment, in the wide temperature range, depending on the applied solvents, typically at 0 do 100° C. In such environment respective salt of the compound of formula (I) is formed that can be a final form of the compound or can be converted into free acid or can be converted by exchange reaction (presented as step (S11) in Scheme 1 into another salt, for example magnesium or calcium salt. If free acid is obtained, reaction of step (S11) is a process of the preparation of respective salt directly from free acid using any suitable method known from the art. For example, salt of the compound of formula (I) can be obtained directly form free acid after combination with respective amine, hydroxide, hydride, metal salt or metal as such, for example sodium.

The compound of formula (II), wherein G together with oxygen atom through which it is attached represents synthetically useful alcoholic rest of ester group, can be obtained in etherification reaction, presented as step (S9) in Scheme 1, between compound (III) and the compound R-LG (IV), wherein R is defined as above for the compound of the formula (I), and LG is a leaving group. Leaving group can be a halogen atom, for example chlorine, bromine or iodine atom, or also an ester group, such as for example methanesulfonic, p-toluenesulfonic or trifluoromethane-sulfonic group. In such cases reaction is carried out in aprotic organic solvent, such as for example acetone, acetonitrile or dimethylformamide, in the presence of a compound capable to neutralize side acid LG-H that formally is formed in the reaction. Such a compound can be for example potassium carbonate, cesium carbonate, organic amine or metalorganic compound, such as for example n-butyllithium, or also sodium hydride. Leaving group (LG) can be also hydroxy group. In such cases the compound of formula (II) can be efficiently obtained for example under the Mitsunobu reaction conditions. Reactions of the preparation of the compound (II) can be performed in the wide temperature range, depending on the applied solvent; typically from 0 to 100° C. Preferred compound R-LG is therefore respective alcohol or halide, for which R is defined as previously for the compound of formula (I) and LG is hydroxy group or halogen atom, respectively. Furthermore, the compound of formula (II) can be obtained using any other method of synthesis of ethers known from the art. Due to the fact that the same reaction conditions as those used for the preparation of ethers can also be used for the preparation of esters, it is possible to obtain the compound (II) directly from the compound (V), wherein PG represents hydrogen atom, by reaction presented as step (S9a) in Scheme 1. Such a process can be economically advantageous and then substituent G is identical as substituent R.

Reaction presented as step (S8) in Scheme 1 presents a process of the preparation of the compound (III) from the compound (V). It primarily relates to the preparation of an ester wherein G, together with oxygen atom, to which it is attached, is a synthetically useful alcoholic rest of ester group. Especially advantageous are esters with low molecular weight, for example having the chain length C1-C4, because as such they are cost-effective, as well as those that due to advantageous physicochemical properties, for example crystallizability, can be used in the manufacturing process and at the same time facilitate isolation or purification. Compound (III) can be obtained by typical methods of the preparation of ester from free acid, for example directly by equilibrium reaction in the presence of excess of alcohol, preferably with simultaneous removing of water, or using any other method of ester preparation known from the general art and selecting suitable conditions and synthetic equivalents of the above alcohols that would lead to obtaining desired ester. Second aspect of the reaction of step (S8) is obtaining free phenol group in the compound (III). Unless this process, depending on the protecting group PG type used, has taken place earlier, it has to be performed in this step at the latest, since it is necessary for performing the process of step (S9). Preferably, removal of protecting group PG and the process of ester formation can be carried out simultaneously. For example, it is known that tetrahydropyranyl and silyl ethers that can be used in the process as protecting group PG, undergo hydrolysis, for example in methanol under acidic conditions. On the other side, such conditions can be sufficient for formation of methyl ester.

The process in step (S7) relates to the chiral resolution of racemate (VI) and obtaining one of the active optical antipodes, presented by formula (V). This process can be preferably carried out at the stage wherein free carboxy group of the compound (VI) allows to obtain diastereoisomeric salts using optically pure amines, then purification of said salts by fractional crystallization, followed by acidification to obtain compound (V) in the form enriched in desired optical isomer. This is a classic method known from the art. Another method of the preparation of compound (V) is chromatographic resolution with the use of chiral stationary phases. Such resolutions can be performed for both analytical and synthetic purposes. It should be emphasized that to obtain compound (I) the step of resolution into optical antipodes can be performed as an element of synthesis at any of the steps (S4)-(S11), right from the moment of appearance of the chiral carbon atom designated with asterisk (*) in the synthetic process. One can also assume that in accordance with methods known from the art there is a possibility of secondary racemization of the mixture enriched in pharmacologically inactive optical isomer by a suitable chemical or enzymatic reaction and thus increase of the yield of the preparation of desired isomer. In case if both of two optical antipodes would have desired pharmacological activity, optical resolution could be possibly omitted and compound of formula (I) would be used as a racemic mixture, or following enrichment in one of the optical isomers would be used as a mixture of optical isomers having suitable final proportion of isomers that could be controlled by the addition of suitable amount of one of the isomers or a suitable mixture of two isomers in a pre-defined proportion.

The less active optical isomers of the compounds of formula (I) according to the invention are also important due to the fact that at the time of selection of the optimal method of production and the final composition of the active pharmaceutical ingredients, they simultaneously become analytical standards of this process that allow qualitative and quantitative control of optical purity.

Compound (VI) is prepared by reaction of decarboxylation of one of carboxy groups of the compound (VII), presented as step (S6) in Scheme 1. This process usually requires elevated temperature, in the range of 50 to 200° C. and can be carried out in various protic and aprotic organic solvents, with the addition of water, as well as solventless (neat) process. It can be catalyzed by acids or bases and also by the presence of metal salts and reduced pressure.

Step (S5) of the process of the preparation relates to hydrolysis of fragments $Z_1$ and $Z_2$ in compound (VIII) to obtain dicarboxy compound (VII). It can be performed under conditions such as described previously for step (S10).

In the process of step (S4) protecting group PG in the compound (IX) is removed to obtain compound (VIII). Depending on the type of protecting group, it can be carried out under conditions known from the art that are suitable for reactivity of introduced group PG. For example, protic basic conditions are required for removal of ester protection and protic acidic conditions for removal of tetrahydropyranyl protection, while silyl ether protecting group can be removed under protic acidic conditions or in the presence of the source of fluoride anions F⁻. It should be emphasized that the removal of protecting group, depending on the economy of the process of the preparation, can be performed also in any of the following steps from (S4) to (S8), or can be omitted in the case if PG forms with compound (IX) an ether bond and PG is identical with substituent R. In such specific situation, compound (V) can be identical with compound (I) or can formally become such as a result of conversion through the steps (S9a)/(S10)/(S11).

Step (S3) of the preparation of compound (IX) comprises addition of organometallic compound (X) to the compound (XI). This process is a highly exothermic one and requires cooling to the temperature of −76 to +50° C. Due to the instability of the compound (X), step (S3) should be carried out under anhydrous conditions, in aprotic solvent, for example in tetrahydrofuran, advantageously in an inert gas atmosphere, for example argon or nitrogen. Organometallic compound (X) is commercially available as a 1-propynyl-magnesium bromide. It is however possible to use for the preparation of compound (IX) also other types of organo-metallic compounds, for example 1-propynyllithium. Organometallic compound can be prepared earlier and stored as a solution, or can be prepared in situ, just before the reaction. In the reaction of addition of organometallic compound (X) to compound (XI) chiral carbon atom designated with asterisk (*) is formed in the compound (IX). Form this moment it is therefore possible to perform resolution into optical antipodes, as described earlier. It is also possible to prepare compound (IX) by enantioselective addition of organometallic compound (X), whereby a mixture already enriched in desired optical isomer is obtained. Such a process can be performed by intermediate compound (XII) (wherein Z together with oxygen atom represents alcoholic rest of the ester group) which can be obtained by decarboxylation (step S6a), described for example in Mohite, A. R., Mete, T. B., Bhat, R. G., *An Expedient Stereoselective Synthesis of (E)-α,β-Unsaturated Esters and Thioesters Using FeCl3.6H2O, Tetrahedron Letters* (2017), followed by one of the reactions (step S3a) described for example in *PATAI's Chemistry of Functional Groups* in 2009 by John Wiley Et Sons, Ltd. p. 772-800; DOI: 10.1002/9780470682531.pat0416.

Preparation of the compound (XI) from the compound (XIII) comprises step (S2) of the protection of phenol group (PG=H). There is a wide spectrum of protecting groups PG that can be used for this process, such as for example acyl groups (ester), tetrahydropyranyl (acetal protection), silyl ethers or ethers (for example methoxy or ethoxy group), commonly used for the protection of phenolic groups. Since in the compound (I) R together with oxygen atom through which it is attached formally also forms an ether linkage, it can happen that PG in the compound (XI) is identical with R group in the compound (I) and in such a case phenol group deprotection step is not necessary. In other words, fragment R in the compound (I), together with oxygen atom may form the protecting bond already in the step (S2), although it would not belong to typical protecting ether groups, known from the art. Due to the various chemical characters of possible protecting groups, methods of their formation and final recovery of free phenolic functionality differ, albeit are well described in the literature, for example P. J. Kocienski, *Protecting Groups*, 3rd Edition, Hydroxyl Protecting Groups, p. 187. Protecting group PG can be introduced to the preparation route of compound (I) at the present stage or can be already present earlier, for example in compound (XV) as starting material in the reaction of step (S1). Protecting group PG can be deprotected at various synthetic steps of the Scheme 1 of the preparation of compound (I). It is crucial that it is present in intermediate compound (XI), before performing organometallic reaction of step (S3), and removed from compound (V) before performing etherification reaction of step (S9). Therefore, Scheme 1 includes both variants wherein protecting group PG must be present in intermediate compound at the given synthetic step and a variant wherein depending on synthetic convenience it can be removed (PG=H).

Step (S1) relates to the preparation of compound (XIII) from commercially available compounds (XV) and (XIV) by the Knovenagel's condensation reaction known as such in the art. Compound (XV) is an aldehyde wherein X is hydrogen or fluorine atom in the position 2 (ortho). Furthermore, this compound has phenolic function in the position 4 (para —OH) that from the beginning of synthesis can be protected with suitable protecting group (PG) or in this step of synthesis can remain unprotected (PG=H). Compound (XIV) is a classical C—H acid wherein $Z_1$ and $Z_2$ together with oxygen atoms to which they are attached represent alcoholic rests of the formed ester groups. $Z_1$ and $Z_2$ can be the same or different, preferably the same. In particular, $Z_1$ and $Z_2$ can join together to form a cyclic compound. Examples of compound (XIV) are diethyl malonate or Meldrum's acid. Step (S1) can proceed spontaneously or be catalyzed with bases in a suitable protic or aprotic solvent. Since the Knovenagel's reaction can be an equilibrium one, preferred is selection of such solvents that will cause crystallization of the product and thus its purification and simultaneous removal from the equilibrium state.

The process of the preparation of the compound (I) presented in Scheme 1 assumes obtaining one chiral center, designated with asterisk (*). Therefore, compound (I) can be obtained as a racemate, pure enantiomer or mixture of enantiomers. However, in the case of salts preparation which requires more than one compound (I)-derived anion, more than one chirality center will be also present in the final compound of the invention. In such a case, such compound (salt) should be considered as pure diastereoisomer or diastereoisomeric mixture. The same situation may arise if R moiety in compound (I) comprises one or more chiral carbon atoms. The presence of more than one chiral center in compound (I) does not affect, however, the way of its preparation, since in the case of diastereoisomeric mixtures analogous purification methods can be used as for enantiomeric mixtures, as described above.

It should be emphasized that a method for the preparation of compounds of formula (I) is an exemplary manner of carrying out the invention. If economically justified, presented steps may be suitably interchanged or combined with omission of intermediates isolation steps.

The object of the invention is also a pharmaceutical composition, comprising a compound of formula (I) as defined above as an active ingredient, in combination with pharmaceutically acceptable excipients.

If pharmacologically justified and advantageous for therapeutic reasons, the use in the pharmaceutical composition of the present invention of more than one compound of the formula (I) is not excluded.

The compounds of the formula (I) can be administered in the treatment in the form of pharmaceutical composition or pharmaceutical formulation containing them.

In the treatment of diseases mentioned above, the compounds of formula (I) can be administered as a chemical compound, but typically, they will be used as pharmaceutical composition or pharmaceutical formulation containing the compound of the invention or its pharmaceutically acceptable salt, in combination with pharmaceutically acceptable carriers and auxiliary substances.

In the treatment of disorders, diseases, and conditions mentioned above the pharmaceutical composition of the invention can be administered by any suitable route, preferably oral, parenteral or inhalation route and will be in the form of a preparation destined for use in medicine, depending on the intended administration route.

Compositions for oral administration can have the form of solid or liquid preparations. Solid preparations can have, for example, the form of a tablet or capsule produced in a conventional manner from pharmaceutically acceptable inactive excipients such as binders (for example, pregelatinized corn starch, polyvinylpyrrolidone or hydroxypropylmethylcellulose); fillers (for example lactose, saccharose, carboxymethylcellulose, microcrystalline cellulose or calcium hydrogen phosphate); disintegrants (for example crosspovidone, corn starch or sodium starch glycolate); lubricants (for example magnesium stearate, talc or silica), wetting agents (for example sodium laurylsulfate). Tablets can be coated with coatings well known in the art, such as simple coatings, delayed/controlled-release coatings or enteric coatings. Liquid preparations for oral administration can be in the form of, for example, solutions, syrups or suspensions, or can have the form of dry solid product for reconstitution in water or other suitable vehiculum before use. Such liquid preparations can be prepared using conventional means from pharmaceutically acceptable inactive excipients, such as suspending agents (for example sorbitol syrup, cellulose derivatives or hydrogenated edible oils), emulsifiers (for example lecithine or acacia gum), nonaqueous vehicles (for example mandelic oil, oil esters, ethyl alcohol or fractionated vegetable oils), and preservatives (for example methyl or propyl p-hydroxybenzoate or sorbic acid). Preparations can also include suitable buffering agents, flavoring agents, coloring agents and sweeteners.

Preparations for oral administration can be formulated so as to obtain controlled release of the active compound using methods known for a person skilled in the art.

Parenteral route of administration includes administration by intramuscular and intravenous injections, as well as intravenous infusions. Compositions for parenteral administration can, for example, have the form of a unit dosage form, such as ampoules, or multi-dosage containers, with the addition of a preservative. Compositions can have the form such as suspension, solution or emulsion in an oily or aqueous vehiculum, and can include excipients such as suspending agents, stabilizers, and/or dispersing agents. Alternatively, the active ingredient can be formulated as a powder for reconstitution before use in a suitable carrier, for example sterile, pyrogen-free water.

Compositions for administration via inhalation route can have the inhalation form and administered by nebulization. Such preparations include an active compound and auxiliary substance(s) administered as an aerosol, i.e. a system of finely divided small particles of solid or liquid substance suspended in a gas. Auxiliary substances used in nebulization can be for example sodium chloride as an isotonicity agent, inorganic acids and hydroxides as pH regulators and stabilizers, benzalkonium chloride as a preservative, sodium citrate as a buffering agent, polysorbate 80 as a surfactant, ethanol and propylene glycol as a co-solvent, and sulfur compound as anti-oxidants. Preparations for administration by inhalation route can have the form of pressure inhalers or dry powder inhalers.

The method of treatment with the use of the compounds of the present invention will comprise administration of a therapeutically effective amount of the compound of the invention, preferably in the form of a pharmaceutical composition, to the subject in need of such treatment.

Proposed dosage of the compounds of the invention is from 0.1 to about 1000 mg per day, in a single dose or in divided doses. It will be apparent for a person skilled in the art that selection of a dosage required for obtaining desirable biological effect will depend on many factors, for example specific compound, the indication, the manner of administration, the age and condition of a patient and that exact dosage will be ultimately determined by a responsible physician.

EXAMPLES

The examples that follow have the illustrative meaning and present commonly used methods of synthesis of intermediate compounds, used for the preparation of the compounds of the invention, final compounds (of the invention) and reference compounds.

The meaning of abbreviations used in the examples is as follows:

NMR—is the result of nuclear magnetic resonance spectroscopy (δ means the value of chemical shift in ppm). For $^1$H NMR spectra the internal standard was tetramethylsilane (TMS). For $^{13}$C NMR spectra the internal standard was the value of chemical shift of the solvent signal, which for deuterochloroform (CDCl$_3$) is 77.16 ppm, and for hexadeuterodimethylsulfoxide (DMSO-d6) is 39.52 ppm.

MS is the result of mass spectroscopy expressed as m/z ratio. The measurements were performed using electrospray ionization technique (ESI) and ions formed were observed as positive ions (ESI+) or negative ions (ESI−). Symbol M for each compound designates molecular ion, obtained for analyzed molecule without fragmentation.

HPLC means high-performance liquid chromatography.

TLC means thin-layer plate chromatography.

TFA means trifluoroacetic acid.

CD stands for circular dichroism measurement.

Reference Compounds:

Two reference compounds were used: TAK-875 (fasiglifam, Example R1) and AMG-837 (Example R2). TAK-875 is a compound that from among known GPR40 receptor agonists advanced to III phase of clinical trials, therefore is often discussed in the literature and is a good background for comparative experiments. In turn AMG-837 shows the highest similarity of the head fragment structure to the compounds of the invention.

Compound R1: 2[(3S)-6-({3-[4-(3-methanesulfonyl-propoxy)-2,6-dimethylphenyl]-phenyl}methoxy)-2,3-dihydro-1-benzofuran-3-yl]acetic acid (TAK-875, fasiglifam)

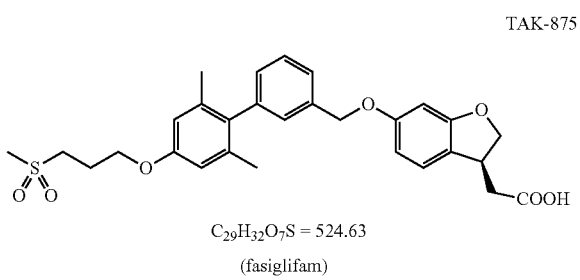 [SMILES: Cc1cc(OCCCS(C)(=O)=O)cc(C)c1-c1cccc(COc2ccc3c(c2)OC[C@H]3CC(=O)O)c1]

TAK-875

$C_{29}H_{32}O_7S = 524.63$ (fasiglifam)

Obtained according to the method described in "*Discovery of TAK-875: A Potent, Selective, and Orally Bioavailable GPR40 Agonist*", ACS Medicinal Chemistry Letters, 2010, 1, p. 290-294. Spectral analysis of the obtained compound was fully consistent with literature data.

$^1$H NMR (300 MHz, CDCl$_3$) δ: 7.50-7.30 (m, 2H), 7.16 (s, 1H), 7.12-6.98 (m, 2H), 6.64 (s, 2H), 6.51-6.46 (m, 2H), 5.06 (s, 2H), 4.76 (t, J=9.1 Hz, 1H), 4.29 (dd, J=9.2, 6.1 Hz, 1H), 4.12 (t, J=5.7 Hz, 2H), 3.90-3.65 (m, 1H), 3.40-3.14 (m, 2H), 2.97 (s, 3H), 2.81 (dd, J=16.9, 5.3 Hz, 1H), 2.61 (dd, J=16.9, 9.3 Hz, 1H), 2.41-2.29 (m, 2H), 1.99 (s, 6H).

$^{13}$C NMR (75 MHz, CDCl$_3$) δ: 177.45, 161.08, 159.95, 157.09, 140.93, 137.63, 137.12, 134.82, 129.16, 128.70, 128.59, 125.65, 124.35, 121.25, 113.21, 107.41, 97.52, 77.50, 70.28, 65.35, 51.85, 40.85, 39.42, 37.52, 22.72, 21.18.

MS (ESI+): m/z=547.2 [M+Na]$^+$. MS (ESI−): m/z=523.1 [M−H]$^−$, 559.1 [M+Cl]$^−$.

Compound R2: (3S)-3-[4-({3-[4-(trifluoromethyl)phenyl]phenyl}methoxy)phenyl]-hex-4-ynoic acid (AMG-837)

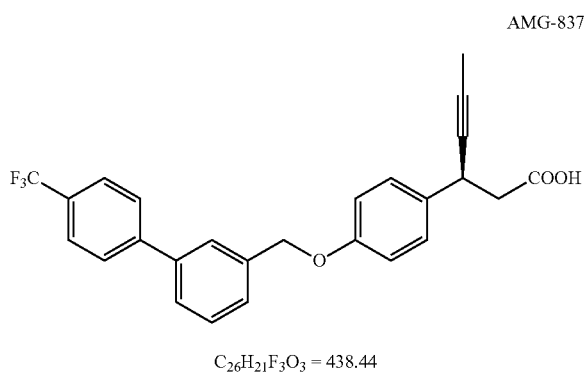 [SMILES: CC#C[C@@H](CC(=O)O)c1ccc(OCc2cccc(-c3ccc(C(F)(F)F)cc3)c2)cc1]

AMG-837

$C_{26}H_{21}F_3O_3 = 438.44$

The compound was obtained as described below in the following Example E1 using (3S)-3-(4-hydroxyphenyl)hex-4-ynoic acid methyl ester (0.733 g, 3.36 mmol, Example I15), 1-[3-(chloromethyl)phenyl]-4-(trifluoromethyl)benzene (1.0 g, 3.69 mmol, Example I1) and other reagents and solvents in suitable proportions and applying to the product of the above procedure (1.4 g) the procedure of Example F1, using other reagents and solvents in suitable proportions. The title compound was obtained as an amorphous solid (1.35 g, total yield 91.8%).

Spectral data were consistent with literature data: James Y. Hamilton, "*Iridium-Catalyzed Enantioselective Allylic Alkynylation*", Angewandte Chemie Int. Ed. Eng. 52 (9) (2013), p. 7532-7535:

$^1$H NMR (300 MHz, CDCl$_3$) δ: 7.68 (s, 4H), 7.65 (s, 1H), 7.55 (dt, J=6.8, 2.2 Hz, 1H), 7.51-7.44 (m, 2H), 7.34-7.28 (m, 2H), 6.98-6.92 (m, 2H), 5.10 (s, 2H), 4.10-4.00 (m, 1H), 2.76 (ddd, J=22.5, 15.7, 7.6 Hz, 2H), 1.83 (d, J=2.4 Hz, 3H).

Intermediate Compounds:

Intermediate compounds for the preparation of the compounds of the invention were prepared as described below.

Intermediate compounds the number of which is preceded by letter I relate to synthetic fragments associated with the synthesis of the head fragment or tail fragment of the compounds of the invention.

Intermediate compounds the number of which is preceded by letter E relate to penultimate ester compounds that are direct precursors of the compounds of the invention.

Example I1: 1-[3-(Chloromethyl)phenyl]-4-(trifluoromethyl)benzene

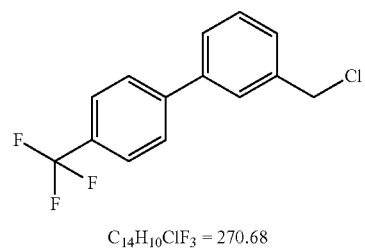 [SMILES: FC(F)(F)c1ccc(-c2cccc(CCl)c2)cc1]

$C_{14}H_{10}ClF_3 = 270.68$

{3-[4-(Trifluoromethyl)phenyl]phenyl}methanol, obtained as described below in Example I2 (1.5 g, 5.95 mmol), was dissolved under argon atmosphere in 10 ml of anhydrous dichloromethane to which 1.29 ml (17.8 mmol) of thionyl chloride were slowly added dropwise while stirring. After stirring overnight, the solvents and the excess of thionyl chloride were distilled off under reduced pressure. After purification by chromatography (silica gel 60, 230-400 mesh, eluent: gradient from n-hexane 100% to n-hexane-dichloromethane 4:1), colorless solid was obtained (1.04 g, yield 65%).

$^1$H NMR (300 MHz, CDCl$_3$) δ: 7.69 (s, 4H), 7.61 (s, 1H), 7.55 (dt, J=7.3, 1.8 Hz, 1H), 7.50-7.40 (m, 2H), 4.65 (s, 2H).

Example I2: {3-[4-(trifluoromethyl)phenyl]phenyl}methanol

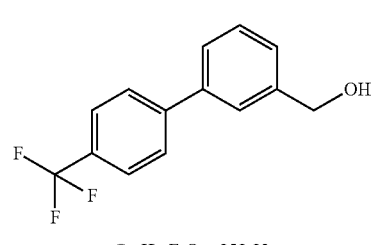

$C_{14}H_{11}F_3O = 252.23$

Obtained according to the method described in J. B. Houze et al., "AMG 837: A potent, orally bioavailable GPR40 agonist", Bioorganic and Medicinal Chemistry Letters. 22 (2012) p. 1267-1270. Spectral data were consistent with literature data, for example WO 2005/118542 A1, example 11, page 50:

$^1$H NMR (300 MHz, CDCl$_3$) δ: 7.68 (s, 4H), 7.60 (s, 1H), 7.51 (dt, J=7.5, 1.6 Hz, 1H), 7.48-7.36 (m, 2H), 4.76 (s, 2H).

Example I3: 5-[(4-hydroxphenyl)methylidene]-2,2-dimethyl-1,3-dioxane-4,6-dione

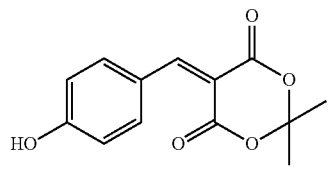

C$_{13}$H$_{12}$O$_5$ = 248.23

Commercially available 4-hydroxybenzaldehyde (500.0 g, 3.89 mol, CAS [128-08-0]) and commercially available 2,2-dimethyl-1,3-dioxane-4,6-dione (700 g, 4.76 mol, CAS [2033-24-1]) were placed in a 10 L reactor, 700 ml toluene and 5.0 L of water were added and the mixture was stirred at 20 to 33° C. for 6 hours. After cooling the reactor to room temperature, intensely yellow solid formed during the reaction was filtered-off, washed with water and dried under vacuum (+50° C., 5 mbar) to constant weight. The completion of the reaction was determined by TLC analysis (heptane-ethyl acetate 3:1) showing no starting material (4-hydroxybenzaldehyde).

Yield: 960 g (97.4%).
Melting point: 192.5-193.4° C. (with decomposition).
$^1$H NMR (300 MHz, DMSO-d$_6$) δ: 10.95 (s, 1H); 8.26 (s, 1H); 8.23-8.13 (m, 2H); 6.97-6.86 (m, 2H); 1.73 (s, 6H).
$^{13}$C NMR (75 MHz, DMSO-d$_6$) δ: 163.67; 163.39; 160.27; 157.03; 137.94; 123.06; 115.84; 109.89; 103.94; 26.87.

Example I4: 5-[(2-fluoro-4-hydroxphenyl)methylidene]-2,2-dimethyl-1,3-dioxane-4,6-dione

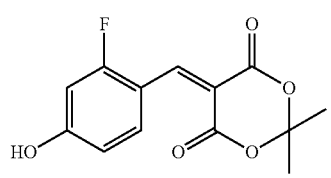

C$_{13}$H$_{11}$FO$_5$ = 266.22

The title product (18.2 g, yield 98%) was obtained in an analogous manner as in Example I3 from commercially available fluoro-4-hydroxybenzaldehyde (10.0 g, 70 mmol, CAS [348-27-6]) and commercially available 2,2-dimethyl-1,3-dioxane-4,6-dione (12.1 g, 82.5 mmol, CAS [2033-24-1]).

$^1$H NMR (300 MHz, DMSO-d$_6$) δ: 11.23 (s, 1H), 8.35 (s, 1H), 8.21 (t, J=8.9 Hz, 1H), 6.73 (ddd, J=15.1, 10.8, 2.4 Hz, 2H), 1.75 (s, 6H).

$^{19}$F NMR (282 MHz, DMSO-d$_6$) δ: −106.10 (dd, J=12.7, 9.0 Hz).
$^{13}$C NMR (75 MHz, DMSO-d$_6$, DEPT 135°) δ: 147.32 (d, J$_{C-F}$=5.9 Hz), 134.68, 112.38, 102.67 (d, J$_{C-F}$=24.6 Hz), 26.87 (s).

Example I5: 5-[1 (R/S)-1-(4-hydroxyphenyl)but-2-yn-1-yl]-2,2-dimethyl-1,3-dioxane-4,6-dione

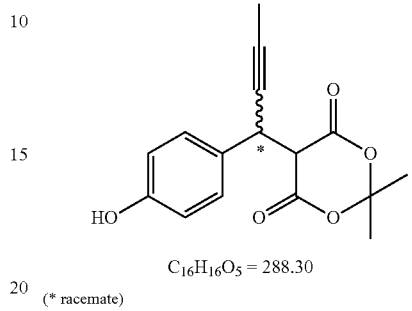

C$_{16}$H$_{16}$O$_5$ = 288.30
(* racemate)

5-[(4-Hydroxyphenyl)methylidene]-2,2-dimethyl-1,3-dioxane-4,6-dione, obtained in Example I3 (2.5 g, 10.1 mmol), was dissolved in dry tetrahydrofuran (40 ml), under argon atmosphere. 4-Methylmorpholine (1.23 g, 12.2 mmol) was added while stirring and cooling to 0° C. and acetyl chloride (0.8 ml, 11.1 mmol) was slowly added dropwise. After 30 minutes of stirring at room temperature, 4-methylmorpholine hydrochloride thus obtained was filtered off and washed with 10 ml of dry tetrahydrofuran. The filtrate thus obtained was cooled to 0° C. and 22.0 ml of commercially available 1-propynylmagnesium bromide (0.5 M solution in tetrahydrofuran, 22.0 ml, 11.0 mmol, CAS [16466-97-0]) was added dropwise under argon atmosphere and the mixture was stirred for 30 minutes at room temperature. Then 20 ml of 2M aqueous sodium hydroxide solution were added and the reaction mixture was heated for further 30 minutes at 60° C. Then the reaction mixture was again cooled to 0° C. and acidified with 10 ml of 5M aqueous hydrochloric acid solution. The product was isolated by the addition of water (50 ml) and extraction with toluene with the addition of ethyl acetate (10% v/v). Organic phase was washed with 1% solution of hydrochloric acid and brine, dried and evaporated. The product was obtained as an amber oil (3.0 g, quantitative yield).

MS (ESI+): m/z=311.1 [M+Na]$^+$. MS (ESI−): m/z=287.1 [M−H]$^−$.

Example I6: 5-[1(R/S)-1-(2-fluoro-4-hydroxyphenyl)but-2-yn-1-yl]-2,2-dimethyl-1,3-dioxane-4,6-dione

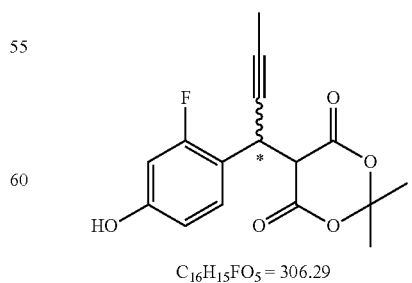

C$_{16}$H$_{15}$FO$_5$ = 306.29
(* racemate)

The title product was obtained in an analogous manner as in Example I5, from 5-[(2-fluoro-4-hydroxyphenyl)methylidene]-2,2-dimethyl-1,3-dioxane-4,6-dione (8.2 g, 30.8 mmol) obtained in Example 14, 4-methylmorpholine (4.6 g, 45.5 mmol), acetyl chloride (3.0 ml, 41.8 mmol), and commercially available propynylmagnesium bromide (0.5 M solution in tetrahydrofuran, 22.0 ml, 11.0 mmol, CAS [16466-97-0]).

MS (ESI+): m/z=329.1 [M+Na]$^+$. MS (ESI−): m/z=305.1 [M−H]$^−$.

Example I7:
(3R/S)-3-(4-hydroxyphenyl)hex-4-ynoic acid

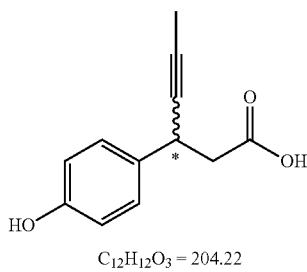

$C_{12}H_{12}O_3 = 204.22$ (* racemate)

5-[1(R/S)-1-(4-Hydroxyphenyl)but-2-yn-1-yl]-2,2-dimethyl-1,3-dioxane-4,6-dione obtained in Example I5 (64.0 g, 222 mmol) was dissolved in N,N'-dimethylformamide (300 ml) and water (30 ml) mixture and heated at 90° C. for 18 hours. During this period decarboxylation process can be observed as carbon dioxide bubbles are released from the solution. Reaction mixture was then cooled, diluted with water (1 L), brine (0.5 L) and acidified with 100 ml of 5% aqueous hydrochloric acid, and the reaction product was isolated with tert-butyl methyl ether (4×0.5 L). Organic phase was separated, washed with brine, dried, and the residue was purified by chromatography (silicagel 60, 230-400 mesh, eluent: heptane-ethyl acetate gradient from 10:1 to 1:3) to obtain 33.2 g of the title compound as a clear syrup (yield 73%).

MS (ESI−): m/z=203.1 [M−H]$^−$, 239.0 [M+Cl]$^−$.

Example I8: (3R/S)-3-(2-Fluoro-4-hydroxyphenyl)hex-4-ynoic acid

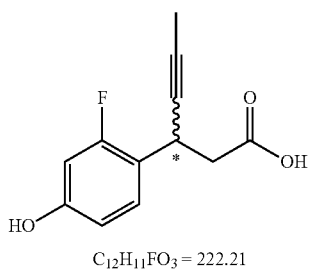

$C_{12}H_{11}FO_3 = 222.21$ (* racemate)

The title product was obtained as a syrup (43 g, yield 99%) in an analogous manner as in Example I7 from 5-[1(R/S)-1-(2-fluoro-4-hydroxyphenyl)but-2-yn-1-yl]-2,2-dimethyl-1,3-dioxane-4,6-dione, obtained in Example 16 (6.0 g, 19.6 mmol).

MS (ESI−): m/z=221.1 [M−H]$^−$, 257.1 [M+Cl]$^−$.

Example I9: (3S)-3-(4-hydroxyphenyl)hex-4-ynoic acid, salt with (1S,2R)-1-amino-2,3-dihydro-1H-inden-2-ol

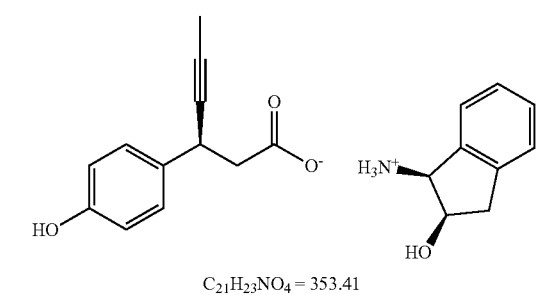

$C_{21}H_{23}NO_4 = 353.41$

Racemic (3R/S)-3-(4-hydroxyphenyl)hex-4-ynoic acid obtained in Example I7 (187.4 g, 0.918 mol) was dissolved in 2.0 L of acetonitrile and commercially available (1S,2R)-(−)-cis-1-aminoindan-2-ol (69.8 g, 0.467 mol, CAS [126456-43-7]) was added while stirring and heating at 70° C. Stirring and heating at the same temperature was continued for further 4 hours, then the suspension of the produced salt was left for cooling to room temperature. After cooling to +5° C., the suspension was filtered and washed with 2×200 ml of cold (0° C.) acetonitrile. The resulting precipitate was flooded with 1.1 L of acetonitrile/water 10:1 mixture and heated to 70° C. with stirring, and then cooled, filtered and washed with cold acetonitrile to obtain crystals with higher optical purity. The last recrystallization operation was repeated twice more, performing the recrystallization consecutively with 0.8 L and 0.6 L of acetonitrile/water 10:1 mixture. Finally, 102.4 g of the salt with >98% diastereomeric excess were obtained as a colorless solid (yield 63%). Optical purity was determined by chiral HPLC (column: Chiralpak Daicel IB-U 100×3.0 mm; 1.6 µm; isocratic phase 92:8 (hexane+0.2% TFA:ethanol+0.2% TFA); the title dominating isomer at Rt=5.67 min (content 99.2%); opposite isomer at Rt=4.94 min (content 0.8%). On the basis of literature data (Shawn D. Walker "*Development of a Scalable Synthesis of a GPR40 Receptor Agonist*", Organic Process Research and Development, 15, (2011), p. 570-580) and activity of the derivatives of this compound with respect to GPR40 receptor in vitro, configuration of the title optical isomer of 3-(4-hydroxyphenyl)hex-4-ynoic acid was determined to be S.

$^1$H NMR (300 MHz, DMSO-d6) δ: 7.45-7.35 (m, 1H), 7.28-7.17 (m, 3H), 7.17-7.06 (m, 2H), 6.73-6.62 (m, 2H), 4.41 (td, J=5.6, 3.2 Hz, 1H), 4.27 (d, J=5.4 Hz, 1H), 3.90 (td, J=7.4, 2.5 Hz, 1H), 3.03 (dd, J=16.2, 5.8 Hz, 1H), 2.84 (dd, J=16.2, 3.1 Hz, 1H), 2.39 (ddd, J=22.0, 14.9, 7.1 Hz, 2H), 1.76 (d, J=2.4 Hz, 3H).

$^{13}$C NMR (75 MHz, DMSO-d6) δ: 174.32, 155.94, 141.28, 140.83, 132.55, 128.16, 128.03, 126.41, 124.90, 114.98 (×2), 82.18, 77.05, 71.30, 57.52, 45.69, 39.07, 33.42, 3.35.

Example I10: (3R)-3-(4-Hydroxyphenyl)hex-4-ynoic acid, salt with (1R,2S)-1-amino-2,3-dihydro-1H-inden-2-ol

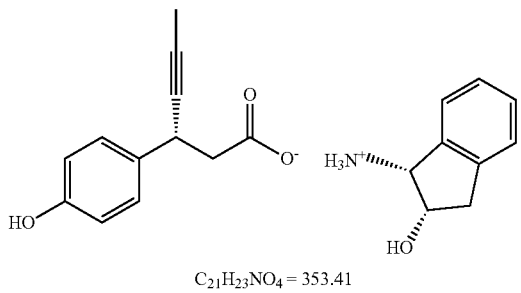

$C_{21}H_{23}NO_4 = 353.41$

The compound was obtained in an analogous manner as in Example I9, using racemic (3R/S)-3-(4-hydroxyphenyl)hex-4-ynoic acid obtained in Example I7 (120.0 g, 0.588 mol), commercially available (1R,2S)-cis-1-aminoindan-2-ol (43.8 g, 0.294 mol, CAS [136030-00-7]) and solvents in proportions corresponding to the amounts of reagents. The title compound was obtained of a colorless solid with optical purity >98% of diastereomeric excess (57.2 g, yield 55%). Since the compounds of Example I9 and Example I10 are mutual isomers, their spectral data are identical. On the same basis configuration of the title optical isomer was determined as isomer R.

Example I11: (3S)-3-(4-hydroxyphenyl)hex-4-ynoic acid

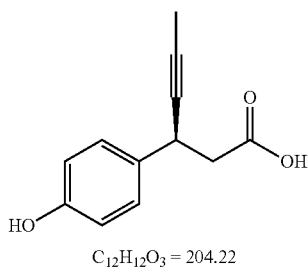

$C_{12}H_{12}O_3 = 204.22$

Salt of (3S)-3-(4-hydroxyphenyl)hex-4-ynoic acid with (1S,2R)-1-amino-2,3-dihydro-1H-inden-2-ol obtained in Example I9 (35.3 g, 0.1 mol) was flooded at room temperature, while stirring, with 200 ml of 1M solution of hydrochloric acid and 100 ml of tert-butyl methyl ether. After 30 minutes, starting salt undergoes dissolution, formed amine hydrochloride remains dissolved in aqueous phase and free acid product passes to organic phase. Aqueous and organic phases were separated. Aqueous phase was additionally extracted with 3×50 ml of tert-butyl methyl ether. Organic phases were combined, washed with brine, dried and concentrated, to obtain quantitatively (20.4 g) the product with spectral data identical as in Example I7. Lack of secondary racemization was confirmed by repeated HPLC analysis on a chiral phase, as in Example I9. Optical purity: >98%.

Example I12: (3R)-3-(4-hydroxyphenyl)hex-4-ynoic acid

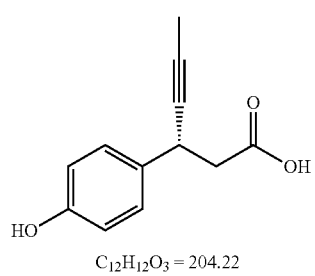

$C_{12}H_{12}O_3 = 204.22$

The title product was obtained quantitatively from (1R,2S)-1-amino-2,3-dihydro-1H-inden-2-ol salt of (3R)-3-(4-hydroxyphenyl)hex-4-ynoic acid obtained in Example I10, using conditions and methods as in Example I11.

Example I13: (3R)-3-(2-fluoro-4-hydroxyphenyl)hex-4-ynoic acid

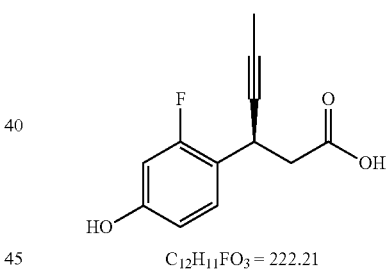

$C_{12}H_{11}FO_3 = 222.21$

Racemic (3R/S)-3-(2-fluoro-4-hydroxphenyl)hex-4-ynoic acid obtained in Example I8 was resolved into optical isomers by HPLC resolution on chiral phase using semi-preparative column Chiralpak Daicel IG 250×30 mm; 5.0 μm and isocratic phase 92:8 (hexane+0.2% TFA:ethanol+0.2% TFA). Control of the resolution was performed using analogous conditions with respect to mobile phase and analytical column Chiralpak Daicel IG-3 250×2.1 mm; 3.0 μm. Retention time for the present isomer was Rt=3.551 min. On the basis of the activity of derivatives of this compound towards GPR40 receptor in vitro, configuration of the present isomer of 3-(4-hydroxyphenyl)hex-4-ynoic acid was determined as isomer R. 50 mg of the compound of optical purity >98% e.e. were obtained, spectral data were identical as for Example I8.

Example I14: (3S)-3-(2-fluoro-4-hydroxyphenyl)hex-4-ynoic acid

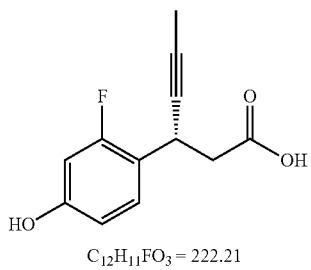

C₁₂H₁₁FO₃ = 222.21

The title product of optical purity >98% e.e. was obtained as in Example I13 in the amount of 45 mg. Retention time for the present isomer Rt=3.118 min (analytical column Chiralpak Daicel IG-3 250×2.1 mm; 3.0 μm, isocratic phase 92:8 (hexane+0.2% TFA:ethanol+0.2% TFA). On the basis of activity of derivatives of this compound towards GPR40 receptor in vitro, configuration of the title isomer of (3S)-3-(2-fluoro-4-hydroxyphenyl)hex-4-ynoic acid was determined as isomer S. Spectral data identical as for Example I8.

Example I15: (3S)-3-(4-hydroxyphenyl)hex-4-ynoic acid methyl ester

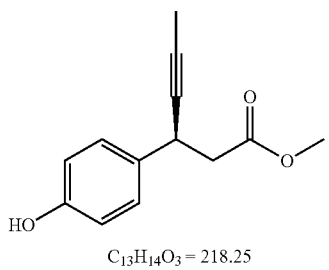 [SMILES: CC#C[C@@H](CC(=O)OC)c1ccc(O)cc1]

C₁₃H₁₄O₃ = 218.25

Salt of (3S)-3-(4-hydroxphenyl)hex-4-ynoic acid with (1S,2R)-1-amino-2,3-dihydro-1H-inden-2-ol obtained in Example I9 (25.1 g, 71 mmol) was flooded with 125 ml of cold (+4° C.) solution of gaseous hydrogen chloride in methanol (58 g of gaseous hydrogen chloride/865 ml of methanol) and stirred for 18 hours at 25° C. During this time all starting material was dissolved. Reaction solution was evaporated until appearance of a white solid that was flooded with 200 ml of tert-butyl methyl ether. Obtained amine hydrochloride precipitate was filtered-off and washed with tert-butyl methyl ether (50 ml) and heptane (50 ml). The filtrate was transferred to separating funnel, washed with water (2×100 ml), 6% aqueous sodium hydrogen carbonate solution and brine, dried and concentrated. The title product was obtained quantitatively (15.5 g) as a light-yellow syrup.

The same product can be obtained using the above conditions and (3S)-3-(4-hydroxyphenyl)hex-4-ynoic acid of Example I11 as a starting material.

$^1$H NMR (300 MHz, CDCl₃) δ: 7.25-7.18 (m, 2H), 6.81-6.73 (m, 2H), 5.73 (s (br), 1H), 4.04 (ddd, J=8.2, 4.9, 2.4 Hz, 1H), 3.67 (s, 3H), 2.71 (qd, J=15.2, 7.7 Hz, 2H), 1.82 (d, J=2.4 Hz, 3H).

$^{13}$C NMR (75 MHz, CDCl₃) δ 172.21, 154.90, 133.12, 128.60, 115.56, 79.70, 79.02, 52.01, 43.58, 33.58, 3.76.
MS (ESI+): m/z=241.1 [M+Na]⁺.

Example I16: (3R)-3-(4-hydroxyphenyl)hex-4-ynoic acid methyl ester

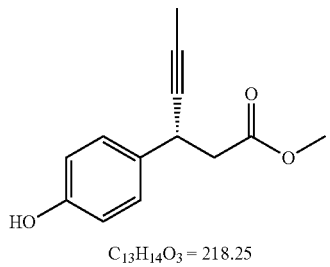 [SMILES: CC#C[C@H](CC(=O)OC)c1ccc(O)cc1]

C₁₃H₁₄O₃ = 218.25

The title product was obtained using salt of (3R)-3-(4-hydroxyphenyl)hex-4-ynoic acid with (1R,2S)-1-amino-2,3-dihydro-1H-inden-2-ol obtained in Example I10 as a starting material and conditions of Example I15. Spectral data were identical with the Example I15.

Example I17: (3R)-3-(2-fluoro-4-hydroxyphenyl)hex-4-ynoic acid methyl ester

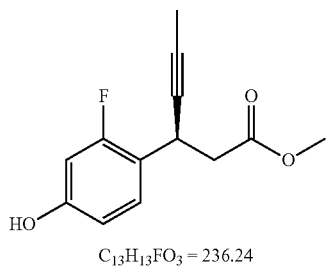

C₁₃H₁₃FO₃ = 236.24

The title product was obtained using (3R)-3-(2-fluoro-4-hydroxyphenyl)hex-4-ynoic acid obtained in Example I13 as a starting material and conditions of Example I15.
MS (ESI+): m/z=259.1 [M+Na]⁺.

Example I18: (3S)-3-(2-fluoro-4-hydroxyphenyl)hex-4-ynoic acid methyl ester

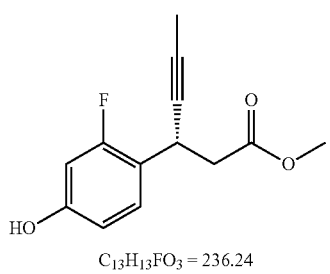

C₁₃H₁₃FO₃ = 236.24

The title product was obtained using (3S)-3-(2-fluoro-4-hydroxyphenyl)hex-4-ynoic acid obtained in Example I14 as a starting material and conditions of Example I15.
MS (ESI+): m/z=259.1 [M+Na]⁺.

Example I19: 2,3-dimethylbut-2-enoic acid ethyl ester

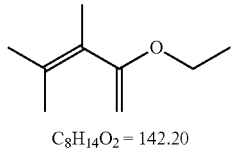

C$_8$H$_{14}$O$_2$ = 142.20

Commercially available triethyl 2-phosphonopropionate (22.5 ml, 103 mmol, CAS [3699-66-9]) was placed in dry tetrahydrofuran (65 ml) under argon atmosphere, cooled to −76° C. and 2.5M solution of n-butyllithium in hexanes (39.2 ml, 98 mmol) was slowly added dropwise under stirring. Colorless solid precipitated and the reaction mixture was left to warm to 0° C. Acetone was added dropwise to the reaction mixture (14.4 ml, 196 mmol) and the contents of the reaction vessel was stirred at room temperature for 24 hours. The reaction product was isolated by the adding of 100 ml of 3% aqueous sulfuric acid solution and extraction with diethyl ether. Organic layer was separated, washed twice with water, 6% aqueous sodium bicarbonate solution and brine, dried and concentrated on evaporator at 30° C. and 400 mbar. The residue was distilled under reduced pressure, collecting fraction of the product that distills in the range 59-62° C. and pressure range 5.3-5.6 mbar, to obtain 11.2 g of a colorless liquid (80% yield).

$^1$H NMR (300 MHz, CDCl$_3$) δ: 4.19 (q, J=7.1 Hz, 2H), 2.00 (d, J=1.3 Hz, 3H), 1.85 (s, 3H), 1.80 (s, 3H), 1.30 (t, J=7.1 Hz, 3H.

$^{13}$C NMR (75 MHz, CDCl$_3$) δ: 169.90, 142.77, 122.76, 60.09, 22.92, 22.45, 15.75, 14.43.

Example I20: 2,3-dimethylbut-2-en-1-ol

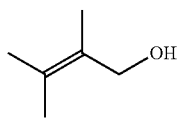

C$_6$H$_{12}$O = 100.16

Lithium aluminum hydride (5.69 g, 142 mmol) was placed under argon atmosphere in 10 ml of dry tetrahydrofuran, and solution of 2,3-dimethylbut-2-enoic acid ethyl ester obtained in Example I19 (18.4 g, 129 mmol) in 30 ml of tetrahydrofuran was slowly added dropwise at such a rate so as to maintain reaction mixture just below boiling point. When addition was completed, the contents of the reaction vessel was stirred for further 10 minutes, and then cooled to 0° C. and the excess of lithium aluminum hydride was decomposed by the addition of 200 ml of tert-butyl methyl ether and gradual addition of ice (10 g). Reaction mixture was diluted with further portion of tert-butyl methyl ether (200 ml) and insoluble aluminum salts were digested by the addition of 0.5 L of 50% aqueous sodium hydroxide solution. Reaction mixture was transferred to separating funnel. Organic phase was separated, washed with 50% aqueous sodium hydroxide solution (100 ml), 6% aqueous potassium bisulfate solution and brine, and dried. The title product was isolated by distillation under reduced pressure to obtain 8.2 g of colorless liquid (yield 63%, boiling point 48-49° C. under pressure of 2.9 mbar).

$^1$H NMR (300 MHz, CDCl$_3$) δ: 4.12 (s, 2H), 1.74 (s, 6H), 1.69 (s, 3H).

$^{13}$C NMR (75 MHz, CDCl$_3$) δ: 129.16, 127.47, 63.89, 20.88, 20.00, 16.60.

Example I21: (2R/S)-2,3-dimethylbutan-1-ol

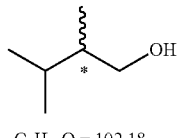

C$_6$H$_{14}$O = 102.18

(* racemate)

Commercially available 2,3-dimethyl-1-butene (6 ml, 4.08 g, 47 mmol, CAS [563-78-0]) was dissolved in dry tetrahydrofuran (10 ml) and 100 ml of 0.5 tetrahydrofuran solution of 9-borabicyclo[3.3.1]nonane (9-BBN, 50 mmol) were added while stirring and cooling to 0° C. Then the contents of the reaction vessel was stirred at room temperature for 2.5 hours. Reaction mixture was again cooled to 0° C. and 60 ml of 3M aqueous sodium hydroxide solution and 60 ml of 30% aqueous hydrogen peroxide solution were carefully added dropwise. Stirring was continued for further 1.5 hour at room temperature. Reaction product was isolated by extraction with diethyl ether (100 ml). Organic phase was separated, washed with 5% aqueous sodium sulfite solution and brine, dried and concentrated at 40° C. and 100 mbar pressure. The residue was distilled under reduced pressure to provide 2.0 g (42% yield) of the title product in the form of a colorless liquid collected as a fraction distilling at 50° C. under 3 mbar pressure.

$^1$H NMR (300 MHz, CDCl$_3$) δ: 3.59 (dd, J=10.6, 5.9 Hz, 1H), 3.44 (dd, J=10.6, 7.0 Hz, 1H), 1.70 (dtd, J=13.7, 6.8, 5.1 Hz, 1H), 1.59-1.42 (m, 1H), 0.92 (d, J=6.8 Hz, 3H), 0.86 (d, J=7.0 Hz, 3H), 0.84 (d, J=7.0 Hz, 3H).

$^{13}$C NMR (75 MHz, CDCl$_3$) δ: 66.64, 41.56, 28.99, 20.73, 18.12, 12.65.

Example I22: 1-Bromo-4-(2,2-dimethylpropoxy)benzene

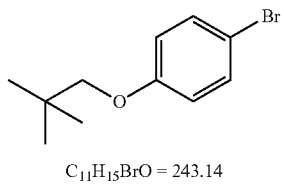

C$_{11}$H$_{15}$BrO = 243.14

Neopentyl alcohol (2,2-dimethyl-1-propanol, 2.93 ml, 27 mmol) was dissolved in 50 ml of dry N,N'-dimethylformamide. The solution was cooled to 0° C. and triethylamine (3.78 ml, 27 mmol) was added while stirring, followed by slow, dropwise addition of methanesulfonyl chloride (1.94 ml, 25 mmol). After formation of triethylamine hydrochloride precipitate, the contents of the reaction vessel were stirred for further 30 minutes without cooling, and subsequently commercially available 4-bromophenol (3.53 g, 20 mmol, CAS [106-41-2]), tetrabutylammonium iodide (0.923 g, 2.5 mmol) and cesium carbonate (18.5 g, 56.2 mmol) were added and the reaction mixture was heated to 80° C. with simultaneous blowing with argon for 15 minutes. Then temperature of the reaction mixture was raised to 130° C. and stirring was continued for 18 hours. After cooling, reaction product was isolated by the addition of water (150 ml) and extraction with diethyl ether. Organic phase was separated, washed with water (2×50 ml) and brine (50 ml), dried, concentrated and purified by chromatography (silica gel 60, 230-400 mesh, eluent: heptane-ethyl acetate gradient from 20:1 to 8:1). The title compound was obtained as a colorless oil (3.66 g, 75% yield).

$^1$H NMR (300 MHz, CDCl$_3$) δ: 7.37-7.30 (m, 2H), 6.79-6.72 (m, 2H), 3.53 (s, 2H), 1.01 (s, 9H).

$^{13}$C NMR (75 MHz, CDCl$_3$) δ: 158.86, 132.26, 116.46, 112.58, 78.27, 32.03, 26.71.

Example I23: 4-(2,2-dimethylpropoxy)benzaldehyde

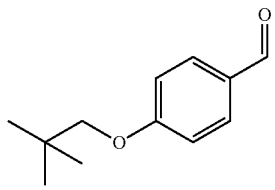

$C_{12}H_{16}O_2 = 192.25$

1-Bromo-4-(2,2-dimethylpropoxy)benzene obtained in Example I22 (4.54 g, 18.7 mmol) was dissolved under argon atmosphere in 15 ml of dry tetrahydrofuran and cooled to 0° C. At this temperature 1.3M tetrahydrofuran solution of iso-propylmagnesium chloride-lithium chloride complex (1.64 ml, 6.91 mmol) was added and after 20 minutes 2.5M n-butyllithium solution in hexanes (1.7 ml, 13.8 mmol). Stirring was continued at the same temperature for 1 hour. Subsequently, 4 ml of dry N,N'-dimethylformamide were added and stirring was continued at the same temperature for further one hour. Reaction was quenched by adding water (50 ml). Reaction product was isolated by extraction with ethyl acetate/diethyl ether 1:1 mixture. Organic phase was separated, washed with water (2×50 ml) and brine (50 ml), dried, concentrated and purified by chromatography (silica gel 60, 230-400 mesh, eluent: heptane-ethyl acetate gradient from 20:1 to 4:1). The title compound was obtained as a colorless oil (3.40 g, 95% yield).

$^1$H NMR (300 MHz, CDCl$_3$) δ: 9.87 (s, 1H), 7.86-7.78 (m, 2H), 7.05-6.96 (m, 2H), 3.67 (s, 2H), 1.05 (s, 9H).

$^{13}$C NMR (75 MHz, CDCl$_3$) δ: 190.75, 164.66, 131.97, 129.81, 114.83, 78.19, 31.91, 26.55.

Example I24: 2-{[4-(2,2-dimethylpropoxy)phenyl]methylidene}propane-1,3-dioic acid dimethyl ester

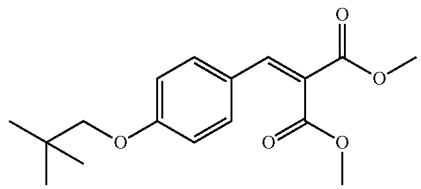

$C_{17}H_{22}O_5 = 306.35$ 4-(2,2-dimethylpropoxy)benzaldehyde (3.59 g, 18.7 mmol) obtained in Example I23 was dissolved in benzene (25 ml), diethyl malonate (2.24 ml, 19.6 mmol), piperidine (0.184 ml, 1.87 mmol) and acetic acid (0.101 ml, 1.77 mmol) were added and the whole was refluxed while stirring with simultaneous removal of water formed in the reaction (Dean-Stark trap) for 18 hours. Subsequently, reaction mixture was evaporated and purified by chromatography (silica gel 60, 230-400 mesh, eluent: heptane-ethyl acetate gradient from 20:1 to 4:1). The title product was obtained as a colorless oil (1.86 g, 31% yield).

$^1$H NMR (300 MHz, CDCl$_3$) δ: 7.71 (s, 1H), 7.40-7.34 (m, 2H), 6.92-6.86 (m, 2H), 3.86 (s, 3H), 3.83 (s, 3H), 3.61 (s, 2H), 1.03 (s, 9H).

$^{13}$C NMR (75 MHz, CDCl$_3$) δ: 167.70, 164.93, 161.85, 142.81, 131.60, 125.10, 122.67, 114.99, 78.05, 52.63, 52.53, 31.93, 26.61.

Example I25: 2-[(1R/S)-1-[4-(2,2-dimethylpropoxy)phenyl]but-2-yn-1-yl]propane-1,3-dioic acid dimethyl ester

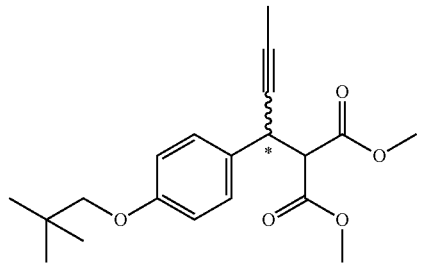

$C_{20}H_{26}O_5 = 346.42$ (* racemate)

The title product was prepared starting from 2-{[4-(2,2-dimethylpropoxy)phenyl]-methylidene}propane-1,3-dioic acid dimethyl ester obtained in Example I24 (830 mg, 2.71 mmol) under conditions as in Example I5, with the exception that first acylation step was omitted, and other reagents in the amounts proportional to the starting compound. Yield 850 mg (91%).

MS (ESI+): m/z=715.3 [2M+Na]$^+$.

Example I26: 2-[(1R/S)-1-[4-(2,2-dimethylpropoxy)phenyl]but-2-yn-1-yl]propanedioic acid

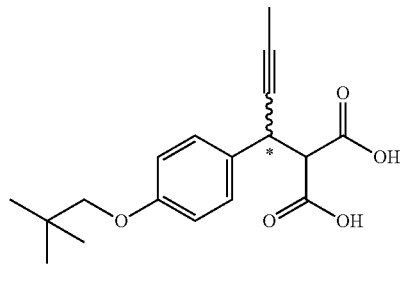

C₁₈H₂₂O₅ = 318.36

(* racemate)

2-[(1R/S)-1-[4-(2,2-Dimethylpropoxy)phenyl]but-2-yn-1-yl]propane-1,3-dioic acid dimethyl ester obtained in Example I25 (850 mg, 2.45 mmol) was dissolved in tetrahydrofuran (20 ml) and methanol (10 ml) mixture, solution of 1.03 g (24.5 mmol) of lithium hydroxide monohydrate in 10 ml of water was added, and the contents of reaction vessel was stirred at 25° C. for 18 hours. Formation of the product was monitored by TLC (100% ethyl acetate: starting compound (Rf=0.8) disappears and new product of substantially higher polarity is formed (Rf=0.05)). The reaction product was isolated after acidification of the reaction mixture with 3% aqueous solution of sulfuric acid and exhaustive extraction with ethyl acetate with the addition of 5 vol. % of methanol. The combined organic phases were washed with brine, dried and concentrated. Raw product (730 mg, yield 94%) obtained as a yellow oil was used for the next reaction step without purification.

Example I27: 2(E)-4-methylpenta-2,4-dienoic acid methyl ester

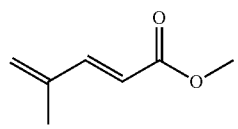

C₇H₁₀O₂ = 126.15

Methacrolein (6.81 g, 87.4 mmol, CAS [78-79-5]) and (triphenylphosphoranylidene)-acetic acid methyl ester (50.0 g, 147 mmol, CAS [2605-67-6]) were stirred and heated at 60° C. for 24 hours in dry tetrahydrofuran under argon atmosphere. Subsequently half of the tetrahydrofuran volume (100 ml) was evaporated under reduced pressure and replaced with 200 ml of n-hexane. Solid by-products of the reaction were filtered and washed with 50 ml of n-hexane containing 5% (v/v) of ethyl acetate. Filtrate was concentrated to the oil at 40° C./150 mbar and then distilled at the temperature range of 65-70° C. and pressure range 8-7 mbar. The product was obtained in the form of colorless oil in the amount of 8.66 g (68.6% yield).

1H NMR (300 MHz, CDCl₃) δ: 7.37 (dd, J=15.8, 0.5 Hz, 1H), 5.88 (d, J=15.8 Hz, 1H), 5.35 (ddd, J=5.0, 2.4, 1.2 Hz, 2H), 3.76 (s, 3H), 1.89 (dd, J=1.4, 0.8 Hz, 3H).

13C NMR (75 MHz, CDCl₃) δ: 167.59, 147.29, 140.59, 124.38, 118.42, 51.59, 18.09.

Example I28: 2(E)-4-methylpenta-2,4-dien-1-ol

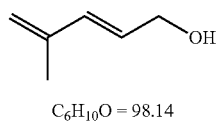

C₆H₁₀O = 98.14

2(E)-4-Methylpenta-2,4-dienoic acid methyl ester obtained in Example I27 (2.89 g, 22.9 mmol) was dissolved under argon atmosphere in 70 ml of dry dichloromethane and 71 ml of 1M di-iso-butyl aluminum hydride solution in hexanes (71.0 mmol, CAS [1191-15-7]) were added dropwise at −78° C. while stirring. Reaction mixture was kept at these conditions for 3 hours. After this time TLC (heptane/ethyl acetate 5:1) showed complete disappearance of the starting compound. Reaction product was isolated by extraction with diethyl ether. Organic phase after drying and concentration was purified by chromatography (silica gel 60 230-400 mesh, eluent: heptane-ethyl acetate gradient from 20:1 to 4:1). The title product was obtained as a colorless liquid (2.1 g, 93% yield).

1H NMR (300 MHz, CDCl₃) δ: 6.43-6.25 (m, 1H), 5.90-5.72 (m, 1H), 5.06-4.93 (m, 2H), 4.28-4.17 (m, 2H), 1.87-1.84 (m, 3H).

13C NMR (75 MHz, CDCl₃) δ: 141.48, 134.20, 128.56, 116.91, 63.64, 18.65.

Example E1: (3S)-3-(4-Propoxyphenyl)hex-4-ynoic acid methyl ester

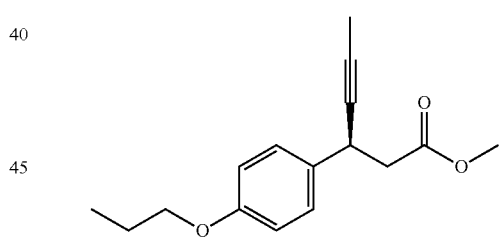

C₁₆H₂₀O₃ = 260.33

(3S)-3-(4-Hydroxphenyl)hex-4-ynoic acid methyl ester obtained in Example I15 (125 mg, 0.573 mmol) and commercially available 1-bromopropane (0.52 ml, 5.73 mmol, CAS [106-94-5]) were dissolved in dry N,N'-dimethylformamide (10 ml), cesium carbonate (377 mg, 1.15 mmol) was added and the whole was stirred at 50° C. for 18 hours. Reaction was quenched by adding water (50 ml). Product was extracted with diethyl ether and ethyl acetate 1:1 mixture (50 ml). Organic phase was washed with 3% aqueous sulfuric acid solution, water and brine, dried and concentrated. Product was purified by chromatography (silica gel 60, 230-400 mesh, eluent:heptane-ethyl acetate gradient from 100:1 to 20:1). The title product was obtained as a colorless syrup (130 mg, yield 87%).

¹H NMR (300 MHz, CDCl₃) δ: 7.32-7.21 (m, 2H), 6.90-6.77 (m, 2H), 4.11-3.99 (m, 1H), 3.89 (t, J=6.0 Hz, 2H), 3.66 (s, 3H), 2.82-2.58 (m, 2H), 1.82 (d, J=2.4 Hz, 3H), 1.85-1.72 (m, 2H), 1.02 (t, J=7.4 Hz, 3H).

$^{13}$C NMR (75 MHz, CDCl$_3$) δ: 171.66, 158.30, 133.12, 128.36, 114.67, 79.82, 78.78, 69.63, 51.74, 43.53, 33.57, 22.70, 10.61, 3.72.

MS (ESI+): m/z=283.1 [M+Na]$^+$, 299.1 [M+K]$^+$.

Example E2: (3S)-3-[4-(hexyloxy)phenyl]hex-4-ynoic acid methyl ester

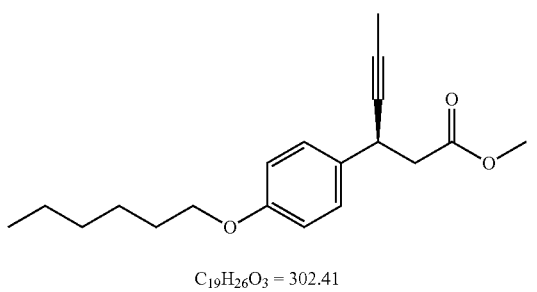 [SMILES: CC#C[C@@H](CC(=O)OC)c1ccc(OCCCCCC)cc1]

C$_{19}$H$_{26}$O$_3$ = 302.41

The title product was obtained as a colorless syrup (132 mg, 76% yield) under conditions as described in Example E1 starting from (3S)-3-(4-hydroxyphenyl)hex-4-ynoic acid methyl ester (125 mg, 0.573 mmol, Example I15), commercially available 1-bromohexane (0.82 ml, 5.73 mmol, CAS [111-25-1]) and other reagents and solvents in suitable proportions.

$^1$H NMR (300 MHz, CDCl$_3$) δ: 7.31-7.22 (m, 2H), 6.89-6.77 (m, 2H), 4.05 (ddq, J=9.3, 7.2, 2.3 Hz, 1H), 3.92 (t, J=6.6 Hz, 2H), 3.65 (s, 3H), 2.70 (qd, J=15.2, 7.7 Hz, 2H), 1.82 (d, J=2.4 Hz, 3H), 1.80-1.71 (m, 2H), 1.52-1.38 (m, 2H), 1.38-1.24 (m, 4H), 0.90 (t, J=7.0 Hz, 3H).

$^{13}$C NMR (75 MHz, CDCl$_3$) δ: 171.67, 158.32, 133.11, 128.36, 114.68, 79.83, 78.78, 68.14, 51.74, 43.54, 33.58, 31.70, 29.38, 25.85, 22.71, 14.12, 3.73.

MS (ESI+): m/z=325.2 [M+Na]$^+$, 341.1 [M+K]$^+$.

Example E3: (3S)-3-[4-(heptyloxy)phenyl]hex-4-ynoic acid methyl ester

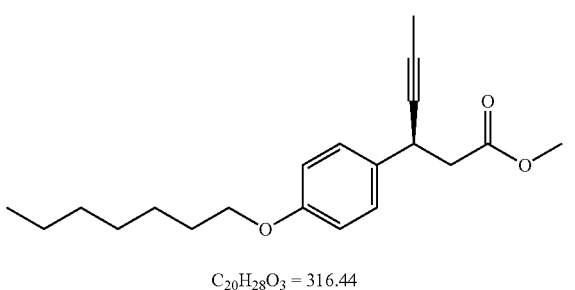 [SMILES: CC#C[C@@H](CC(=O)OC)c1ccc(OCCCCCCC)cc1]

C$_{20}$H$_{28}$O$_3$ = 316.44

The title product was obtained as a colorless syrup (153 mg, 84% yield) under conditions as described in Example E1 starting from (3S)-3-(4-hydroxyphenyl)hex-4-ynoic acid methyl ester (125 mg, 0.573 mmol, Example I15), commercially available 1-bromoheptane (0.9 ml, 5.73 mmol, CAS [629-04-9]) and other reagents and solvents in suitable proportions.

$^1$H NMR (300 MHz, CDCl$_3$) δ: 7.31-7.23 (m, 2H), 6.87-6.79 (m, 2H), 4.05 (ddq, J=9.4, 4.8, 2.4 Hz, 1H), 3.92 (t, J=6.6 Hz, 2H), 3.65 (s, 3H), 2.70 (qd, J=15.2, 7.7 Hz, 2H), 1.82 (d, J=2.4 Hz, 3H), 1.87-1.69 (m, 2H), 1.52-1.22 (m, 8H), 0.89 (t, J=6.0 Hz, 3H).

$^3$C NMR (75 MHz, CDCl$_3$) δ: 171.65, 158.31, 133.09, 128.35, 114.66, 79.82, 78.76, 68.12, 51.72, 43.53, 33.57, 31.89, 29.40, 29.16, 26.12, 22.70, 14.15, 3.71.

MS (ESI+): m/z=317.2 [M+H]$^+$, 339.2 [M+Na]$^+$, 355.2 [M+K]$^+$.

Example E4: (3S)-3-[4-(3-methylbutoxy)phenyl]hex-4-ynoic acid methyl ester

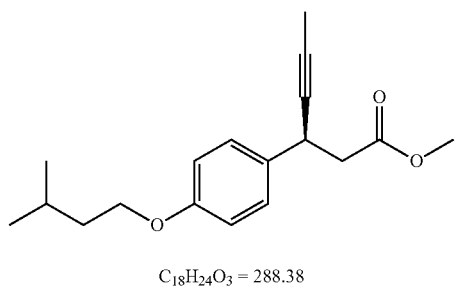 [SMILES: CC#C[C@@H](CC(=O)OC)c1ccc(OCC=C(C)C)cc1]

C$_{18}$H$_{24}$O$_3$ = 288.38

The title product was obtained as a syrup (2.47 g, 91% yield) under conditions as described in Example E1 starting from (3S)-3-(4-hydroxyphenyl)hex-4-ynoic acid methyl ester (2.05 g, 9.39 mmol, Example I15), commercially available 1-bromo-3-methylbutane (0.9 ml, 5.73 mmol, CAS [107-82-4]) and other reagents and solvents in suitable proportions.

MS (ESI+): m/z=311.2 [M+Na]$^+$.

Example E5: (3S)-3-{4-[(3-methylbut-2-en-1-yl)oxy]phenyl}hex-4-ynoic acid methyl ester

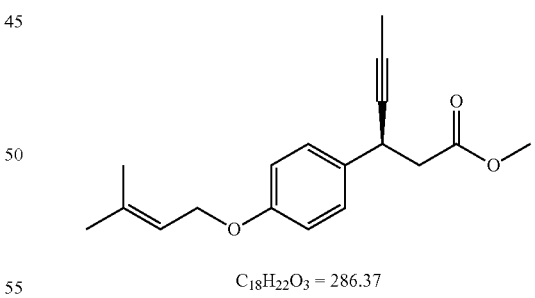

C$_{18}$H$_{22}$O$_3$ = 286.37

The title product was obtained as a syrup (3.93 g, 99% yield) under conditions as described in Example E1 starting from (3S)-3-(4-hydroxyphenyl)hex-4-ynoic acid methyl ester (3.03 g, 13.9 mmol, Example I15), commercially available 1-bromo-3-methyl-2-butene (2.25 ml, 19.4 mmol, CAS [870-63-3]) and other reagents and solvents in suitable proportions.

MS (ESI+): m/z=309.1 [M+Na]$^+$, 325.1 [M+K]$^+$.

Example E6: (3R)-3-{4-[(3-methylbut-2-en-1-yl)oxy]phenyl}hex-4-ynoic acid methyl ester

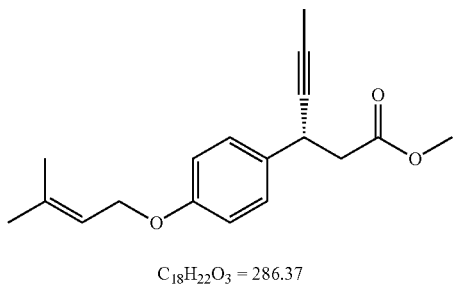 [SMILES: CC#C[C@H](CC(=O)OC)c1ccc(OCC=C(C)C)cc1]

C₁₈H₂₂O₃ = 286.37

The title product was obtained as a syrup (0.331 g, 83% yield) under conditions as described in Example E1 starting from (3R)-3-(4-hydroxyphenyl)hex-4-ynoic acid methyl ester (0.303 g, 13.9 mmol, Example I16), commercially available 1-bromo-3-methyl-2-butene (0.225 ml, 1.94 mmol, CAS [870-63-3]) and other reagents and solvents in suitable proportions.

MS (ESI+): m/z=309.1 [M+Na]⁺, 325.1 [M+K]⁺.

Example E7: (3R)-3-{2-fluoro-4-[(3-methylbut-2-en-1-yl)oxy]phenyl}hex-4-ynoic acid methyl ester

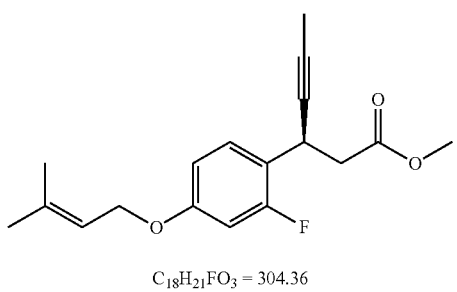 [SMILES: CC#C[C@@H](CC(=O)OC)c1ccc(OCC=C(C)C)cc1F]

C₁₈H₂₁FO₃ = 304.36

The title product was obtained as a syrup (32 mg, 49% yield) under conditions as described in Example E1 starting from (3R)-3-(2-fluoro-4-hydroxphenyl)hex-4-ynoic acid methyl ester (50 mg, 0.212 mmol, Example I17), commercially available 1-bromo-3-methyl-2-butene (0.25 ml, 2.2 mmol, CAS [870-63-3]) and other reagents and solvents in suitable proportions.

MS (ESI+): m/z=327.1 [M+Na]⁺.

Example E8: (3S)-3-{2-fluoro-4-[(3-methylbut-2-en-1-yl)oxy]phenyl}hex-4-ynoic acid methyl ester

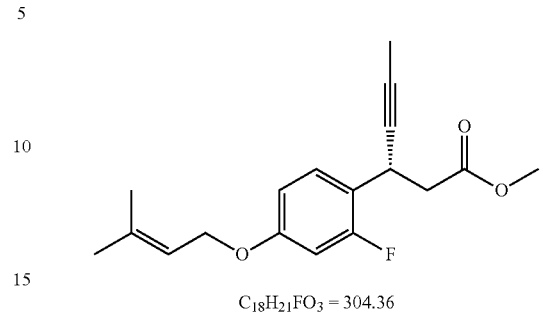

C₁₈H₂₁FO₃ = 304.36

The title product was obtained as a syrup (44 mg, 76% yield) under conditions as described in Example E1 starting from (3S)-3-(2-fluoro-4-hydroxyphenyl)hex-4-ynoic acid methyl ester (45 mg, 0.191 mmol, Example I18), commercially available 1-bromo-3-methyl-2-butene (0.25 ml, 2.2 mmol, CAS [870-63-3]) and other reagents and solvents in suitable proportions.

MS (ESI+): m/z=327.1 [M+Na]⁺.

Example E9: (3S)-3-[4-(2-ethylbutoxy)phenyl]hex-4-ynoic acid methyl ester

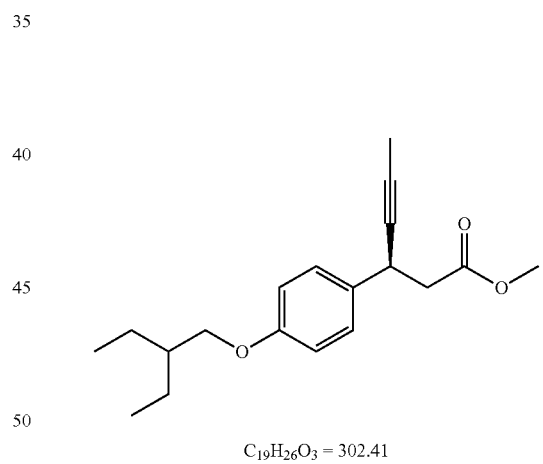

C₁₉H₂₆O₃ = 302.41

The title product was obtained as an oil (0.37 g, 89% yield) under conditions as described in Example E1 starting from (3S)-3-(4-hydroxyphenyl)hex-4-ynoic acid methyl ester (0.30 g, 1.37 mmol, Example I15), commercially available 1-bromo-2-ethylbutane (0.397 ml, 1.94 mmol, CAS [3814-34-4]) and other reagents and solvents in suitable proportions.

MS (ESI+): m/z=325.2 [M+Na]⁺.

Example E10: (3S)-3-[4-(4,4,4-trifluorobutoxy)phenyl]hex-4-ynoic acid methyl ester

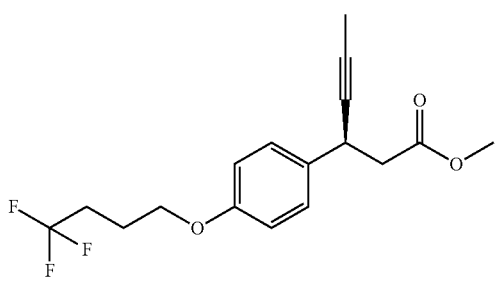

C₁₇H₁₉F₃O₃ = 328.33

The title product was obtained as an oil (451 mg, 100% yield) under conditions as described in Example E1 starting from (3S)-3-(4-hydroxphenyl)hex-4-ynoic acid methyl ester (300 mg, 1.37 mmol, Example I15), commercially available 1-bromo-4,4,4-trifluorobutane (0.431 ml, 3.44 mmol, CAS [406-81-5]) and other reagents and solvents in suitable proportions.

MS (ESI+): m/z=351.1 [M+Na]⁺.

Example E11: (3S)-3-{4-[(5,5,5-trifluoropentyl)oxy]phenyl}hex-4-ynoic acid methyl ester

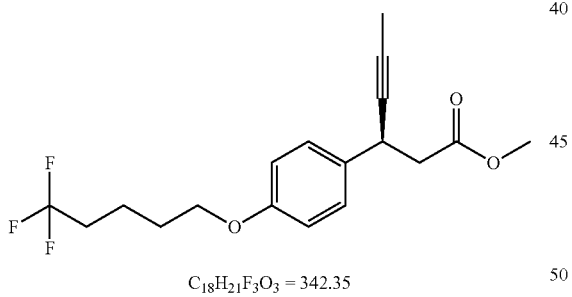

C₁₈H₂₁F₃O₃ = 342.35

The title product was obtained as an oil (470 mg, 100% yield) under conditions as described in Example E1 starting from (3S)-3-(4-hydroxyphenyl)hex-4-ynoic acid methyl ester (300 mg, 1.37 mmol, Example I15), commercially available 5-bromo-1,1,1-trifluoropentane (0.488 ml, 3.44 mmol, CAS [54932-74-0]) and other reagents and solvents in suitable proportions.

MS (ESI+): m/z=365.1 [M+Na]⁺.

Example E12: (3S)-3-[4-(2-methylpropoxy)phenyl]hex-4-ynoic acid methyl ester

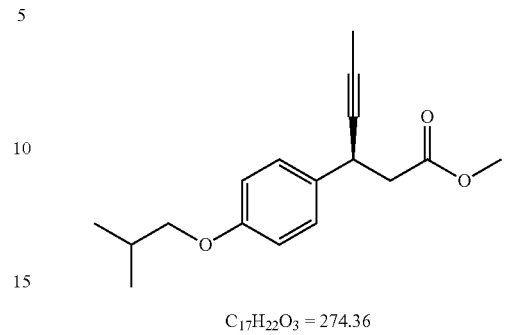

C₁₇H₂₂O₃ = 274.36

The title product was obtained as an oil (460 mg, 92% yield) under conditions as described in Example E1 starting from (3S)-3-(4-hydroxyphenyl)hex-4-ynoic acid methyl ester (400 mg, 1.83 mmol, Example I15), commercially available 1-bromo-2-methylpropane (1.01 g, 7.36 mmol, CAS [78-77-3]) and other reagents and solvents in suitable proportions.

$^1$H NMR (300 MHz, CDCl₃) δ: 7.30-7.22 (m, 2H), 6.87-6.79 (m, 2H), 4.09-4.00 (m, 1H), 3.69 (d, J=6.5 Hz, 2H), 3.66 (s, 3H), 2.70 (qd, J=15.2, 7.7 Hz, 2H), 2.14-1.99 (m, 1H), 1.82 (d, J=2.4 Hz, 3H), 1.01 (d, J=6.7 Hz, 6H).
$^{13}$C NMR (75 MHz, CDCl₃) δ: 171.70, 158.45, 133.11, 131.02, 128.36, 114.72, 79.84, 78.79, 74.61, 51.76, 43.54, 33.59, 28.39, 19.37, 3.73.

MS (ESI+): m/z=297.1 [M+Na]⁺.

Example E13: (3S)-3-{4-[(2R/S)-2-methylbutoxy]phenyl}hex-4-ynoic acid methyl ester

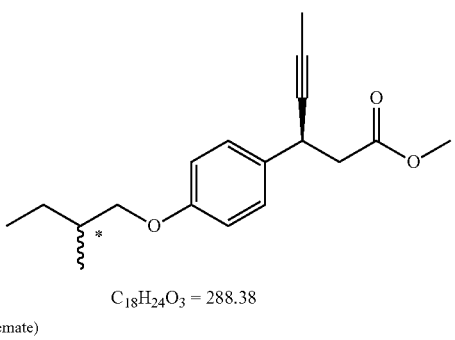

C₁₈H₂₄O₃ = 288.38

(* racemate)

(3S)-3-(4-Hydroxphenyl)hex-4-ynoic acid methyl ester obtained in Example I15 (300 mg, 1.37 mmol) was dissolved under argon atmosphere in 10 ml of dry tetrahydrofuran, triphenylphosphine (728 mg, 2.75 mmol) and commercially available 2-methyl-1-butanol (0.754 ml, 6.87 mmol, CAS [137-32-6]) were added and di-iso-propyl azodicarboxylate (0.674 ml, 3.44 mmol) was added dropwise while stirring at such a rate so as to maintain reaction mixture just below its boiling point. Reaction mixture was heated at 50° C. for further 30 minutes after completion of addition and then quenched with 30 ml of water. Product was extracted with diethyl ether/ethyl acetate 1:1 mixture (50 ml). Organic phase was washed with water and brine, dried and concentrated. Product was purified by chromatography (silica gel, 230-400 mesh, eluent: gradient heptane-ethyl acetate from 100:1 to 20:1). The title product was obtained as a pale yellow syrup (312 mg, 79% yield).

MS (ESI+): m/z=311.1 [M+Na]$^+$.

Example E14: (3S)-3-{4-[(2S)-2-methylbutoxy]phenyl}hex-4-ynoic acid methyl ester

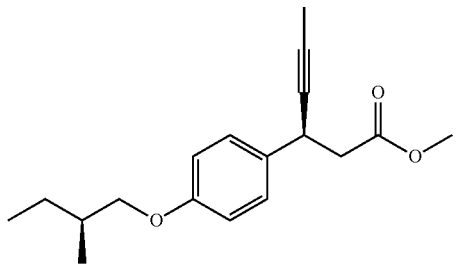

$C_{18}H_{24}O_3 = 288.38$

The title product was obtained as an oil (150 mg, 29% yield) under conditions as described in Example E13 starting from (3S)-3-(4-hydroxyphenyl)hex-4-ynoic acid methyl ester (400 mg, 1.83 mmol, Example I15), commercially available (S)-2-methyl-1-butanol (1.0 ml, 9.12 mmol, CAS [1565-80-6]) and other reagents and solvents in suitable proportions.

MS (ESI+): m/z=311.1 [M+Na]$^+$.

Example E15: (3S)-3-(4-{[(2E)-3,7-dimethylocta-2,6-dien-1-yl]oxy}phenyl)hex-4-ynoic acid methyl ester

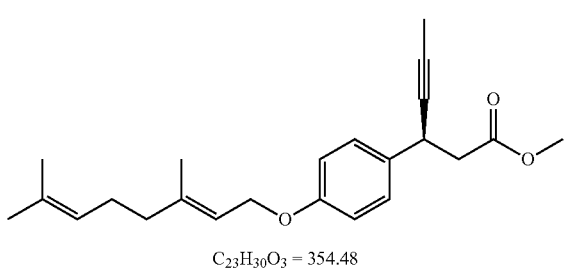 [SMILES: CC#C[C@@H](CC(=O)OC)c1ccc(OC/C=C(\C)CCC=C(C)C)cc1]

$C_{23}H_{30}O_3 = 354.48$

The title product was obtained as an oil (364 mg, 56% yield) under conditions as described in Example E13 starting from (3S)-3-(4-hydroxyphenyl)hex-4-ynoic acid methyl ester (400 mg, 1.83 mmol, Example I15), commercially available trans-3,7-dimethyl-2,6-octadien-1-ol (geraniol, 0.566 g, 3.67 mmol, CAS [1565-80-6]) and other reagents and solvents in suitable proportions.

MS (ESI+): m/z=377.2 [M+Na]$^+$.

Example E16: (3R)-3-(4-{[(2E)-3,7-dimethylocta-2,6-dien-1-yl]oxy}phenyl)hex-4-ynoic acid methyl ester

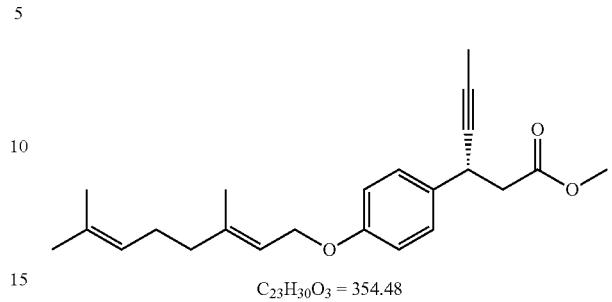

$C_{23}H_{30}O_3 = 354.48$

The title product was obtained as an oil (292 mg, 45% yield) under conditions as described in Example E13 starting from (3R)-3-(4-hydroxyphenyl)hex-4-ynoic acid methyl ester (400 mg, 1.83 mmol, Example I16), commercially available trans-3,7-dimethyl-2,6-octadien-1-ol (geraniol, 0.566 g, 3.67 mmol, CAS [1565-80-6]) and other reagents and solvents in suitable proportions.

MS (ESI+): m/z=377.2 [M+Na]$^+$.

Example E17: (3S)-3-(4-{[(2Z)-3,7-dimethylocta-2,6-dien-1-yl]oxy}phenyl)hex-4-ynoic acid methyl ester

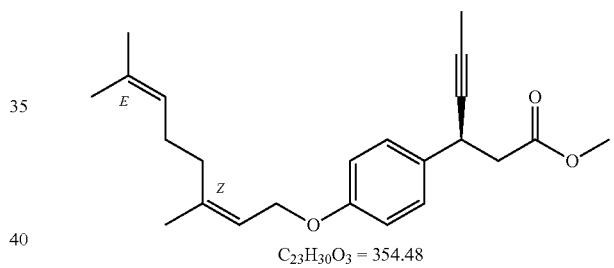

$C_{23}H_{30}O_3 = 354.48$

The title product was obtained as an oil (368 mg, 57% yield) under conditions as described in Example E13 starting from (3S)-3-(4-hydroxyphenyl)hex-4-ynoic acid methyl ester (400 mg, 1.83 mmol, Example I15), commercially available (Z)-3,7-dimethyl-2,6-octadien-1-ol (nerol, 0.874 g, 5.5 mmol, CAS [106-25-2]) and other reagents and solvents in suitable proportions.

MS (ESI+): m/z=377.2 [M+Na]$^+$.

Example E18: (3S)-3-(4-{[(3R)-3,7-dimethylocta-6-en-1-yl]oxy}phenyl)hex-4-ynoic acid methyl ester

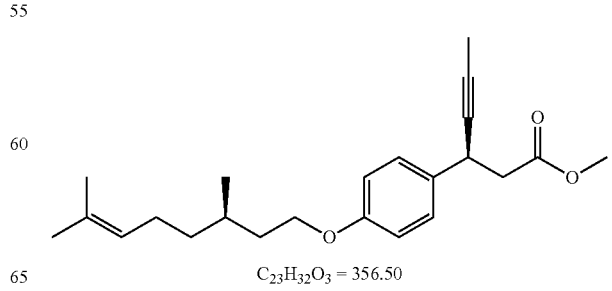

$C_{23}H_{32}O_3 = 356.50$

The title product was obtained as an oil (330 mg, 51% yield) under conditions as described in Example E13 starting from (3S)-3-(4-hydroxyphenyl)hex-4-ynoic acid methyl ester (400 mg, 1.83 mmol, Example I15), commercially available (R)-(+)-citronellol (0.584 g, 3.67 mmol, CAS [1117-61-9]) and other reagents and solvents in suitable proportions.

MS (ESI+): m/z=379.2 [M+Na]$^+$.

Example E19: (3S)-3-(4-{[(3S)-3,7-dimethylocta-6-en-1-yl]oxy}phenyl)hex-4-ynoic acid methyl ester

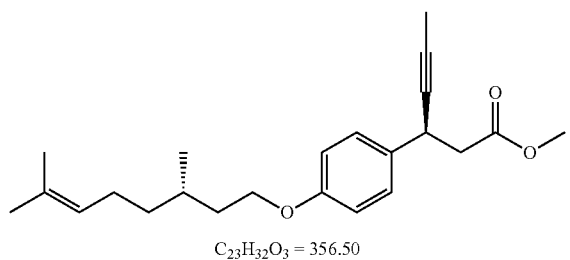 [SMILES: CC#C[C@@H](CC(=O)OC)c1ccc(OCC[C@@H](C)CCC=C(C)C)cc1]

$C_{23}H_{32}O_3 = 356.50$

The title product was obtained as an oil (395 mg, 61% yield) under conditions as described in Example E13 starting from (3S)-3-(4-hydroxyphenyl)hex-4-ynoic acid methyl ester (400 mg, 1.83 mmol, Example I15), commercially available (S)-(−)-citronellol (0.877 g, 5.5 mmol, CAS [1117-61-9]) and other reagents and solvents in suitable proportions.

MS (ESI+): m/z=379.2 [M+Na]$^+$.

Example E20: (3R/S)-3-(4-{[(2E,6E)-3,7,11-trimethyldodeca-2,6,10-trien-1-yl]oxy}-phenyl)hex-4-ynoic acid methyl ester

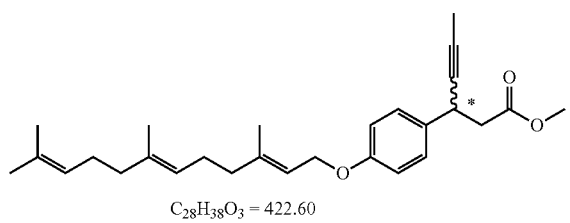

$C_{28}H_{38}O_3 = 422.60$ (* racemate)

The title product was obtained as an oil (204 mg, racemate, 70% yield) under conditions as described in Example E13 starting from (3R/S)-3-(4-hydroxyphenyl)-hex-4-ynoic acid (150 mg, 0.67 mmol, Example I7, esterified under conditions of Example I15), commercially available trans, trans-farnesol (0.271 g, 1.17 mmol, CAS 106-28-5]) and other reagents and solvents in suitable proportions.

MS (ESI+): m/z=445.3 [M+Na]$^+$.

Example E21: (3S)-3-{4-[(2,3-dimethylbut-2-en-1-yl)oxy]phenyl}hex-4-ynoic acid methyl ester

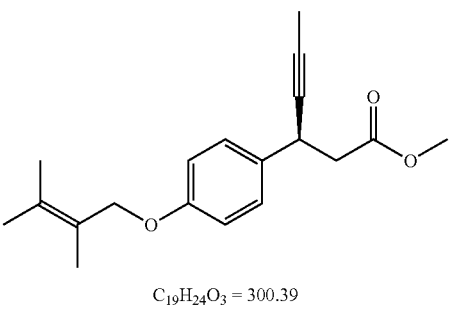 [SMILES: CC#C[C@@H](CC(=O)OC)c1ccc(OCC(C)=C(C)C)cc1]

$C_{19}H_{24}O_3 = 300.39$

The title product was obtained as an oil (850 mg, 39% yield) under conditions as described in Example E13 starting from (3S)-3-(4-hydroxyphenyl)hex-4-ynoic acid methyl ester (1.6 mg, 7.33 mmol, Example I15), 2,3-dimethylbut-2-en-1-ol (1.47 g, 14.7 mmol, obtained in Example I20) and other reagents and solvents in suitable proportions.

MS (ESI+): m/z=323.2 [M+Na]$^+$, 623.3 [2M+Na]$^+$.

Example E22: (3S)-3-[4-(pent-3-yn-1-yloxy)phenyl]hex-4-ynoic acid methyl ester

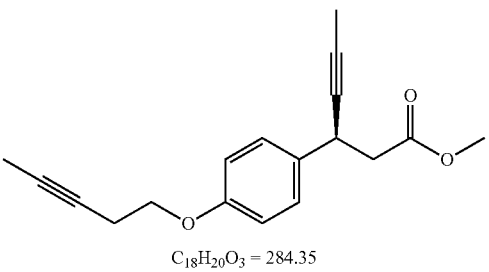 [SMILES: CC#CCCOc1ccc([C@@H](C#CC)CC(=O)OC)cc1]

$C_{18}H_{20}O_3 = 284.35$

The title product was obtained as an oil (109 mg, 60% yield) under conditions as described in Example E13 starting from (3S)-3-(4-hydroxyphenyl)hex-4-ynoic acid methyl ester (140 mg, 0.641 mmol, Example I15), commercially available 3-pentyn-1-ol (0.540 g, 6.41 mmol, CAS [10229-10-4]) and other reagents and solvents in suitable proportions.

MS (ESI+): m/z=307.1 [M+Na]$^+$.

Example E23: (3S)-3-[4-(pent-2-yn-1-yloxy)phenyl]hex-4-ynoic acid methyl ester

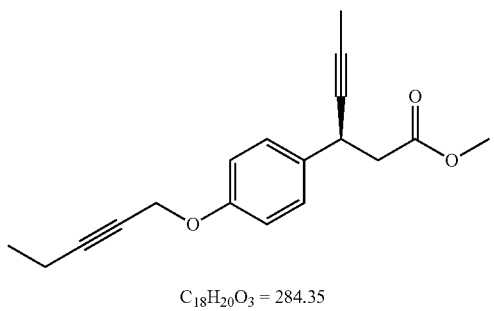 [SMILES: CC#C[C@@H](CC(=O)OC)c1ccc(OCC#CCC)cc1]

$C_{18}H_{20}O_3 = 284.35$

The title product was obtained as an oil (139 mg, 36% yield) under conditions as described in Example E13 starting from (3S)-3-(4-hydroxyphenyl)hex-4-ynoic acid methyl ester (300 mg, 1.37 mmol, Example I15), commercially available 2-pentyn-1-ol (0.590 g, 6.87 mmol, CAS [6261-22-9]) and other reagents and solvents in suitable proportions.

MS (ESI+): m/z=307.1 [M+Na]$^+$.

Example E24: (3S)-3-{4-[(2E)-hex-2-en-1-yloxy]phenyl}hex-4-ynoic acid methyl ester

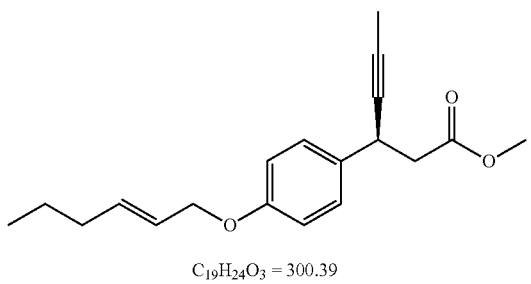

$C_{19}H_{24}O_3 = 300.39$

The title product was obtained as an oil (256 mg, 62% yield) under conditions as described in Example E13 starting from (3S)-3-(4-hydroxyphenyl)hex-4-ynoic acid methyl ester (300 mg, 1.37 mmol, Example I15), commercially available trans-2-hexen-1-ol (0.725 g, 6.87 mmol, CAS [928-95-0]) and other reagents and solvents in suitable proportions.

MS (ESI+): m/z=323.2 [M+Na]$^+$.

Example E25: (3S)-3-[4-(pent-4-en-1-yloxy)phenyl]hex-4-ynoic acid methyl ester

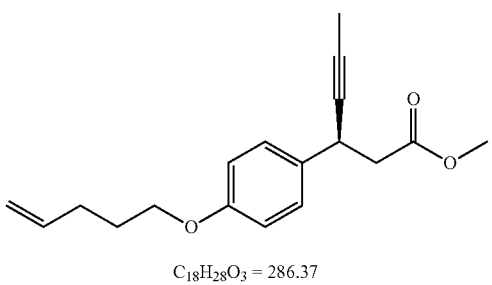 [SMILES: C=CCCCOc1ccc([C@@H](C#CC)CC(=O)OC)cc1]

$C_{18}H_{28}O_3 = 286.37$

The title product was obtained as an oil (291 mg, 74% yield) under conditions as described in Example E13 starting from (3S)-3-(4-hydroxyphenyl)hex-4-ynoic acid methyl ester (300 mg, 1.37 mmol, Example I15), commercially available 4-penten-1-ol (0.237 g, 2.75 mmol, CAS [821-09-0]) and other reagents and solvents in suitable proportions.

MS (ESI+): m/z=309.1 [M+Na]$^+$.

Example E26: (3S)-3-{4-[(2E,4E)-hexa-2,4-dien-1-yloxy]phenyl}hex-4-ynoic acid methyl ester

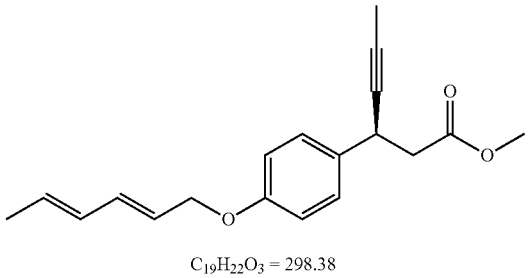 [SMILES: CC#C[C@@H](CC(=O)OC)c1ccc(OC/C=C/C=C/C)cc1]

$C_{19}H_{22}O_3 = 298.38$

The title product was obtained as a syrup (342 mg, 83% yield) under conditions as described in Example E13 starting from (3S)-3-(4-hydroxyphenyl)hex-4-ynoic acid methyl ester (300 mg, 1.37 mmol, Example I15), commercially available trans,trans-2,4-hexadien-1-ol (0.167 g, 1.65 mmol, CAS [17102-64-6]) and other reagents and solvents in suitable proportions.

MS (ESI+): m/z=321.1 [M+Na]$^+$.

Example E27: (3S)-3-{4-[(2R/S)-pentan-2-yloxy]phenyl}hex-4-ynoic acid methyl ester

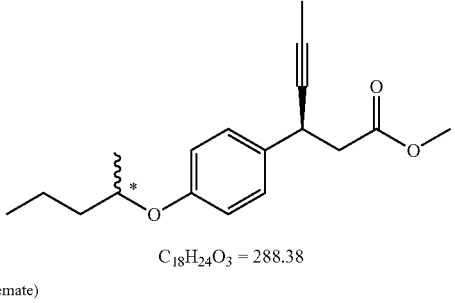

$C_{18}H_{24}O_3 = 288.38$ (* racemate)

The title product was obtained as a syrup (312 mg, 79% yield) under conditions as described in Example E13 starting from (3S)-3-(4-hydroxyphenyl)hex-4-ynoic acid methyl ester (300 mg, 1.37 mmol, Example I15), commercially available 2-pentanol (0.148 g, 1.65 mmol, CAS [6032-29-7]) and other reagents and solvents in suitable proportions.

MS (ESI+): m/z=311.1 [M+Na]$^+$.

Example E28: (3S)-3-(4-{[(3R/S)-3-methylpentyl]oxy}phenyl)hex-4-ynoic acid methyl ester

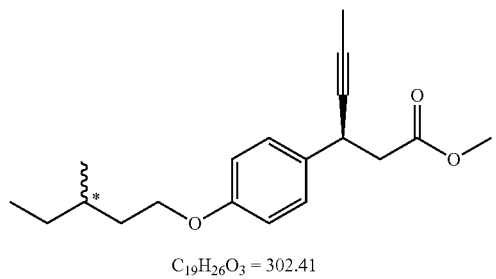

$C_{19}H_{26}O_3$ = 302.41

(* racemate)

The title product was obtained as a syrup (332 mg, 80% yield) under conditions as described in Example E13 starting from (3S)-3-(4-hydroxyphenyl)hex-4-ynoic acid methyl ester (300 mg, 1.37 mmol, Example I15), commercially available 3-methyl-1-pentanol (0.248 g, 2.75 mmol, CAS [589-35-5]) and other reagents and solvents in suitable proportions.

MS (ESI+): m/z=325.2 [M+Na]$^+$.

Example E29: (3S)-3-[4-(pentan-3-yloxy)phenyl]hex-4-ynoic acid methyl ester

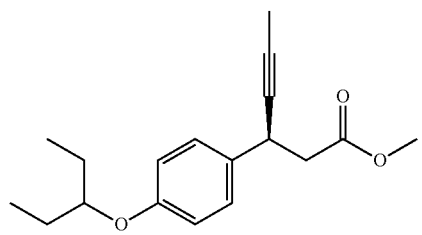

$C_{18}H_{24}O_3$ = 288.38

The title product was obtained as a syrup (100 mg, 54% yield) under conditions as described in Example E13 starting from (3S)-3-(4-hydroxyphenyl)hex-4-ynoic acid methyl ester (140 mg, 0.641 mmol, Example I15), commercially available 3-pentanol (0.577 g, 6.41 mmol, CAS [584-02-1]) and other reagents and solvents in suitable proportions.

MS (ESI+): m/z=311.1 [M+Na]$^+$.

Example E30: (3S)-3-[4-(3,3-dimethylbutoxy)phenyl]hex-4-ynoic acid methyl ester

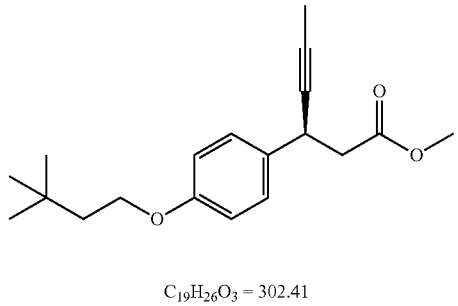 [SMILES: CC#C[C@@H](CC(=O)OC)c1ccc(OCCC(C)(C)C)cc1]

$C_{19}H_{26}O_3$ = 302.41

The title product was obtained as a syrup (120 mg, 49% yield) under conditions as described in Example E13 starting from (3S)-3-(4-hydroxyphenyl)hex-4-ynoic acid methyl ester (178 mg, 0.816 mmol, Example I15), commercially available 3,3-dimethyl-1-butanol (0.344 g, 3.26 mmol, CAS [624-95-3]) and other reagents and solvents in suitable proportions.

MS (ESI+): m/z=325.2 [M+Na]$^+$.

Example E31: (3S)-3-{4-[(2R/S)-2,3-dimethylbutoxy]phenyl}hex-4-ynoic acid methyl ester

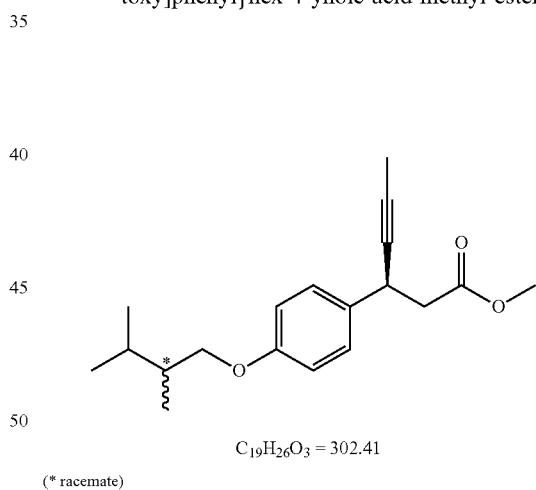

$C_{19}H_{26}O_3$ = 302.41

(* racemate)

The title product was obtained as an oil (1200 mg, 62% yield) under conditions as described in Example E13 starting from (3S)-3-(4-hydroxyphenyl)hex-4-ynoic acid methyl ester (1.4 g, 6.41 mmol, Example I15), (2R/S)-2,3-dimethylbutan-1-ol (1.30 g, 12.7 mmol, obtained in Example I21) and other reagents and solvents in suitable proportions.

MS (ESI+): m/z=325.2 [M+Na]$^+$.

Example E32: (3S)-3-{4-[(3-methylbut-3-en-1-yl)oxy]phenyl}hex-4-ynoic acid methyl ester

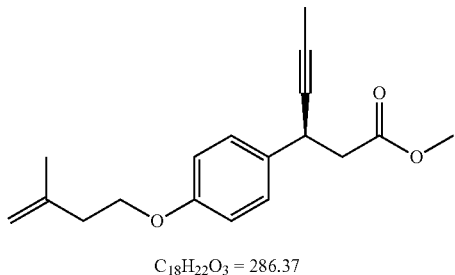 [SMILES: C=C(C)CCOc1ccc([C@@H](C#CC)CC(=O)OC)cc1]

$C_{18}H_{22}O_3 = 286.37$

The title product was obtained as a syrup (370 mg, 63% yield) under conditions as described in Example E13 starting from (3S)-3-(4-hydroxyphenyl)hex-4-ynoic acid methyl ester (450 mg, 2.06 mmol, Example I15), commercially available 3-methyl-3-buten-1-ol (0.512 g, 5.94 mmol, CAS [763-32-6]) and other reagents and solvents in suitable proportions.

MS (ESI+): m/z=309.1 [M+Na]+.

Example E33: (3S)-3-(4-{[(2R/S)-3-methylbutan-2-yl]oxy}phenyl)hex-4-ynoic acid methyl ester

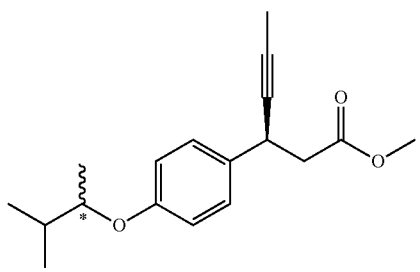

$C_{18}H_{24}O_3 = 288.38$ (* racemate)

The title product was obtained as a syrup (407 mg, 62% yield under conditions as described in Example E13 starting from (3S)-3-(4-hydroxyphenyl)hex-4-ynoic acid methyl ester (500 mg, 2.29 mmol, Example I15), commercially available 3-methyl-2-butanol (0.453 g, 5.04 mmol, CAS [598-75-4]) and other reagents and solvents in suitable proportions.

MS (ESI+): m/z=311.2 [M+Na]+.

Example E34: (3S)-3-{4-[(2R)-butan-2-yloxy]phenyl}hex-4-ynoic acid methyl ester

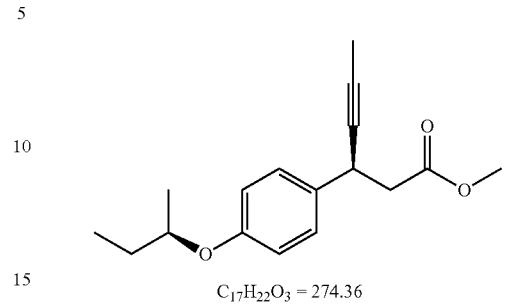

$C_{17}H_{22}O_3 = 274.36$

The title product was obtained as a syrup (415 mg, 66% yield) under conditions as described in Example E13 starting from (3S)-3-(4-hydroxyphenyl)hex-4-ynoic acid methyl ester (500 mg, 2.29 mmol, Example I15), commercially available (S)-(+)-2-butanol (0.401 g, 5.36 mmol, CAS [4221-99-2]) and other reagents and solvents in suitable proportions.

MS (ESI+): m/z=297.1 [M+Na]+.

Example E35: (3S)-3-{4-[(2S)-butan-2-yloxy]phenyl}hex-4-ynoic acid methyl ester

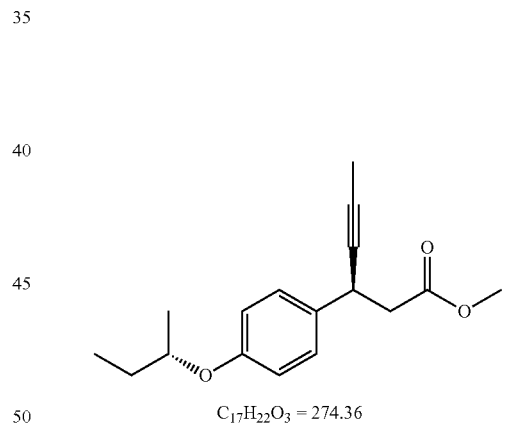

$C_{17}H_{22}O_3 = 274.36$

The title product was obtained as a syrup (369 mg, 59% yield) under conditions as described in Example E13 starting from (3S)-3-(4-hydroxyphenyl)hex-4-ynoic acid methyl ester (500 mg, 2.29 mmol, Example I15), commercially available (R)-(−)-2-butanol (0.401 g, 5.36 mmol, [14898-79-4]) and other reagents and solvents in suitable proportions.

MS (ESI+): m/z=297.1 [M+Na]+.

Example E36: (3S)-3-(4-{[(2E)-4-methylpenta-2,4-dien-1-yl]oxy}phenyl)hex-4-ynoic acid methyl ester

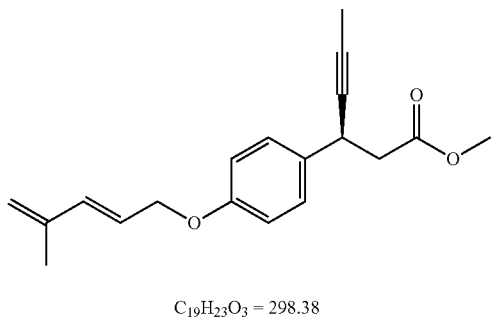 [SMILES: C=C(C)/C=C/COc1ccc([C@@H](C#CC)CC(=O)OC)cc1]

C₁₉H₂₃O₃ = 298.38

The title product was obtained as an oil (2.11 g, 52% yield) under conditions as described in Example E13 starting from (3S)-3-(4-hydroxyphenyl)hex-4-ynoic acid methyl ester (2.97 g, 13.6 mmol, Example I15), 2(E)-4-methyl-penta-2,4-dien-1-ol (2.0 g, 20.4 mmol, obtained in Example I28) and other reagents and solvents in suitable proportions.

MS (ESI+): m/z=321.1 [M+Na]$^+$.

Example E37: (3S)-3-(4-butoxyphenyl)hex-4-ynoic acid butyl ester

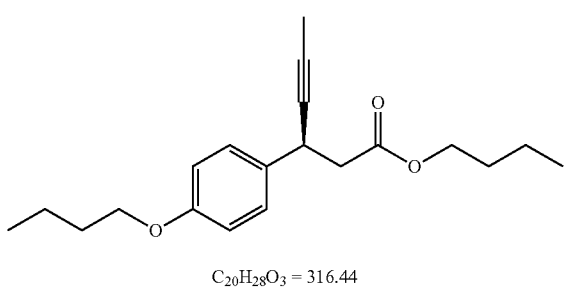 [SMILES: CC#C[C@@H](CC(=O)OCCCC)c1ccc(OCCCC)cc1]

C₂₀H₂₈O₃ = 316.44

(3S)-3-(4-Hydroxyphenyl)hex-4-ynoic acid obtained in Example I11 (244 mg, 1.19 mmol) and commercially available 1-bromobutane (0.9 ml, 8.36 mmol, CAS [109-65-9]) were dissolved in dry N,N'-dimethylformamide (10 ml), cesium carbonate (1.0 g, 3.04 mmol) was added and the whole was stirred at 50° C. for 18 hours. Reaction was quenched with water (50 ml). The product was extracted with diethyl ether/ethyl acetate 1:1 mixture (50 ml). Organic phase was washed with 3% aqueous sulfuric acid solution, water and brine, dried and concentrated. The product was purified by chromatography (silica gel 60, 230-400 mesh, eluent: heptane-ethyl acetate gradient from 100:1 to 20:1). The title product was obtained as a pale yellow syrup (275 mg, 73% yield).

$^1$H NMR (300 MHz, CDCl₃) δ: 7.31-7.22 (m, 2H), 6.87-6.79 (m, 2H), 4.18-3.99 (m, 1H), 4.07 (t, J=6.6 Hz, 2H), 3.94 (t, J=6.6 Hz, 2H), 2.69 (qd, J=15.0, 7.7 Hz, 2H), 1.82 (d, J=2.4 Hz, 3H), 1.81-1.69 (m, 2H), 1.62-1.42 (m, 4H), 1.41-1.23 (m, 2H), 0.96 (t, J=7.4 Hz, 3H), 0.91 (t, J=7.3 Hz, 3H).

$^{13}$C NMR (75 MHz, CDCl₃) δ: 171.42, 158.29, 133.13, 128.40, 114.64, 79.89, 78.76, 67.81, 64.53, 43.81, 33.69, 31.47, 30.78, 19.38, 19.19, 13.97, 13.82, 3.77.

MS (ESI+): m/z=339.1 [M+Na]$^+$, 355.2 [M+K]$^+$, 655.4 [2M+Na]$^+$.

Example E38: (3S)-3-[4-(Pentyloxy)phenyl]hex-4-ynoic acid pentyl ester

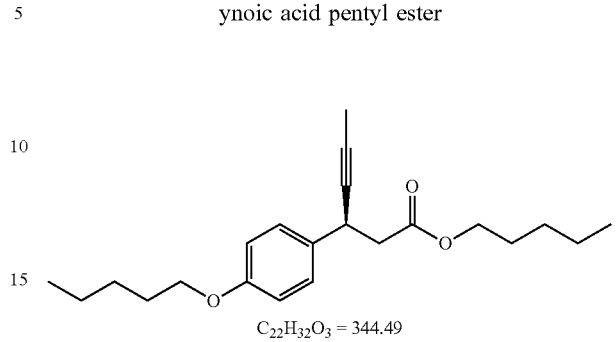

C₂₂H₃₂O₃ = 344.49

The title product was obtained as an oil (225 mg, 94% yield) under conditions as described in Example E37 starting from (3S)-3-(4-hydroxyphenyl)hex-4-ynoic acid (142 mg, 0.697 mmol, Example I11), commercially available 1-bromopentane (615 mg, 4.07 mmol, CAS [110-53-2]) and other reagents and solvents in suitable proportions.

$^1$H NMR (300 MHz, CDCl₃) δ: 7.31-7.22 (m, 2H), 6.87-6.79 (m, 2H), 4.06 (t, J=6.7 Hz, 2H), 4.10-3.99 (m, 1H), 3.92 (t, J=6.3 Hz, 2H), 2.69 (qd, J=15.0, 7.7 Hz, 2H), 1.82 (d, J=2.4 Hz, 3H), 1.80-1.71 (m, 2H), 1.66-1.52 (m, 2H), 1.51-1.21 (m, 8H), 0.98-0.82 (m, 6H).

$^{13}$C NMR (75 MHz, CDCl₃) δ: 171.42, 158.28, 133.13, 128.40, 114.63, 79.90, 78.75, 68.11, 64.84, 43.80, 33.68, 29.11, 28.44, 28.34, 28.13, 22.59, 22.44, 14.15, 14.08, 3.78.

MS (ESI+): m/z=367.2 [M+Na]$^+$.

Example E39: (3R/S)-3-[4-(3-methylbutoxy)phenyl]hex-4-ynoic acid 3-methylbutyl ester

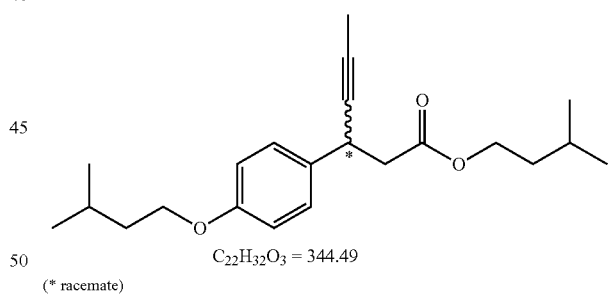

C₂₂H₃₂O₃ = 344.49

(* racemate)

The title product was obtained as an oil (327 mg, quantitative yield) under conditions as described in Example E37, starting from (3R/S)-3-(4-hydroxyphenyl)-hex-4-ynoic acid (200 mg, 0.979 mmol, Example I7), commercially available 1-bromo-3-methylbutane (0.3 ml, 2.45 mmol, CAS [107-82-4]) and other reagents and solvents in suitable proportions.

MS (ESI+): m/z=367.2 [M+Na]$^+$, 711.5 [2M+Na]$^+$.

Final Compounds of the Invention

Representative examples of the preparation of the compounds of the invention of formula (I) are presented below.

Examples of the compounds the number of which is preceded by letter F relate to the compounds of the invention in the form of free acids.

Examples of the compounds the number of which is preceded by letter S relate to the compounds of the invention in the form of salt.

Example F1: (3S)-3-(4-propoxyphenyl)hex-4-ynoic acid

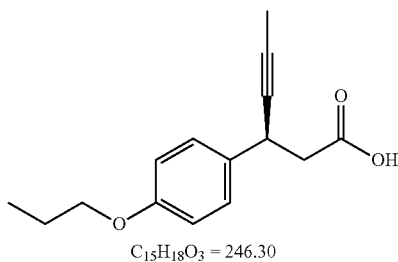 [SMILES: CC#C[C@@H](CC(=O)O)c1ccc(OCCC)cc1]

C$_{15}$H$_{18}$O$_3$ = 246.30

(3S)-3-(4-Propoxyphenyl)hex-4-ynoic acid methyl ester obtained in Example E1 (130 mg, 0.499 mmol) was dissolved in the mixture of tetrahydrofuran (20 ml) and methanol (10 ml), 120 mg (2.86 mmol) of lithium hydroxide monohydrate were added while stirring and the reaction mixture was heated at 40° C. with stirring for 18 hours. Reaction was quenched by addition of diethyl ether (20 ml) and acidification with 3% aqueous sulfuric acid solution (20 ml) and the product was extracted with ethyl acetate (2×20 ml). Organic phase was separated, washed with brine and dried. After evaporation the residue was purified by chromatography (silica gel, 230-400 mesh, eluent: heptane-ethyl acetate gradient from 5:1 to 1:1) to give 73 mg of the product (amorphous solid, 59% yield).

$^1$H NMR (300 MHz, CDCl$_3$) δ: 7.32-7.26 (m, 2H), 6.89-6.81 (m, 2H), 4.04 (ddq, J=8.8, 4.7, 2.2 Hz, 1H), 3.89 (t, J=6.6 Hz, 2H), 2.75 (qd, J=15.7, 7.6 Hz, 2H), 1.83 (d, J=2.4 Hz, 3H), 1.86-1.72 (m, 2H), 1.02 (t, J=7.4 Hz, 3H).

$^{13}$C NMR (75 MHz, CDCl$_3$) δ: 177.38, 158.36, 132.87, 128.41, 114.74, 79.61, 79.11, 69.67, 43.46, 33.26, 22.71, 10.65, 3.79.

MS (ESI+): m/z=269.1 [M+Na]$^+$, 285.1 [M+K]$^+$, 515.2 [2M+Na]$^+$. MS (ESI−): m/z=281.1 [M+Cl]$^−$, 491.2 [2M−H]$^−$.

Example F2: (3S)-3-(4-butoxyphenyl)hex-4-ynoic acid

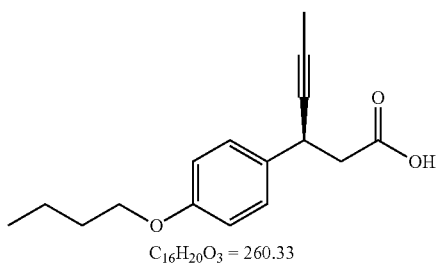 [SMILES: CC#C[C@@H](CC(=O)O)c1ccc(OCCCC)cc1]

C$_{16}$H$_{20}$O$_3$ = 260.33

The title product was obtained as an oil (178 mg, 88% yield) under conditions as described in Example F1, using (3S)-3-(4-butoxyphenyl)hex-4-ynoic acid butyl ester obtained in Example E37 (245 mg, 0.774 mmol) and other reagents and solvents in suitable proportions.

$^1$H NMR (300 MHz, CDCl$_3$) δ: δ 7.33-7.22 (m, 2H), 6.89-6.80 (m, 2H), 4.10-3.98 (m, 1H), 3.94 (t, J=6.5 Hz, 2H), 2.75 (qd, J=15.7, 7.6 Hz, 2H), 1.83 (d, J=2.4 Hz, 3H), 1.81-1.69 (m, 2H), 1.56-1.40 (m, 2H), 0.96 (t, J=7.4 Hz, 3H).

$^{13}$C NMR (75 MHz, CDCl$_3$) δ: 177.42, 158.36, 132.83, 128.40, 114.71, 79.60, 79.10, 67.83, 43.46, 33.25, 31.45, 19.38, 13.97, 3.78.

MS (ESI+): m/z=283.1 [M+Na]$^+$, 299.1 [M+K]$^+$, 543.3 [2M+Na]$^+$. MS (ESI−): m/z=259.1 [M−H]$^−$, 295.1 [M+Cl]$^−$, 519.3 [2M−H]$^−$.

Example F3: (3S)-3-[4-(pentyloxy)phenyl]hex-4-ynoic acid

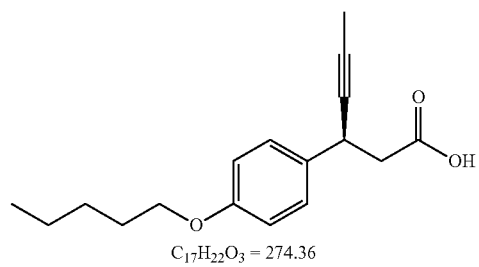 [SMILES: CC#C[C@@H](CC(=O)O)c1ccc(OCCCCC)cc1]

C$_{17}$H$_{22}$O$_3$ = 274.36

The title product was obtained as an oil (130 mg, 78% yield) under conditions as described in Example F1, using (3S)-3-(4-pentyloxyphenyl)hex-4-ynoic acid pentyl ester obtained in Example E38 (210 mg, 0.61 mmol) and other reagents and solvents in suitable proportions.

$^1$H NMR (300 MHz, CDCl$_3$) δ: 7.31-7.25 (m, 2H), 6.88-6.81 (m, 2H), 4.09-3.99 (m, 1H), 3.93 (t, J=6.0 Hz, 2H), 2.75 (qd, J=15.6, 7.6 Hz, 2H), 1.83 (d, J=2.4 Hz, 3H), 1.80-1.72 (m, 2H), 1.49-1.30 (m, 4H), 0.93 (t, J=7.1 Hz, 3H).

$^{13}$C NMR (75 MHz, CDCl$_3$) δ: 177.23, 158.36, 132.85, 128.41, 114.72, 79.62, 79.10, 68.15, 43.45, 33.27, 29.11, 28.34, 22.60, 14.16, 3.80.

MS (ESI+): m/z=297.1 [M+Na]$^+$, 313.1 [M+K]$^+$, 571.3 [2M+Na]$^+$. MS (ESI−): m/z=273.1 [M−H]$^−$, 309.1 [M+Cl]$^−$, 547.3 [2M−H]$^−$.

Example F4: (3S)-3-[4-(hexyloxy)phenyl]hex-4-ynoic acid

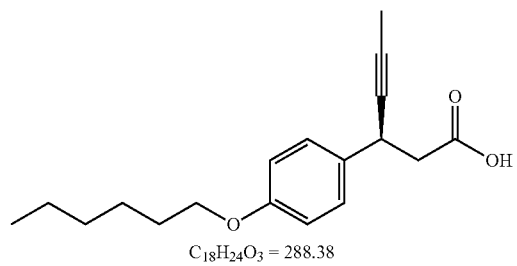 [SMILES: CC#C[C@@H](CC(=O)O)c1ccc(OCCCCCC)cc1]

C$_{18}$H$_{24}$O$_3$ = 288.38

The title product was obtained as an amorphous solid (75 mg, 56% yield) under conditions as described in Example F1, using (3S)-3-(4-hexyloxyphenyl)hex-4-ynoic acid methyl ester obtained in Example E2 (140 mg, 0.463 mmol) and other reagents and solvents in suitable proportions.

$^1$H NMR (300 MHz, CDCl$_3$) δ: 7.31-7.24 (m, 2H), 6.89-6.79 (m, 2H), 4.09-3.99 (m, 1H), 3.93 (t, J=6.6 Hz, 2H), 2.75 (qd, J=15.7, 7.6 Hz, 2H), 1.83 (d, J=2.4 Hz, 3H), 1.82-1.70 (m, 2H), 1.51-1.37 (m, 2H), 1.38-1.23 (m, 4H), 0.90 (t, J=7.0 Hz, 3H).

$^{13}$C NMR (75 MHz, CDCl$_3$) δ: 177.20, 158.39, 132.85, 128.41, 114.74, 79.62, 79.12, 68.18, 43.45, 33.28, 31.73, 29.39, 25.87, 22.75, 14.17, 3.80.

MS (ESI+): m/z=311.2 [M+Na]$^+$, 327.1 [M+K]$^+$, 599.3 [2M+Na]$^+$. MS (ESI−): m/z=287.2 [M−H]$^−$, 323.1 [M+Cl]$^−$, 575.3 [2M−H]$^−$.

Example F5: (3S)-3-[4-(heptyloxy)phenyl]hex-4-ynoic acid

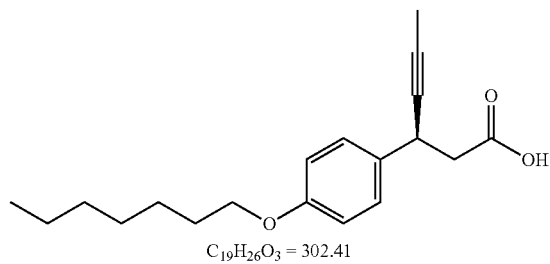 [SMILES: CC#C[C@@H](CC(=O)O)c1ccc(OCCCCCCC)cc1]

C$_{19}$H$_{26}$O$_3$ = 302.41

The title product was obtained as an amorphous solid (108 mg, 80% yield) under conditions as described in Example F1, using (3S)-3-(4-heptyloxyphenyl)hex-4-ynoic acid methyl ester obtained in Example E3 (140 mg, 0.463 mmol) and other reagents and solvents in suitable proportions.

$^1$H NMR (300 MHz, CDCl$_3$) δ: 7.32-7.24 (m, 2H), 6.89-6.80 (m, 2H), 4.04 (ddd, J=8.7, 5.6, 2.4 Hz, 1H), 3.93 (t, J=6.6 Hz, 2H), 2.75 (ddd, J=22.4, 15.7, 7.6 Hz, 2H), 1.83 (d, J=2.4 Hz, 3H), 1.87-1.69 (m, 2H), 1.50-1.22 (m, 8H), 0.89 (t, J=6.0 Hz, 3H).

$^{13}$C NMR (75 MHz, CDCl$_3$) δ: 177.22, 158.39, 132.85, 128.41, 114.74, 79.62, 79.12, 68.17, 43.45, 33.28, 31.93, 29.42, 29.20, 26.16, 22.75, 14.22, 3.80.

MS (ESI+): m/z=325.2 [M+Na]$^+$, 341.2 [M+K]$^+$, 627.4 [2M+Na]$^+$. MS (ESI−): m/z=337.2 [M+Cl]$^−$, 603.4 [2M−H]$^−$.

Example F6: (3S)-3-(4-{[(2E)-3,7-dimethylocta-2,6-dien-1-yl]oxy}phenyl)hex-4-ynoic acid

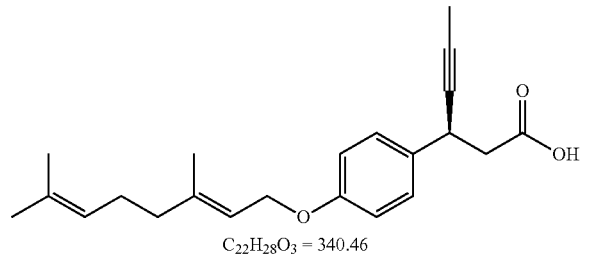 [SMILES: CC#C[C@@H](CC(=O)O)c1ccc(OC/C=C(\C)CCC=C(C)C)cc1]

C$_{22}$H$_{28}$O$_3$ = 340.46

The title product was obtained as an oil (246 mg, 73% yield) under conditions as described in Example F1, using (3S)-3-(4-{[(2E)-3,7-dimethylocta-2,6-dien-1-yl]oxy}phenyl)hex-4-ynoic acid methyl ester obtained in Example E15 (350 mg, 0.987 mmol) and other reagents and solvents in suitable proportions.

$^1$H NMR (300 MHz, CDCl$_3$) δ: 7.33-7.24 (m, 2H), 6.91-6.83 (m, 2H), 5.48 (td, J=6.5, 1.1 Hz, 1H), 5.14-5.04 (m, 1H), 4.51 (d, J=6.5 Hz, 2H), 4.05 (ddd, J=8.6, 6.6, 2.4 Hz, 1H), 2.75 (qd, J=15.7, 7.6 Hz, 2H), 2.20-2.02 (m, 4H), 1.83 (d, J=2.4 Hz, 3H), 1.73 (s, 3H), 1.68 (s, 3H), 1.61 (s, 3H).

$^{13}$C NMR (75 MHz, CDCl$_3$) δ: 176.96, 158.12, 141.31, 132.97, 131.94, 128.41, 123.95, 119.65, 114.92, 79.61, 79.13, 65.03, 43.41, 39.69, 33.28, 26.44, 25.82, 17.84, 16.78, 3.81.

MS (ESI+): m/z=363.2 [M+Na]$^+$. MS (ESI−): m/z=375.2 [M+Cl]$^−$.

Example F7: (3R)-3-(4-{[(2E)-3,7-dimethylocta-2,6-dien-1-yl]oxy}phenyl)hex-4-ynoic acid

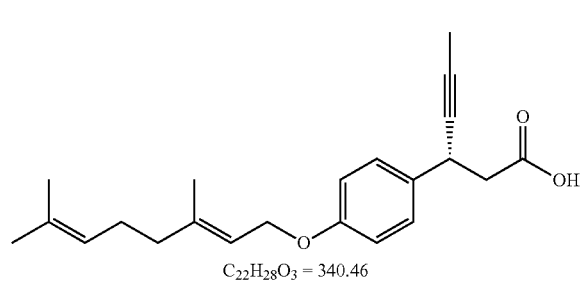 [SMILES: CC#C[C@H](CC(=O)O)c1ccc(OC/C=C(\C)CCC=C(C)C)cc1]

C$_{22}$H$_{28}$O$_3$ = 340.46

The title product was obtained as an oil (169 mg, 63% yield) under conditions as described in Example F1, using (3R)-3-(4-{[(2E)-3,7-dimethylocta-2,6-dien-1-yl]oxy}phenyl)hex-4-ynoic acid methyl ester obtained in Example E16 (280 mg, 0.790 mmol) and other reagents and solvents in suitable proportions. Spectral data identical with Example F6.

Example F8: (3S)-3-(4-{[(3R)-3,7-dimethylocta-6-en-1-yl]oxy}phenyl)hex-4-ynoic acid

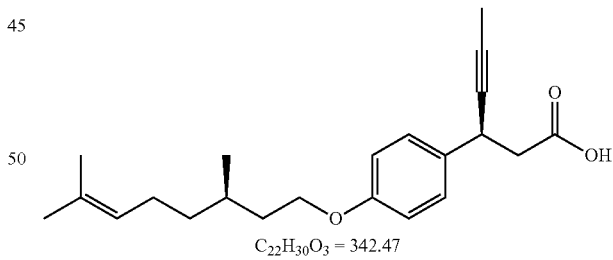

C$_{22}$H$_{30}$O$_3$ = 342.47

The title product was obtained as an oil (190 mg, 66% yield) under conditions as described in Example F1, using (3S)-3-(4-{[(3R)-3,7-dimethylocta-6-en-1-yl]oxy}-phenyl)hex-4-ynoic acid methyl ester obtained in Example E18 (300 mg, 0.842 mmol) and other reagents and solvents in suitable proportions.

$^1$H NMR (300 MHz, CDCl$_3$) δ: 7.32-7.23 (m, 2H), 6.88-6.80 (m, 2H), 5.15-5.06 (m, 1H), 4.10-3.92 (m, 3H), 2.75 (ddd, J=22.4, 15.7, 7.6 Hz, 2H), 2.10-1.91 (m, 2H), 1.83 (d, J=2.4 Hz, 3H), 1.88-1.75 (m, 1H), 1.68 (d, J=1.1 Hz, 3H), 1.60 (d, J=0.8 Hz, 3H), 1.74-1.50 (m, 2H), 1.46-1.32 (m, 1H), 1.28-1.14 (m, 1H), 0.94 (d, J=6.5 Hz, 3H).

$^{13}$C NMR (75 MHz, CDCl$_3$) δ: 177.23, 158.38, 132.89, 131.40, 128.41, 124.84, 114.77, 79.63, 79.12, 66.46, 43.46, 37.28, 36.30, 33.29, 29.69, 25.84, 25.60, 19.69, 17.80, 3.78.

MS (ESI+): m/z=365.2 [M+Na]$^+$. MS (ESI−): m/z=377.2 [M+Cl]$^-$.

Example F9: (3S)-3-(4-{[(3S)-3,7-dimethylocta-6-en-1-yl]oxy}phenyl)hex-4-ynoic acid

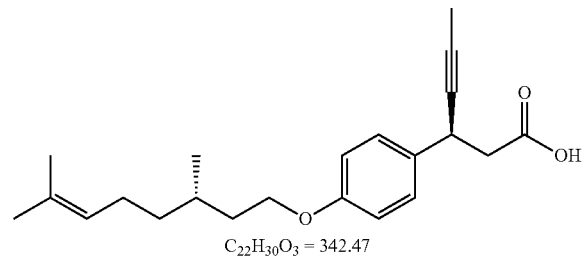 [SMILES: CC#C[C@@H](CC(=O)O)c1ccc(OCC[C@@H](C)CCC=C(C)C)cc1]

$C_{22}H_{30}O_3 = 342.47$

The title product was obtained as an oil (170 mg, 59% yield) under conditions as described in Example F1, using (3S)-3-(4-{[(3S)-3,7-dimethylocta-6-en-1-yl]oxy}-phenyl)hex-4-ynoic acid methyl ester obtained in Example E19 (300 mg, 0.842 mmol) and other reagents and solvents in suitable proportions. Spectral data identical with Example F8.

Example F10: (3S)-3-(4-{[(2Z)-3,7-dimethylocta-2,6-dien-1-yl]oxy}phenyl)hex-4-ynoic acid

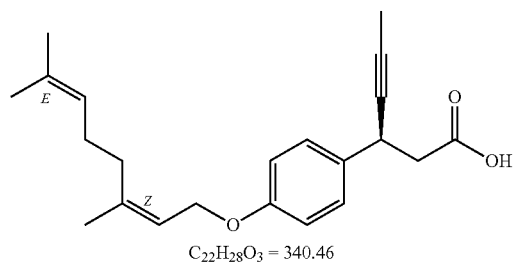 [SMILES: CC#C[C@@H](CC(=O)O)c1ccc(OC/C=C(/C)CCC=C(C)C)cc1]

$C_{22}H_{28}O_3 = 340.46$

The title product was obtained as an oil (231 mg, 69% yield) under conditions as described in Example F1, using (3S)-3-(4-{[(2Z)-3,7-dimethylocta-2,6-dien-1-yl]-oxy}phenyl)hex-4-ynoic acid methyl ester obtained in Example E17 (350 mg, 0.987 mmol) and other reagents and solvents in suitable proportions.

$^1$H NMR (300 MHz, CDCl$_3$) δ: 7.31-7.25 (m, 2H), 6.89-6.82 (m, 2H), 5.49 (td, J=6.7, 1.4 Hz, 1H), 5.16-5.05 (m, 1H), 4.48 (dd, J=6.7, 1.0 Hz, 2H), 4.05 (ddq, J=8.8, 4.7, 2.3 Hz, 1H), 2.75 (ddd, J=22.4, 15.7, 7.6 Hz, 2H), 2.17-2.07 (m, 4H), 1.83 (d, J=2.4 Hz, 3H), 1.79 (dd, J=2.3, 1.0 Hz, 3H), 1.68 (d, J=0.9 Hz, 3H), 1.60 (d, J=1.0 Hz, 3H).

$^{13}$C NMR (75 MHz, CDCl$_3$) δ: 177.08, 158.10, 141.71, 132.99, 132.29, 128.41, 123.80, 120.55, 114.91, 79.62, 79.13, 64.67, 43.43, 33.28, 32.56, 26.73, 25.83, 23.62, 17.80, 3.76.

MS (ESI+): m/z=363.2 [M+Na]$^+$. MS (ESI−): m/z=375.2 [M+Cl]$^-$.

Example F11: (3R/S)-3-(4-{[(2E,6E)-3,7,11-trimethyldodeca-2,6,10-trien-1-yl]oxy}-phenyl)hex-4-ynoic acid

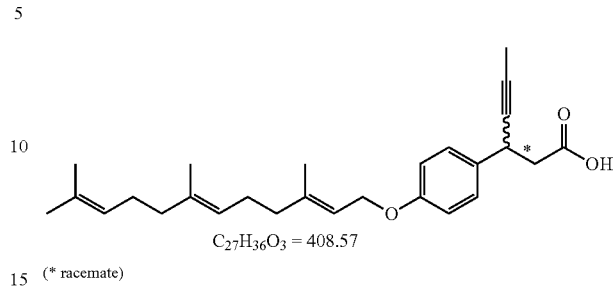

$C_{27}H_{36}O_3 = 408.57$ (* racemate)

The title product was obtained as an oil (42 mg, 33% yield) under conditions as described in Example F1, using (3R/S)-3-(4-{[(2E,6E)-3,7,11-trimethyldodeca-2,6,10-trien-1-yl]oxy}phenyl)hex-4-ynoic acid methyl ester obtained in Example E20 (198 mg, 0.469 mmol) and other reagents and solvents in suitable proportions.

$^1$H NMR (300 MHz, CDCl$_3$) δ: 7.34-7.23 (m, 2H), 6.93-6.81 (m, 2H), 5.48 (dt, J=6.5, 3.3 Hz, 1H), 5.17-5.04 (m, 2H), 4.51 (d, J=6.5 Hz, 2H), 4.10-4.00 (m, 1H), 2.75 (ddd, J=22.4, 15.7, 7.6 Hz, 2H), 2.20-1.93 (m, 8H), 1.83 (d, J=2.4 Hz, 3H), 1.73 (d, J=1.1 Hz, 3H), 1.68 (d, J=1.1 Hz, 3H), 1.60 (s, 6H).

$^{13}$C NMR (75 MHz, CDCl$_3$) δ: 176.85, 158.12, 141.34, 135.55, 132.98, 131.45, 128.40, 124.46, 123.83, 119.64, 114.91, 79.61, 79.12, 65.02, 43.40, 39.83, 39.69, 33.28, 26.85, 26.36, 25.83, 17.83, 16.80, 16.16, 3.80.

MS (ESI+): m/z=431.3 [M$^+$Na]$^+$. MS (ESI−): m/z=443.2 [M$^+$Cl]$^-$.

Example F12: (3S)-3-[4-(2-methylpropoxy)phenyl]hex-4-ynoic acid

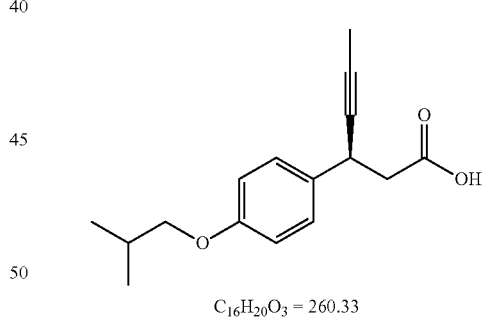

$C_{16}H_{20}O_3 = 260.33$

The title product was obtained as an amorphous solid (356 mg, 87% yield) under conditions as described in Example F1, using (3S)-3-[4-(2-methylpropoxy)phenyl]-hex-4-ynoic acid methyl ester obtained in Example I2 (430 mg, 1.57 mmol) and other reagents and solvents in suitable proportions.

$^1$H NMR (300 MHz, CDCl$_3$) δ: 7.31-7.25 (m, 2H), 6.88-6.80 (m, 2H), 4.04 (ddq, J=9.0, 7.0, 2.3 Hz, 1H), 3.69 (d, J=6.5 Hz, 2H), 2.75 (ddd, J=22.4, 15.7, 7.6 Hz, 2H), 2.07 (tq, J=13.3, 6.6 Hz, 1H), 1.82 (d, J=2.4 Hz, 3H), 1.01 (d, J=6.7 Hz, 6H).

$^{13}$C NMR (75 MHz, CDCl$_3$) δ: 177.30, 158.52, 132.86, 128.40, 114.79, 79.64, 79.10, 74.64, 43.45, 33.29, 28.40, 19.39, 3.78.

MS (ESI+): m/z=283.1 [M+Na]+. MS (ESI−): m/z=295.1 [M+Cl]−.

Example F13: (3S)-3-(4-{[(2R/S)-3-methylbutan-2-yl]oxy}phenyl)hex-4-ynoic acid

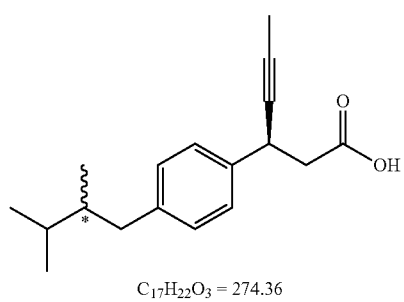

C17H22O3 = 274.36

(* racemate)

The title product was obtained as an amorphous solid (266 mg, 78% yield) under conditions as described in Example F1, using (3S)-3-(4-{[(2R/S)-3-methylbutan-2-yl]oxy}phenyl)hex-4-ynoic acid methyl ester obtained in Example 33 (360 mg, 1.248 mmol) and other reagents and solvents in suitable proportions.

$^1$H NMR (300 MHz, CDCl$_3$) δ: 7.31-7.22 (m, 2H), 6.87-6.79 (m, 2H), 4.12-4.07 (m, 1H), 4.10 (t, J=6.0, 1H), 2.75 (qd, J=15.7, 7.6 Hz, 2H), 1.91 (qd, J=12.5, 6.8 Hz, 1H), 1.83 (d, J=2.4 Hz, 3H), 1.21 (d, J=6.2 Hz, 3H), 0.96 (dd, J=8.7, 6.8 Hz, 6H).

$^{13}$C NMR (75 MHz, CDCl$_3$) δ: 177.18, 157.69, 132.78, 128.44, 116.17, 79.68, 79.08, 78.71, 43.48, 33.31, 33.14, 18.64, 17.89, 16.19, 3.77.

MS (ESI+): m/z=297.1 [M+Na]+. MS (ESI−): m/z=309.1 [M+Cl]−.

Example F14: (3S)-3-{4-[(2R)-butan-2-yloxy]phenyl}hex-4-ynoic acid

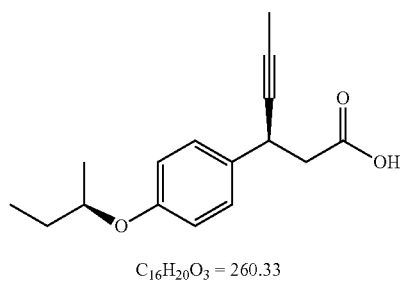 [SMILES: CC#C[C@@H](CC(=O)O)c1ccc(O[C@H](C)CC)cc1]

C16H20O3 = 260.33

The title product was obtained as an amorphous solid (345 mg, 91% yield) under conditions as described in Example F1, using (3S)-3-{4-[(2R)-butan-2-yloxy]phenyl}-hex-4-ynoic acid methyl ester obtained in Example 34 (400 mg, 1.458 mmol) and other reagents and solvents in suitable proportions.

$^1$H NMR (300 MHz, CDCl$_3$) δ: 7.30-7.22 (m, 2H), 6.87-6.79 (m, 2H), 4.26 (h, J=6.1 Hz, 1H), 4.04 (ddq, J=8.8, 4.7, 2.2 Hz, 1H), 2.75 (qd, J=15.6, 7.6 Hz, 2H), 1.83 (d, J=2.4 Hz, 3H), 1.81-1.52 (m, 2H), 1.27 (d, J=6.1 Hz, 3H), 0.96 (t, J=7.4 Hz, 3H).

$^{13}$C NMR (75 MHz, CDCl$_3$) δ: 177.13, 157.51, 132.87, 128.45, 116.16, 79.67, 79.09, 75.31, 43.47, 33.31, 29.35, 19.43, 9.91, 3.76.

MS (ESI+): m/z=283.1 [M+Na]+. MS (ESI−): m/z=395.1 [M+Cl]−.

Selected values of CD spectrum: −6.31479 m° (278.6 nm); −5.29875 m° (285 nm).

Example F15: (3S)-3-{4-[(2S)-butan-2-yloxy]phenyl}hex-4-ynoic acid

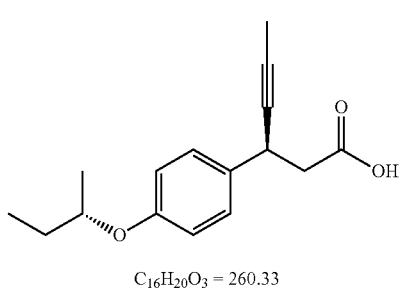 [SMILES: CC#C[C@@H](CC(=O)O)c1ccc(O[C@@H](C)CC)cc1]

C16H20O3 = 260.33

The title product was obtained as an oil (278 mg, 85% yield) under conditions as described in Example F1, using (3S)-3-{4-[(2S)-butan-2-yloxy]phenyl}hex-4-ynoic acid methyl ester obtained in Example 35 (345 mg, 1.262 mmol) and other reagents and solvents in suitable proportions. Spectral analysis data identical to those for Example F14.

Selected values of CD spectrum: +3.90002 m° (277.0 nm); +2.71404 m° (283.6 nm).

Example F16: (3S)-3-{4-[(2R/S)-pentan-2-yloxy]phenyl}hex-4-ynoic acid

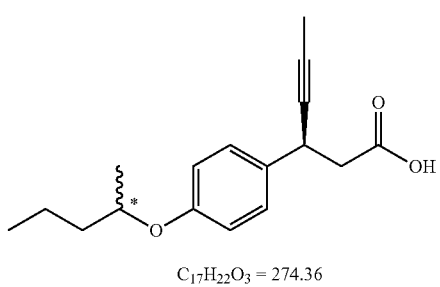

C17H22O3 = 274.36

(* racemate)

The title product was obtained as an oil (124 mg, 52% yield) under conditions as described in Example F1, using (3S)-3-{4-[(2R/S)-pentan-2-yloxy]phenyl}hex-4-ynoic acid methyl ester obtained in Example 27 (250 mg, 0.867 mmol) and other reagents and solvents in suitable proportions.

MS (ESI+): m/z=297.1 [M+Na]+. MS (ESI−): m/z=309.1 [M+Cl]−.

Example F17: (3S)-3-[4-(pentan-3-yloxy)phenyl]hex-4-ynoic acid

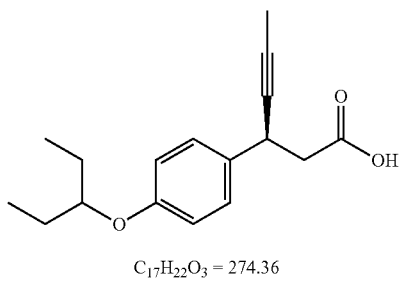 [SMILES: CC#C[C@@H](CC(=O)O)c1ccc(OC(CC)CC)cc1]

C₁₇H₂₂O₃ = 274.36

The title product was obtained as an oil (75 mg, 43% yield) under conditions as described in Example F1, using (3S)-3-[4-(pentan-3-yloxy)phenyl]hex-4-ynoic acid methyl ester obtained in Example 29 (185 mg, 0.641 mmol) and other reagents and solvents in suitable proportions.

$^1$H NMR (300 MHz, CDCl$_3$) δ: 7.31-7.23 (m, 2H), 6.88-6.80 (m, 2H), 4.12-3.99 (m, 2H), 2.75 (qd, J=15.7, 7.6 Hz, 2H), 1.83 (d, J=2.4 Hz, 3H), 1.72-1.60 (m, 4H), 0.94 (t, J=7.4 Hz, 6H).

$^{13}$C NMR (75 MHz, cdcl$_3$) δ 176.84, 157.98, 132.73, 128.44, 116.16, 80.40, 79.66, 79.10, 43.41, 33.28, 26.21, 9.75, 3.81.

MS (ESI+): m/z=397.1 [M+Na]$^+$. MS (ESI−): m/z=309.1 [M+Cl]$^−$.

Example F18: (3S)-3-{4-[(2E)-hex-2-en-1-yloxy]phenyl}hex-4-ynoic acid

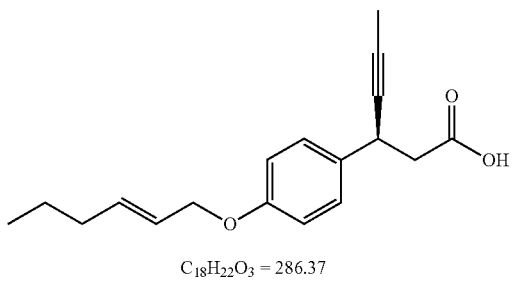 [SMILES: CC#C[C@@H](CC(=O)O)c1ccc(OC/C=C/CCC)cc1]

C₁₈H₂₂O₃ = 286.37

The title product was obtained as an amorphous solid (149 mg, 65% yield) under conditions as described in Example F1, using (3S)-3-{4-[(2E)-hex-2-en-1-yloxy]-phenyl}hex-4-ynoic acid methyl ester obtained in Example 24 (240 mg, 0.799 mmol) and other reagents and solvents in suitable proportions.

$^1$H NMR (300 MHz, CDCl$_3$) δ: 7.31-7.24 (m, 2H), 6.90-6.83 (m, 2H), 5.89-5.77 (m, 1H), 5.74-5.62 (m, 1H), 4.45 (dd, J=5.8, 1.0 Hz, 2H), 4.04 (ddd, J=8.7, 6.6, 2.4 Hz, 1H), 2.75 (qd, J=15.6, 7.6 Hz, 2H), 2.12-2.01 (m, 2H), 1.83 (d, J=2.4 Hz, 3H), 1.50-1.36 (m, 2H), 0.91 (t, J=7.4 Hz, 3H).

$^{13}$C NMR (75 MHz, CDCl$_3$) δ: 177.17, 157.98, 135.67, 133.06, 128.41, 125.03, 114.99, 79.57, 79.16, 69.03, 43.44, 34.54, 33.27, 22.27, 13.81, 3.80.

MS (ESI+): m/z=309.1 [M+Na]$^+$. MS (ESI−): m/z=321.1 [M+Cl]$^−$.

Example F19: (3S)-3-{4-[(2E,4E)-hexa-2,4-dien-1-yloxy]phenyl}hex-4-ynoic acid

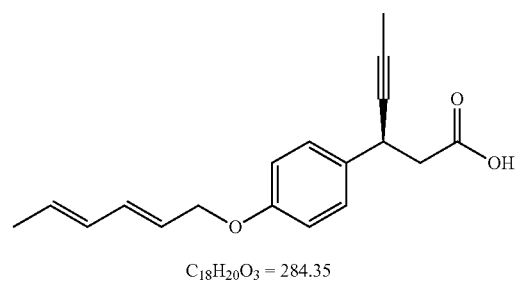 [SMILES: CC#C[C@@H](CC(=O)O)c1ccc(OC/C=C/C=C/C)cc1]

C₁₈H₂₀O₃ = 284.35

The title product was obtained as a solid (3.3 g, 54% yield) under conditions as described in Example F1, using (3S)-3-{4-[(2E,4E)-hexa-2,4-dien-1-yloxy]phenyl}-hex-4-ynoic acid methyl ester obtained in Example 26 (6.44 g, 21.6 mmol) and other reagents and solvents in suitable proportions.

H NMR (300 MHz, CDCl$_3$) δ: 7.35-7.21 (m, 2H), 6.94-6.78 (m, 2H), 6.31 (dd, J=15.2, 10.6 Hz, 1H), 6.08 (ddd, J=14.7, 10.5, 1.4 Hz, 1H), 5.86-5.65 (m, 2H), 4.52 (d, J=6.0 Hz, 2H), 4.10-3.97 (m, 1H), 2.75 (qd, J=15.7, 7.6 Hz, 2H), 1.83 (d, J=2.4 Hz, 3H), 1.77 (d, J=6.7 Hz, 3H).

$^{13}$C NMR (75 MHz, CDCl$_3$) δ: 176.87, 157.95, 133.93, 133.17, 130.87, 130.77, 128.45, 125.09, 115.03, 79.58, 79.19, 68.67, 43.40, 33.30, 18.24, 3.79.

MS (ESI+): m/z=307.1 [M+Na]$^+$. MS (ESI−): m/z=319.1 [M+Cl]$^−$.

Example F20: (3S)-3-[4-(pent-4-en-1-yloxy)phenyl]hex-4-ynoic acid

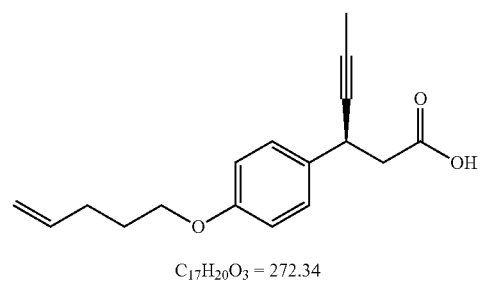 [SMILES: C=CCCCOc1ccc([C@@H](C#CC)CC(=O)O)cc1]

C₁₇H₂₀O₃ = 272.34

The title product was obtained as an amorphous solid (191 mg, 80% yield) under conditions as described in Example F1, using (3S)-3-[4-(pent-4-en-1-yloxy)phenyl]hex-4-ynoic acid methyl ester obtained in Example E25 (250 mg, 0.783 mmol) and other reagents and solvents in suitable proportions.

$^{13}$C NMR (75 MHz, CDCl$_3$) δ: 176.49, 158.26, 137.94, 133.01, 128.42, 115.30, 114.74, 79.65, 79.07, 67.32, 43.38, 33.28, 30.24, 28.56, 3.79.

MS (ESI+): m/z=295.1 [M+Na]$^+$. MS (ESI−): m/z=307.1 [M+Cl]$^−$.

Example F21: (3S)-3-[4-(pent-3-yn-1-yloxy)phenyl]hex-4-ynoic acid

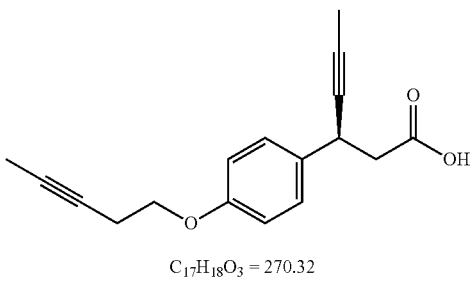 [SMILES: CC#CCCOc1ccc([C@@H](C#CC)CC(=O)O)cc1]

C₁₇H₁₈O₃ = 270.32

The title product was obtained as an amorphous solid (25 mg, 29% yield) under conditions as described in Example F1, using (3S)-3-[4-(pent-3-yn-1-yloxy)phenyl]-hex-4-ynoic acid methyl ester obtained in Example E22 (90 mg, 0.317 mmol) and other reagents and solvents in suitable proportions.

$^1$H NMR (300 MHz, CDCl$_3$) δ: 7.28 (d, J=8.7 Hz, 2H), 6.86 (d, J=8.7 Hz, 2H), 4.09-3.99 (m, 3H), 2.75 (qd, J=15.7, 7.6 Hz, 2H), 2.60 (td, J=7.2, 2.7 Hz, 2H), 1.83 (d, J=2.3 Hz, 3H), 1.79 (t, J=2.5 Hz, 3H).

$^{13}$C NMR (75 MHz, CDCl$_3$) δ: 176.64, 157.83, 133.41, 128.50, 114.95, 79.57, 79.21, 77.47, 75.18, 66.85, 43.34, 33.32, 19.95, 3.78, 3.64.

MS (ESI+): m/z=293.1 [M+Na]$^+$. MS (ESI−): m/z=305.1 [M+Cl]$^-$.

Example F22: (3S)-3-[4-(pent-2-yn-1-yloxy)phenyl]hex-4-ynoic acid

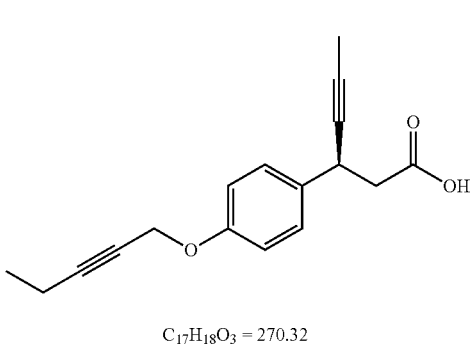 [SMILES: CC#C[C@@H](CC(=O)O)c1ccc(OCC#CCC)cc1]

C₁₇H₁₈O₃ = 270.32

The title product was obtained as a solid (70 mg, 60% yield) under conditions as described in Example F1, using (3S)-3-[4-(pent-2-yn-1-yloxy)phenyl]hex-4-ynoic acid methyl ester obtained in Example E23 (130 mg, 0.458 mmol) and other reagents and solvents in suitable proportions.

$^1$H NMR (300 MHz, CDCl$_3$) δ: 7.34-7.27 (m, 2H), 6.96-6.88 (m, 2H), 4.64 (t, J=2.1 Hz, 2H), 4.05 (ddd, J=8.6, 6.6, 2.4 Hz, 1H), 2.75 (qd, J=15.7, 7.6 Hz, 2H), 2.23 (qt, J=7.4, 2.1 Hz, 2H), 1.83 (d, J=2.4 Hz, 3H), 1.14 (t, J=7.5 Hz, 3H).

$^{13}$C NMR (75 MHz, CDCl$_3$) δ: 177.27, 157.12, 133.62, 128.41, 115.13, 89.66, 79.49, 79.23, 74.32, 56.68, 43.42, 33.26, 13.72, 12.63, 3.78.

MS (ESI+): m/z=293.1 [M+Na]$^+$. MS (ESI−): m/z=305.1 [M+Cl]$^-$.

Example F23: (3R/S)-3-[4-(3-methylbutoxy)phenyl]hex-4-ynoic acid

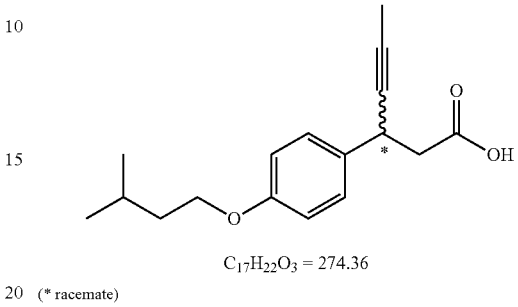

C₁₇H₂₂O₃ = 274.36

(* racemate)

The title product was obtained as a solid (210 mg, racemate, 81% yield) under conditions as described in Example F1, using (3R/S)-3-[4-(3-methylbutoxy)phenyl]-hex-4-ynoic acid 3-methylbutyl ester obtained in Example E39 (327 mg, 0.949 mmol) and other reagents and solvents in suitable proportions. Spectral analysis identical to that for Example F24.

Example F24: (3S)-3-[4-(3-methylbutoxy)phenyl]hex-4-ynoic acid

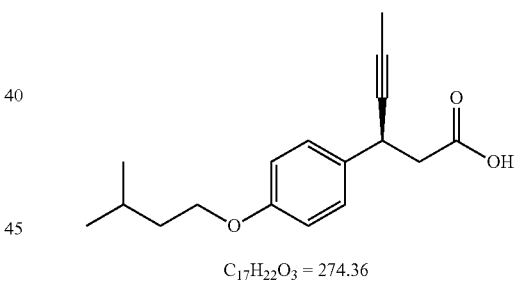

C₁₇H₂₂O₃ = 274.36

The title product was obtained as a crystalline solid (1.8 g, 77% yield) under conditions as described in Example F1, using (3S)-3-[4-(3-methylbutoxy)phenyl]hex-4-ynoic acid methyl ester obtained in Example E4 (2.47 g, 8.56 mmol) and other reagents and solvents in suitable proportions. Melting point: 26.4-27.1° C., after recrystallization from n-pentane.

$^1$H NMR (300 MHz, CDCl$_3$) δ: 7.27 (d, J=8.7 Hz, 2H), 6.84 (d, J=8.7 Hz, 2H), 4.13-4.00 (m, 1H), 3.96 (t, J=6.6 Hz, 2H), 2.75 (qd, J=15.7, 7.6 Hz, 2H), 1.83 (d, J=2.3 Hz, 3H), 1.97-1.74 (m, 1H), 1.66 (q, J=6.7 Hz, 2H), 0.95 (d, J=6.6 Hz, 6H).

$^{13}$C NMR (75 MHz, CDCl$_3$) δ: 177.44, 158.35, 132.84, 128.40, 114.72, 79.61, 79.11, 66.50, 43.47, 38.13, 33.25, 25.17, 22.71, 3.79.

MS (ESI+): m/z=297.1 [M+Na]$^+$, 571.3 [2M+Na]$^+$. MS (ESI−): m/z=309.1 [M+Cl]$^-$, 547.3 [2M−H]$^-$.

Example F25: (3S)-3-[4-(2-ethylbutoxy)phenyl]hex-4-ynoic acid

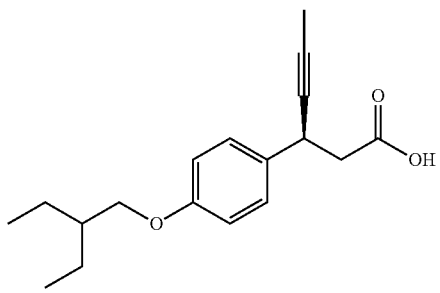

C₁₈H₂₄O₃ = 288.38

The title product was obtained as an oil (290 mg, 87% yield) under conditions as described in Example F1, using (3S)-3-[4-(2-ethylbutoxy)phenyl]hex-4-ynoic acid methyl ester obtained in Example E9 (350 mg, 1.15 mmol) and other reagents and solvents in suitable proportions.

$^1$H NMR (300 MHz, CDCl₃) δ: 7.32-7.23 (m, 2H), 6.89-6.81 (m, 2H), 4.09-3.99 (m, 1H), 3.82 (d, J=5.7 Hz, 2H), 2.75 (qd, J=15.7, 7.6 Hz, 2H), 1.83 (d, J=2.4 Hz, 3H), 1.71-1.58 (m, 1H), 1.55-1.36 (m, 4H), 0.92 (t, J=7.4 Hz, 6H).

$^{13}$C NMR (75 MHz, CDCl₃) δ: 176.92, 158.64, 132.77, 128.39, 114.75, 79.65, 79.10, 70.28, 43.40, 41.04, 33.29, 23.51, 11.27, 3.81.

MS (ESI+): m/z=311.2 [M+Na]⁺. MS (ESI−): m/z=323.1 [M+Cl]⁻.

Example F26: (3R/S)-3-[4-(2,2-dimethylpropoxy)phenyl]hex-4-ynoic acid

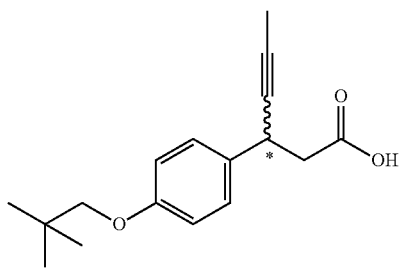

C₁₇H₂₂O₃ = 274.36

(* racemate)

2-[(1R/S)-1-[4-(2,2-Di methylpropoxy)phenyl]but-2-yn-1-yl]propanedioic acid obtained in Example I26 (730 mg, 2.29 mmol) was dissolved in 40 ml of toluene and heated at 100° C. while stirring for 18 hours. After evaporation, the residue was purified by chromatography (silica gel 60, 230-400 mesh, eluent: heptane-ethyl acetate gradient from 5:1 to 1:1) to obtain 195 mg of the product as a colorless wax (30% yield).

$^1$H NMR (300 MHz, CDCl₃) δ: 7.34-7.22 (m 2H), 6.90-6.80 (m, 2H), 4.10-3.98 (m, 1H), 3.56 (s, 2H), 2.75 (qd, J=15.7, 7.6 Hz, 2H), 1.83 (d, J=2.4 Hz, 3H), 1.02 (s, 9H).

$^{13}$C NMR (75 MHz, CDCl₃) δ: 177.30, 158.87, 132.76, 128.37, 114.75, 79.65, 79.08, 78.04, 43.43, 33.28, 32.01, 26.75, 3.80.

MS (ESI+): m/z=297.2 [M+Na]⁺, 571.3 [2M+Na]⁺. MS (ESI−): m/z=273.1 [M−H]⁻, 309.1 [M+Cl]⁻, 547.3 [2M−H]⁻.

Example F27: (3S)-3-[4-(3,3-dimethylbutoxy)phenyl]hex-4-ynoic acid

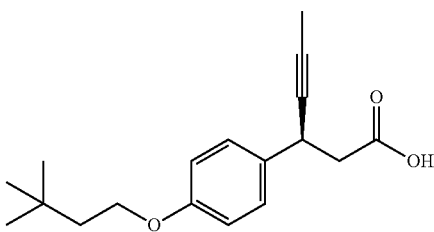

C₁₈H₂₄O₃ = 288.38

The title product was obtained as an oil (60 mg, 53% yield) under conditions as described in Example F1, using (3S)-3-[4-(3,3-dimethylbutoxy)phenyl]hex-4-ynoic acid methyl ester obtained in Example E30 (120 mg, 0.397 mmol) and other reagents and solvents in suitable proportions.

$^1$H NMR (300 MHz, CDCl₃) δ: 7.34-7.23 (m, 2H), 6.92-6.80 (m, 2H), 4.09-3.95 (m, 1H), 4.00 (t, J=9.0 Hz, 2H), 2.75 (qd, J=15.7, 7.6 Hz, 2H), 1.83 (d, J=2.4 Hz, 3H), 1.71 (t, J=7.3 Hz, 2H), 0.98 (s, 9H).

$^{13}$C NMR (75 MHz, CDCl₃) δ: 176.94, 158.31, 132.87, 128.43, 114.77, 79.64, 79.13, 65.51, 43.42, 42.55, 33.31, 29.94, 29.89, 3.79.

MS (ESI+): m/z=311.2 [M+Na]⁺. MS (ESI−): m/z=323.1 [M+Cl]⁻.

Example F28: (3S)-3-{4[(3-methylbut-2-en-1-yl)oxy]phenyl}hex-4-ynoic acid

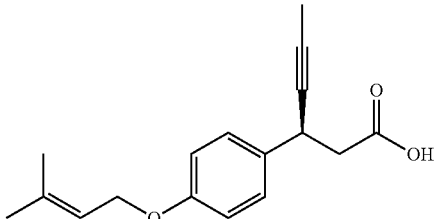

C₁₇H₂₀O₃ = 272.34

The title product was obtained as a crystalline solid (1.65 g, 44% yield) under conditions as described in Example F1, using (3S)-3-{4-[(3-methylbut-2-en-1-yl)-oxy]phenyl}hex-4-ynoic acid methyl ester obtained in Example E5 (3.93 g, 13.7 mmol) and other reagents and solvents in suitable proportions. Melting point: 52.1-53.1° C., after recrystallization from n-pentane.

$^1$H NMR (300 MHz, CDCl₃) δ: 7.33-7.26 (m, 2H), 6.90-6.82 (m, 2H), 5.55-5.42 (m, 1H), 4.49 (d, J=6.7 Hz,

2H), 4.10-3.98 (m, 1H), 2.75 (qd, J=15.7, 7.6 Hz, 2H), 1.83 (d, J=2.4 Hz, 3H), 1.79 (s, 3H), 1.73 (s, 3H).

$^{13}$C NMR (75 MHz, CDCl$_3$) δ: 176.49, 158.16, 138.19, 133.06, 128.43, 119.93, 114.96, 79.66, 79.14, 65.00, 43.37, 33.34, 25.93, 18.31, 3.77.

MS (ESI+): m/z=295.1 [M+Na]$^+$, 567.2 [2M+Na]$^+$. MS (ESI−): m/z=307.1 [M+Cl]$^−$.

Example F29: (3R)-3-{4-[(3-methylbut-2-en-1-yl)oxy]phenyl}hex-4-ynoic acid

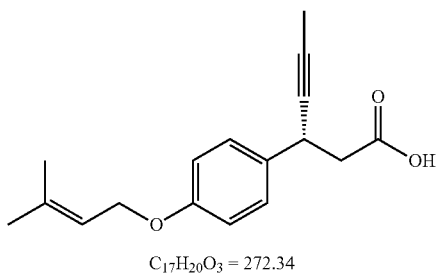 [SMILES: CC#C[C@H](CC(=O)O)c1ccc(OCC=C(C)C)cc1]

C$_{17}$H$_{20}$O$_3$ = 272.34

The title product was obtained as a solid (198 mg, 69% yield) under conditions as described in Example F1, using (3R)-3-{4-[(3-methylbut-2-en-1-yl)oxy]phenyl}hex-4-ynoic acid methyl ester obtained in Example E6 (300 mg, 1.05 mmol) and other reagents and solvents in suitable proportions. Spectral analysis identical to that for Example F28.

Example F30: (3S)-3-{4[(3-methylbut-3-en-1-yl)oxy]phenyl}hex-4-ynoic acid

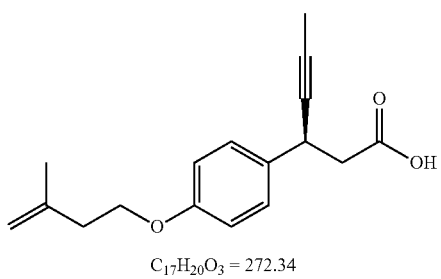 [SMILES: C=C(C)CCOc1ccc([C@@H](C#CC)CC(=O)O)cc1]

C$_{17}$H$_{20}$O$_3$ = 272.34

The title product was obtained as an oil (275 mg, 78% yield) under conditions as described in Example F1, using (3S)-3-{4-[(3-methylbut-3-en-1-yl)oxy]phenyl}hex-4-ynoic acid methyl ester obtained in Example E32 (370 mg, 1.29 mmol) and other reagents and solvents in suitable proportions.

$^1$H NMR (300 MHz, CDCl$_3$) δ: 7.32-7.25 (m, 2H), 6.89-6.81 (m, 2H), 4.86-4.75 (m, 2H), 4.06 (t, J=9.0 Hz, 2H), 4.10-4.00 (m, 1H), 2.75 (qd, J=15.7, 7.6 Hz, 2H), 2.48 (t, J=6.8 Hz, 2H), 1.83 (d, J=2.4 Hz, 3H), 1.81-1.78 (m, 3H).

$^{13}$C NMR (75 MHz, CDCl$_3$) δ: 177.18, 158.15, 142.33, 133.10, 128.44, 114.85, 112.10, 79.60, 79.15, 66.68, 43.44, 37.34, 33.29, 22.96, 3.79.

MS (ESI+): m/z=295.1 [M+Na]$^+$. MS (ESI−): m/z=307.1 [M+Cl]$^−$.

Example F31: (3R)-3-{2-fluoro-4-[(3-methylbut-2-en-1-yl)oxy]phenyl}hex-4-ynoic acid

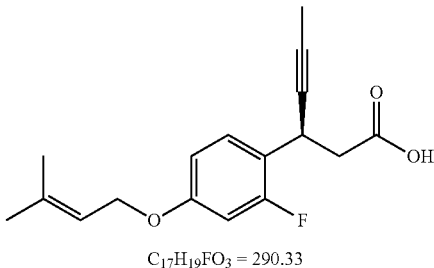 [SMILES: CC#C[C@@H](CC(=O)O)c1ccc(OCC=C(C)C)cc1F]

C$_{17}$H$_{19}$FO$_3$ = 290.33

The title product was obtained as an oil (25 mg, 80% yield) under conditions as described in Example F1, using (3R)-3-{2-fluoro-4-[(3-methylbut-2-en-1-yl)oxy]phenyl}hex-4-ynoic acid methyl ester obtained in Example E7 (32 mg, 0.105 mmol) and other reagents and solvents in suitable proportions.

$^1$H NMR (300 MHz, CDCl$_3$) δ: 7.41 (t, J=8.8 Hz, 1H), 6.69 (dd, J=8.6, 2.5 Hz, 1H), 6.60 (dd, J=12.2, 2.5 Hz, 1H), 5.52-5.41 (m, 1H), 4.47 (d, J=6.7 Hz, 2H), 4.31 (ddd, J=8.6, 6.2, 2.4 Hz, 1H), 2.84-2.68 (m, 2H), 1.84 (d, J=2.4 Hz, 3H), 1.80 (s, 3H), 1.74 (s, 3H).

$^{19}$F NMR (282 MHz, CDCl$_3$) δ: −121.21 (dd, J=12.2, 9.0 Hz).

$^{13}$C NMR (75 MHz, CDCl$_3$) δ: 176.98, 160.50 (d, J$_{C-F}$=244.5 Hz), 159.43 (d, J$_{C-F}$=10.9 Hz), 138.79, 129.72 (d, J$_{C-F}$=5.9 Hz), 119.45 (d, J$_{C-F}$=14.3 Hz), 119.31, 110.81 (d, J$_{C-F}$=2.8 Hz), 102.43 (d, J$_{C-F}$=25.1 Hz), 79.15, 78.33, 65.25, 41.62, 27.39, 27.37 (d, J$_{C-F}$=2.7 Hz), 18.33, 3.77.

MS (ESI+): m/z=313.1 [M+Na]$^+$. MS (ESI−): m/z=325.1 [M+Cl]$^−$.

Example F32: (3S)-3-{2-fluoro-4-[(3-methylbut-2-en-1-yl)oxy]phenyl}hex-4-ynoic acid

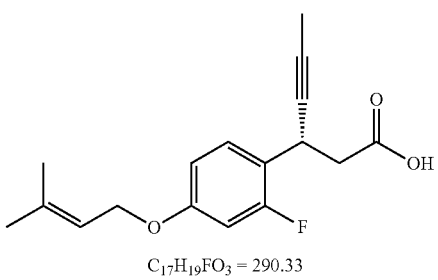

C$_{17}$H$_{19}$FO$_3$ = 290.33

The title product was obtained as an oil (32 mg, 78% yield) under conditions as described in Example F1, using (3S)-3-{2-fluoro-4-[(3-methylbut-2-en-1-yl)oxy]phenyl}hex-4-ynoic acid methyl ester obtained in Example E8 (44 mg, 0.145 mmol) and other reagents and solvents in suitable proportions. Spectral analysis identical to that for Example F31.

Example F33: (3S)-3-{4-[(2,3-dimethylbut-2-en-1-yl)oxy]phenyl}hex-4-ynoic acid

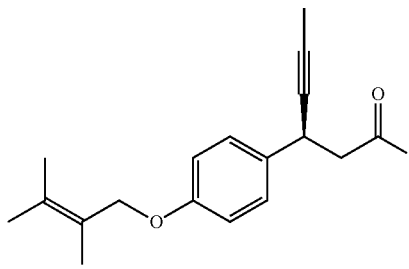

C₁₆H₂₂O₃ = 286.37

The title product was obtained as an oil (766 mg, 80% yield) under conditions as described in Example F1, using (3S)-3-{4-[(2,3-dimethylbut-2-en-1-yl)oxy]phenyl}-hex-4-ynoic acid methyl ester obtained in Example E21 (1.0 g, 3.33 mmol) and other reagents and solvents in suitable proportions.

$^1$H NMR (300 MHz, CDCl₃) δ: 7.36-7.22 (m, 2H), 6.91-6.80 (m, 2H), 4.47 (s, 2H), 4.14-3.94 (m, 1H), 2.75 (qd, J=15.6, 7.5 Hz, 2H), 1.82 (d, J=2.4 Hz, 3H), 1.77 (s, 6H), 1.74 (s, 3H).

$^3$C NMR (75 MHz, CDCl₃) δ: 176.28, 158.64, 133.07, 131.04, 128.41, 124.16, 115.07, 79.72, 79.14, 69.49, 43.35, 33.40, 21.09, 20.37, 16.79, 3.74.

MS (ESI+): m/z=309.1 [M+Na]⁺. MS (ESI−): m/z=321.1 [M+Cl]⁻.

Example F34: (3S)-3-(4-{[(2E)-4-methylpenta-2,4-dien-1-yl]oxy}phenyl)hex-4-ynoic acid

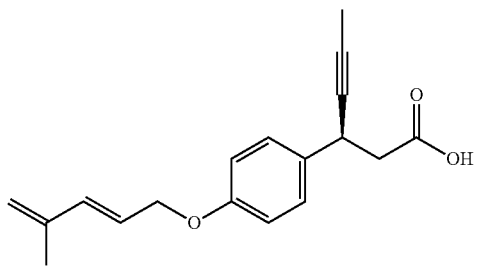

C₁₈H₂₀O₃ = 284.35

The title product was obtained as crystals (1.15 g, 57% yield) under conditions as described in Example F1, using 3S)-3-(4-{[(2E)-4-methylpenta-2,4-dien-1-yl]oxy}-phenyl)hex-4-ynoic acid methyl ester obtained in Example E36 (2.11 g, 7.07 mmol) and other reagents and solvents in suitable proportions. Melting point: 94.7-95.7° C. after recrystallization from n-hexane.

$^1$H NMR (300 MHz, CDCl₃) δ: 7.32-7.26 (m, 2H), 6.95-6.82 (m, 2H), 6.45 (d, J=15.8 Hz, 1H), 5.93-5.76 (m, 1H), 5.02 (s, 2H), 4.57 (d, J=5.8 Hz, 2H), 4.04 (dd, J=5.1, 3.2 Hz, 1H), 2.75 (qd, J=15.7, 7.6 Hz, 2H), 1.87 (s, 3H), 1.83 (d, J=2.4 Hz, 3H).

$^{13}$C NMR (75 MHz, CDCl₃) δ: 177.30, 157.94, 141.34, 136.11, 133.26, 128.48, 124.50, 117.56, 115.00, 79.56, 79.20, 68.80, 43.44, 33.28, 18.60, 3.76.

MS (ESI+): m/z=307.1 [M+Na]⁺. MS (ESI−): m/z=319.1 [M+Cl]⁻.

Example F35: (3S)-3-{4-[(2R/S)-2-methylbutoxy]phenyl}hex-4-ynoic acid

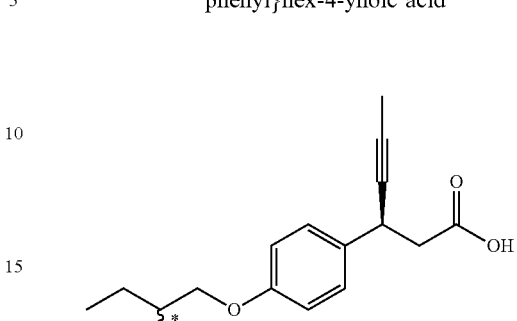

C₁₇H₂₂O₃ = 274.36

(* racemate)

The title product was obtained as an oil (156 mg, 66% yield) under conditions as described in Example F1, using (3S)-3-{4-[(2R/S)-2-methylbutoxy]phenyl}hex-4-ynoic acid methyl ester obtained in Example E13 (250 mg, 0.867 mmol) and other reagents and solvents in suitable proportions.

$^1$H NMR (300 MHz, CDCl₃) δ: 7.31-7.24 (m, 2H), 6.88-6.81 (m, 2H), 4.10-3.99 (m, 1H), 3.75 (ddd, J=26.8, 9.0, 6.3 Hz, 2H), 2.75 (qd, J=15.7, 7.6 Hz, 2H), 1.92-1.77 (m, 1H), 1.83 (d, J=2.4 Hz, 3H), 1.64-1.48 (m, 1H), 1.33-1.17 (m, 1H), 1.00 (d, J=6.7 Hz, 3H), 0.94 (t, J=7.5 Hz, 3H).

$^{13}$C NMR (75 MHz, CDCl₃) δ: 177.13, 158.56, 132.80, 128.40, 114.76, 79.63, 79.10, 73.05, 43.43, 34.85, 33.28, 26.28, 16.68, 11.45, 3.80.

MS (ESI+): m/z=297.1 [M+Na]⁺, 313.1 [M+K]⁺, 571.3 [2M+Na]⁺. MS (ESI−): m/z=273.1 [M−H]⁻, 309.1 [M+Cl]⁻, 547.3 [2M−H]⁻.

Example F36: (3S)-3-{4-[(2S)-2-methylbutoxy]phenyl}hex-4-ynoic acid

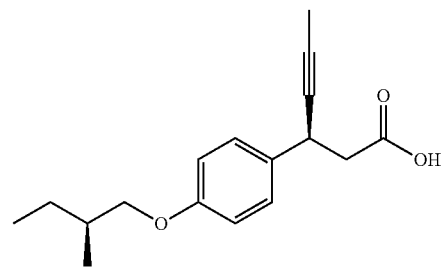

C₁₇H₂₂O₃ = 274.36

The title product was obtained as an oil (93 mg, 75% yield) under conditions as described in Example F1, using (3S)-3-{4-[(2S)-2-methylbutoxy]phenyl}hex-4-ynoic acid methyl ester obtained in Example E14 (130 mg, 0.451 mmol) and other reagents and solvents in suitable proportions. Spectral analysis data identical to those for Example F35.

Example F37: (3S)-3-{4-[(2R/S)-2,3-dimethylbutoxy]phenyl}hex-4-ynoic acid

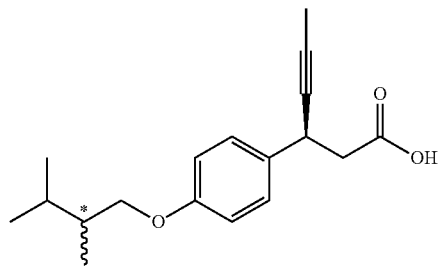

C₁₈H₂₄O₃ = 288.38

(* racemate)

The title product was obtained as an oil (923 mg, 81% yield) under conditions as described in Example F1, using (3S)-3-{4-[(2R/S)-2,3-dimethylbutoxy]phenyl}hex-4-ynoic acid methyl ester obtained in Example E31 (1200 mg, 3.97 mmol) and other reagents and solvents in suitable proportions.

$^1$H NMR (300 MHz, CDCl₃) δ 7.31-7.25 (m, 2H), 6.88-6.81 (m, 2H), 4.04 (ddq, J=8.9, 4.7, 2.3 Hz, 1H), 3.92-3.83 (m, 1H), 3.78-3.68 (m, 1H), 2.75 (qd, J=15.7, 7.6 Hz, 2H), 1.83 (d, J=2.4 Hz, 3H), 1.88-1.73 (m, 2H), 0.95 (dd, J=6.6, 2.0 Hz, 6H), 0.88 (d, J=6.6 Hz, 3H).

$^{13}$C NMR (75 MHz, CDCl₃) δ 177.19, 158.57, 132.83, 128.40, 114.79, 79.65, 79.10, 71.72, 43.44, 38.80, 33.30, 29.44, 20.63, 18.38, 13.22, 3.79.

MS (ESI+): m/z=311.1 [M+Na]⁺. MS (ESI−): m/z=323.1 [M+Cl]⁻

Example F38: (3S)-3-(4-{[(3R/S)-3-methylpentyl]oxy}phenyl)hex-4-ynoic acid

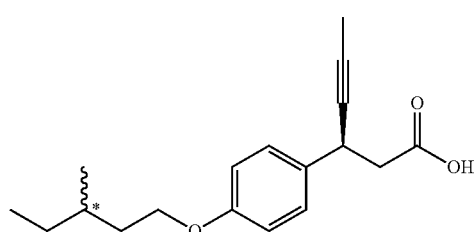

C₁₈H₂₄O₃ = 288.38

(* racemate)

The title product was obtained as an oil (228 mg, 80% yield) under conditions as described in Example F1, using (3S)-3-(4-{[(3R/S)-3-methylpentyl]oxy}phenyl)hex-4-ynoic acid methyl ester obtained in Example E28 (300 mg, 0.992 mmol) and other reagents and solvents in suitable proportions.

$^{13}$C NMR (75 MHz, CDCl₃) δ: 176.84, 158.37, 132.87, 128.41, 114.74, 79.64, 79.10, 66.50, 43.41, 35.96, 33.29, 31.54, 29.65, 19.27, 11.40, 3.80.

MS (ESI+): m/z=311.1 [M+Na]⁺. MS (ESI−): m/z=323.1 [M+Cl]⁻

Example F39: (3S)-3-[4-(4,4,4-trifluorobutoxy)phenyl]hex-4-ynoic acid

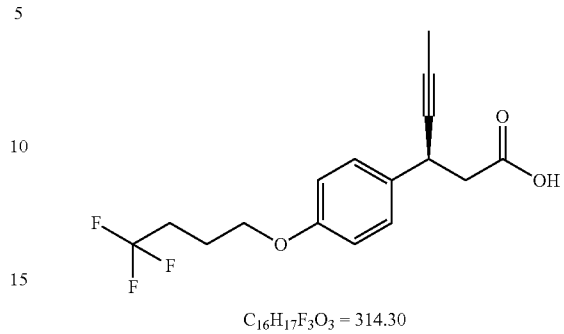

C₁₆H₁₇F₃O₃ = 314.30

The title product was obtained as a solid (203 mg, 71% yield) under conditions as described in Example F1, using (3S)-3-[4-(4,4,4-trifluorobutoxy)phenyl]hex-4-ynoic acid methyl ester obtained in Example E10 (300 mg, 0.914 mmol) and other reagents and solvents in suitable proportions.

MS (ESI+): m/z=337.1 [M+Na]⁺. MS (ESI−): m/z=349.1 [M+Cl]⁻.

Example F40: (3S)-3-{4[(5,5,5-trifluoropentyl)oxy]phenyl}hex-4-ynoic acid

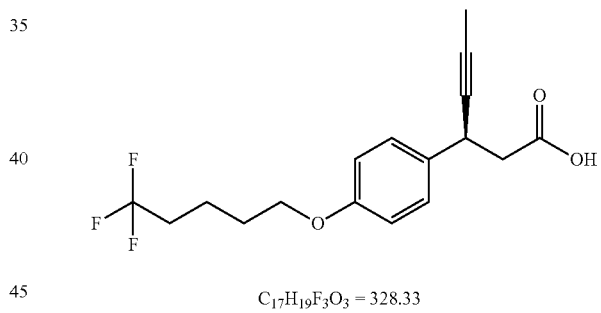

C₁₇H₁₉F₃O₃ = 328.33

The title product was obtained as amorphous solid (380 mg, 88% yield) under conditions as described in Example F1, using (3S)-3-{4-[(5,5,5-trifluoropentyl)oxy]phenyl}hex-4-ynoic acid methyl ester obtained in Example E11 (450 mg, 1.314 mmol) and other reagents and solvents in suitable proportions.

$^1$H NMR (300 MHz, CDCl₃) δ: 7.29 (d, J=8.6 Hz, 2H), 6.84 (d, J=8.7 Hz, 2H), 4.11-4.00 (m, 1H), 3.96 (t, J=5.8 Hz, 2H), 2.75 (qd, J=15.7, 7.6 Hz, 2H), 2.26-2.06 (m, 2H), 1.83 (d, J=2.3 Hz, 3H), 1.93-1.67 (m, 4H).

$^{19}$F NMR (282 MHz, CDCl₃) δ: −66.36 (t, J=10.9 Hz).

$^{13}$C NMR (75 MHz, CDCl₃) δ: 177.10, 158.06, 133.24, 128.51, 127.24 (q, $J_{C-F}$=274.5 Hz), 114.70, 79.54, 79.20, 67.30, 43.40, 33.46 (q, $J_{C-F}$=27.5 Hz), 33.27, 28.45, 19.05 (q, $J_{C-F}$=3.1 Hz), 3.79.

MS (ESI+): m/z=351.1 [M+Na]⁺, 367.1 [M+K]⁺. MS (ESI−): m/z=327.1 [M−H]⁻, 363.1 [M+Cl]⁻, 655.2 [2M−H]⁻.

Example 51: (3S)-3-{4-[(2,3-dimethylbut-2-en-1-yl)oxy]phenyl}hex-4-ynoic acid calcium salt

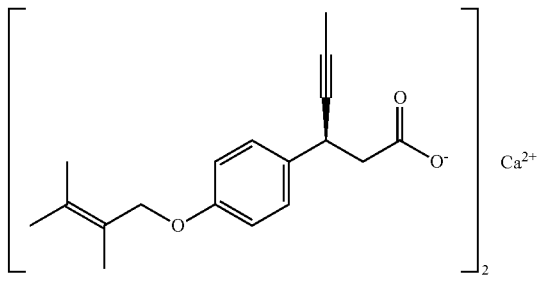

$C_{36}H_{42}CaO_6 = 610.79$ (3S)-3-{4[(2,3-Dimethylbut-2-en-1-yl)oxy]phenyl}hex-4-ynoic acid, obtained in Example F33 as an oil under normal conditions (3.52 g, 12.3 mmol), was dissolved in water (49 ml) at room temperature with stirring and adding lithium hydroxide monohydrate (0.54 g, 12.9 mmol). The solution of lithium salt thus formed was cooled to 15° C. and cold (0° C.) calcium chloride solution (0.72 g, 6.51 mmol) in 14 ml of water was added while vigorously stirring. Precipitated solid was filtered-off, washed with ice-cold water and dried under reduced pressure. A colorless solid was obtained quantitatively (3.179 g) melting with decomposition in the range of 220-240° C.

Example S2: (3S)-3-{4-[(2,3-dimethylbut-2-en-1-yl)oxy]phenyl}hex-4-ynoic acid tert-butylammonium salt

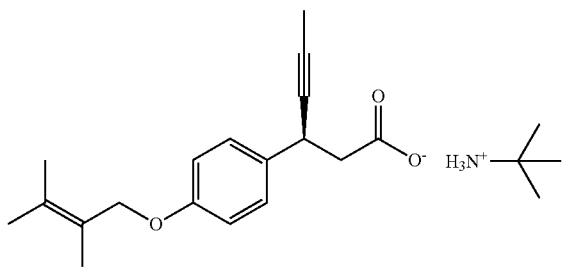

$C_{22}H_{33}NO_3 = 359.50$ (3S)-3-{4[(2,3-Dimethylbut-2-en-1-yl)oxy]phenyl}hex-4-ynoic acid, obtained in Example F33 as an oil under normal conditions (300 mg, 1.05 mmol), was dissolved in toluene (5 ml) and tert-butylamine (0.111 ml, 1.05 mmol) solution in 5 ml of acetone was added at room temperature while stirring. Obtained solid was left for full shaping (seasoning) for 18 hours, and then filtered-off on a glass frit, washed with a toluene-acetone 1:1 mixture and n-pentane, and dried under reduced pressure. The title salt was obtained as colorless crystals (321 mg 85% yield) having melting point in the range of 151.6-152.9° C. (with decomposition).

Example S3: (3S)-3-{4-[(2,3-dimethylbut-2-en-1-yl)oxy]phenyl}hex-4-ynoic acid, salt with (1R,2S)-1-amino-2-indanol

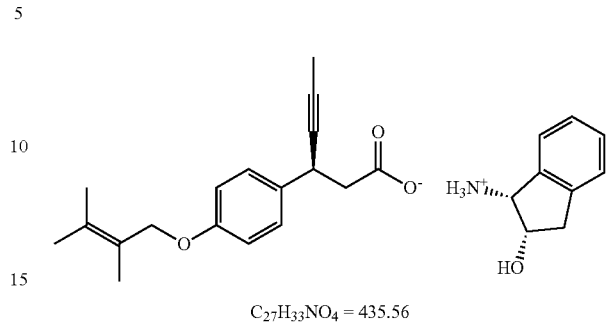

$C_{27}H_{33}NO_4 = 435.56$ (3S)-3-{4[(2,3-Dimethylbut-2-en-1-yl)oxy]phenyl}hex-4-ynoic acid, obtained in Example F33 as an oil under normal conditions (300 mg, 1.05 mmol), was dissolved in acetonitrile (10 ml) and warm solution of (1R,2S)-1-amino-2-indanol (150 mg, 0.985 mmol) in 5 ml of acetonitrile was added while stirring. After 5 minutes of stirring, as the reaction mixture reached room temperature, a solid was formed that was filtered-off on a glass frit, washed with cold acetonitrile and n-pentane, and dried under reduced pressure. The title salt was obtained as colorless crystals (252 mg 55% yield) having melting point in the range of 137.8-139.1° C. (with decomposition).

Biological Activity of the Compounds

Experiment B1: Analysis of Receptor Activation—Calcium Ions Concentration Measurement.

Activation of GPR40 receptor was performed on commercially available CHO-K1 cell line overexpressing human GPR40 receptor and luminescent protein aequorin (Perkin Elmer), the luminescence of which grows significantly upon calcium ions binding. Cells were collected after passage in the amount of $2 \times 10^6$ and incubated for 3 h in HBSS solution (GIBCO) with the addition of 0.015% BSA and 5 uM of coelenterazine (Promega)—the aequorin prostetic group necessary for bioluminescence reaction. Cells were dispenced (with dispenser) in the amount of $5 \times 10^3$ cells/well to the wells of multi-well plate, placed in the measurement chamber of luminometer, with prepared solutions of 2× concentrated tested compounds in reaction buffer (HBSS) in the concentration range of 0.01-10 uM. As a result of the measurement, luminescence change in the time curve were obtained, the integration of which allowed to calculate the relative amount of calcium ions released to cytosol. Compounds that strongly activate the receptor cause the efflux of high amount of calcium ions to cytosol and high cells luminescence. Curves plotted from obtained results allowed to determine $EC_{50}$ values. The test results for each compound were expressed as a percent of the activation of the experimental system by alfa-linolenic acid (positive control).

Therefore, basing on the determined $EC_{50}$ values, direct comparison of the tested compounds of the invention and reference compounds was possible, such as those exemplary presented in Table 2.

TABLE 2

| Example # | Structure | EC$_{50}$ [nM] |
|---|---|---|
| R1 | TAK-875 (fasiglifam) 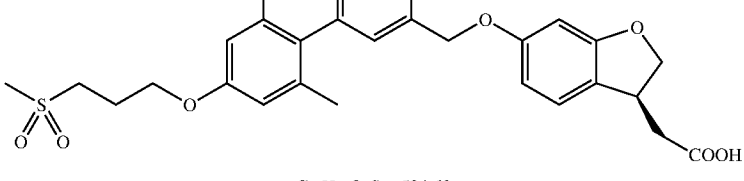 C$_{29}$H$_{32}$O$_7$S = 524.63 | 320 |
| R2 | AMG-837 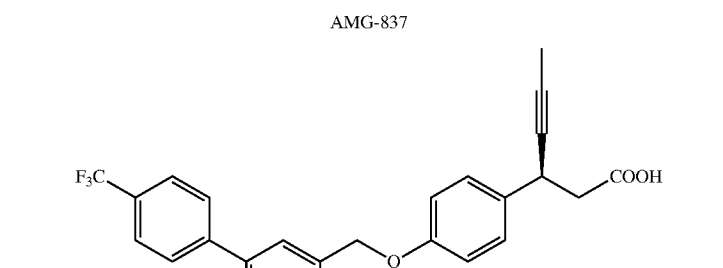 C$_{26}$H$_{21}$F$_3$O$_3$ = 438.44 | 141 |
| S1 | 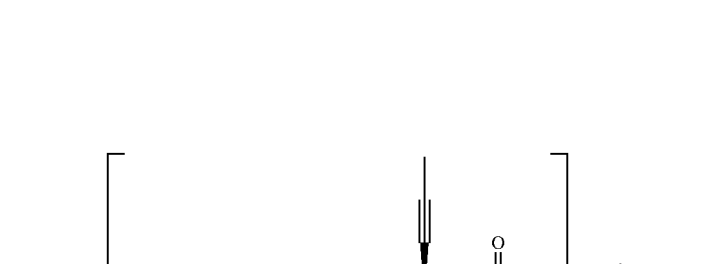 C$_{36}$H$_{42}$CaO$_6$ = 610.79 | 77 |

Due to variable environmental conditions of repeatedly performed Experiment B1 and to avoid continued tabular referring to the reference compounds, the activity of the compounds of the invention was expressed as a % P$_{TAK-875}$ value, in accordance with the following equation:

$$\% \ P_{TAK-875} = \frac{EC50 \ TAK-875}{EC50 \ \text{tested compound}} \times 100\%$$

The above equation gives, expressed in percent, the enhancement or decrease of activity of the compound of the invention in relation to the reference compound TAK-875 (fasiglifam, Compound R1).

Table 3 below presents obtained % P$_{TAK-875}$ values for the compounds of the invention, wherein designations (A), (B), (C), (D), (E) relate to the following ranges of % P$_{TAK-875}$ value:

(A): >120% P$_{TAK-875}$
(B): 81-120% P$_{TAK-875}$
(C): 51-80% P$_{TAK-875}$
(D): 21-50% P$_{TAK-875}$
(E): <20% P$_{TAK-875}$

Table 3 presents also the decrease of the molecular weight (molar weight change, ΔMW) of the compounds of the invention in relation to the reference compound TAK-875 (fasiglifam, Compound R1), expressed in percent.

TABLE 3
| Example # | Structure | % P$_{TAK-875}$ | % ΔMW$_{TAK-875}$ |
|---|---|---|---|
| R1 | TAK-875 (fasiglifam) 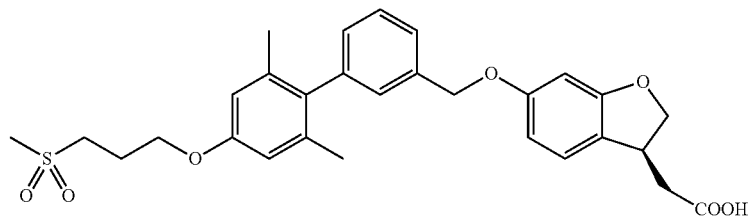 $C_{29}H_{32}O_7S = 524.63$ | B | −0.0% |
| R2 | AMG-837 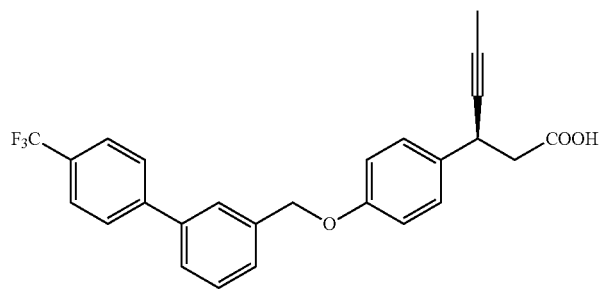 $C_{26}H_{21}F_3O_3 = 438.44$ | A | −16.4% |
| F1 | 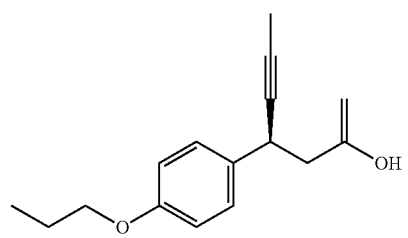 $C_{15}H_{18}O_3 = 246.30$ | D | −53.1% |
| F2 | 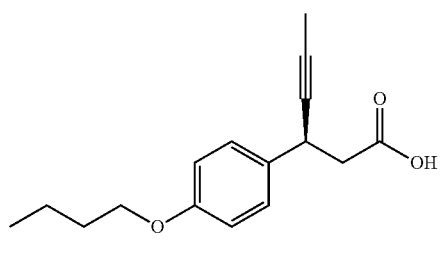 $C_{16}H_{20}O_3 = 260.33$ | A | −50.4% |
| F3 | 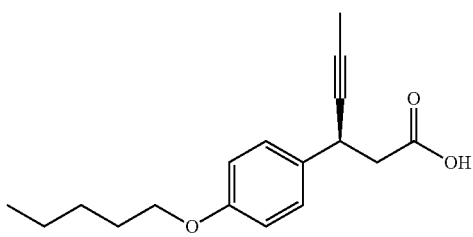 $C_{17}H_{22}O_3 = 274.36$ | A | −47.7% |

TABLE 3-continued
| Example # | Structure | % P$_{TAK-875}$ | % ΔMW$_{TAK-875}$ |
|---|---|---|---|
| F4 | 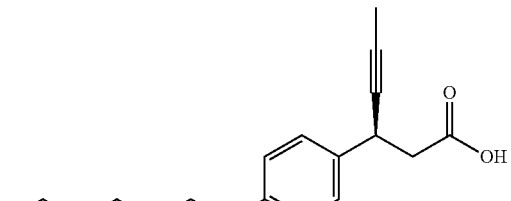 C$_{18}$H$_{24}$O$_3$ = 288.38 | A | −45.0% |
| F5 | 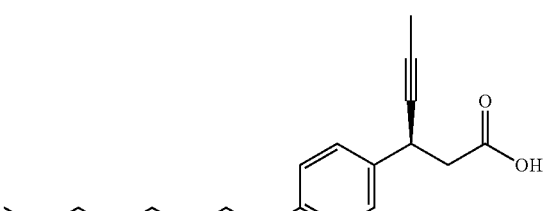 C$_{19}$H$_{26}$O$_3$ = 302.41 | A | −42.4% |
| F6 | 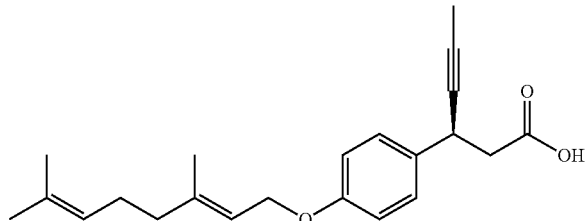 C$_{22}$H$_{28}$O$_3$ = 340.46 | A | −35.1% |
| F7 | 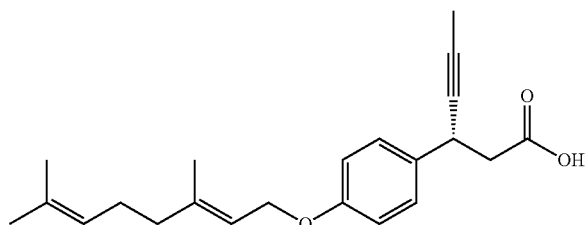 C$_{22}$H$_{28}$O$_3$ = 340.46 | E | −35.1% |
| F8 | 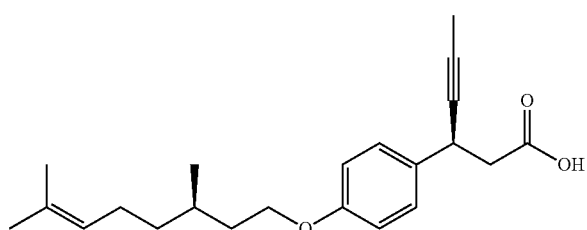 C$_{22}$H$_{30}$O$_3$ = 342.47 | B | −34.7% |

TABLE 3-continued

| Example # | Structure | % P$_{TAK-875}$ | % ΔMW$_{TAK-875}$ |
|---|---|---|---|
| F9 | C$_{22}$H$_{30}$O$_3$ = 342.47 | B | −34.7% |
| F10 | C$_{22}$H$_{28}$O$_3$ = 340.46 | B | −35.1% |
| F11 | (* racemate) C$_{27}$H$_{36}$O$_3$ = 408.57 | D | −22.1% |
| F12 | C$_{16}$H$_{20}$O$_3$ = 260.33 | A | −50.4% |
| F13 | (* racemate) C$_{17}$H$_{22}$O$_3$ = 274.36 | A | −47.7% |

TABLE 3-continued
| Example # | Structure | % P$_{TAK-875}$ | % ΔMW$_{TAK-875}$ |
|---|---|---|---|
| F14 | 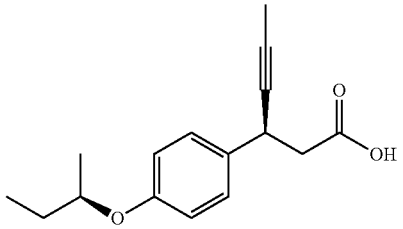 C$_{16}$H$_{20}$O$_3$ = 260.33 | C | −50.4% |
| F15 | 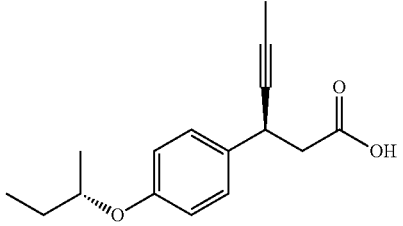 C$_{16}$H$_{20}$O$_3$ = 260.33 | D | −50.4% |
| F16 | 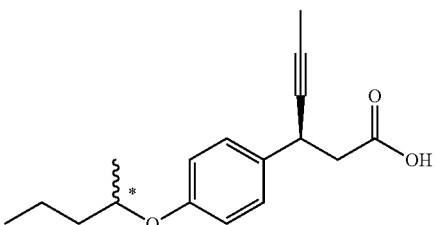 (* racemate) C$_{17}$H$_{22}$O$_3$ = 274.36 | A | −47.7% |
| F17 | 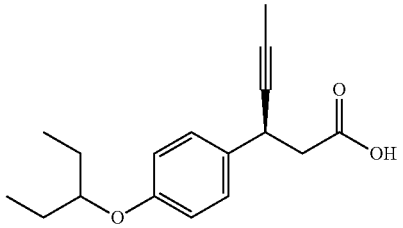 C$_{17}$H$_{22}$O$_3$ = 274.36 | E | −47.7% |
| F18 | 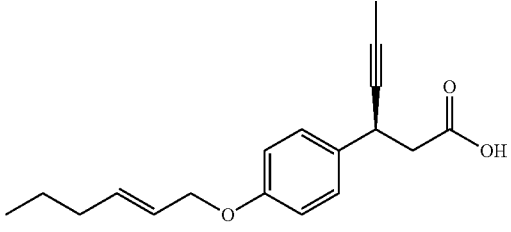 C$_{18}$H$_{22}$O$_3$ = 286.37 | A | −45.4% |

TABLE 3-continued
| Example # | Structure | % P$_{TAK-875}$ | % ΔMW$_{TAK-875}$ |
|---|---|---|---|
| F19 | 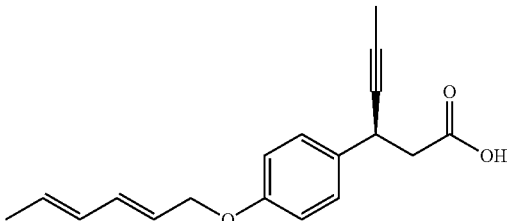 C$_{18}$H$_{20}$O$_3$ = 284.35 | A | −45.8% |
| F20 | 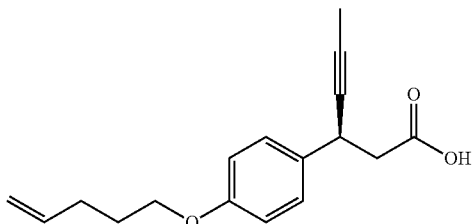 C$_{17}$H$_{20}$O$_3$ = 272.34 | B | −48.1% |
| F21 | 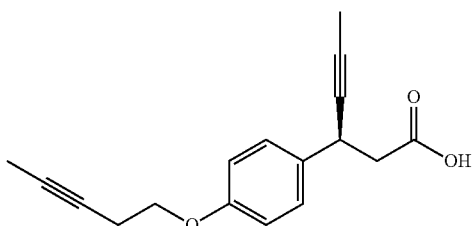 C$_{17}$H$_{18}$O$_3$ = 270.32 | C | −48.5% |
| F22 | 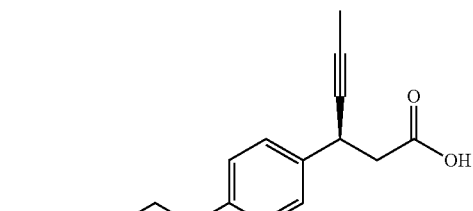 C$_{17}$H$_{18}$O$_3$ = 270.32 | C | −48.5% |
| F23 | 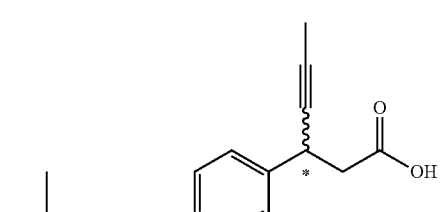 (* racemate) C$_{17}$H$_{22}$O$_3$ = 274.36 | A | −47.7% |

TABLE 3-continued
| Example # | Structure | % P$_{TAK-875}$ | % ΔMW$_{TAK-875}$ |
|---|---|---|---|
| F24 | 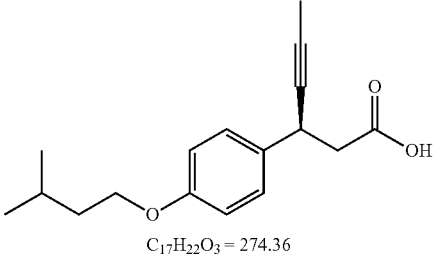 C$_{17}$H$_{22}$O$_3$ = 274.36 | A | −47.7% |
| F25 | 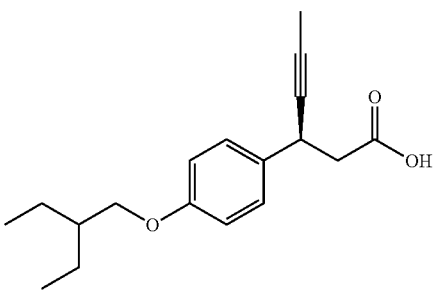 C$_{18}$H$_{24}$O$_3$ = 288.38 | A | −45.0% |
| F26 | 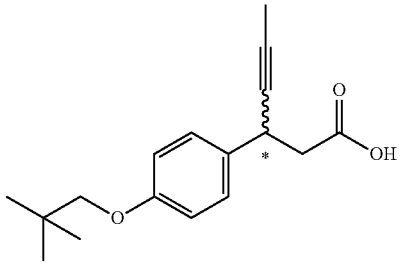 (* racemate) C$_{17}$H$_{22}$O$_3$ = 274.36 | E | −47.7% |
| F27 | 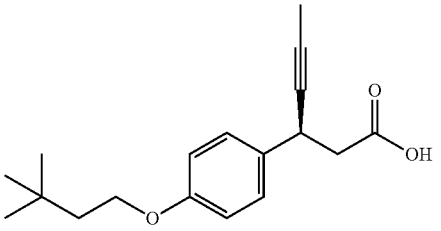 C$_{18}$H$_{24}$O$_3$ = 288.38 | D | −45.0% |
| F28 | 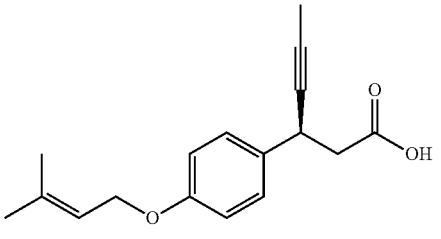 C$_{17}$H$_{20}$O$_3$ = 272.34 | A | −48.1% |

TABLE 3-continued

| Example # | Structure | % P<sub>TAK-875</sub> | % ΔMW<sub>TAK-875</sub> |
| --- | --- | --- | --- |
| F29 | $C_{17}H_{20}O_3 = 272.34$ | E | −48.1% |
| F30 | $C_{17}H_{20}O_3 = 272.34$ | A | −48.1% |
| F31 | $C_{17}H_{19}FO_3 = 290.33$ | B | −44.7% |
| F32 | $C_{17}H_{19}FO_3 = 290.33$ | E | −44.7% |
| F33 | $C_{18}H_{22}O_3 = 286.37$ | A | −45.4% |

TABLE 3-continued

| Example # | Structure | % P$_{TAK-875}$ | % ΔMW$_{TAK-875}$ |
|---|---|---|---|
| F34 | C$_{18}$H$_{20}$O$_3$ = 284.35 | A | −45.8% |
| F35 | (* racemate) C$_{17}$H$_{22}$O$_3$ = 274.36 | A | −47.7% |
| F36 | C$_{17}$H$_{22}$O$_3$ = 274.36 | A | −47.7% |
| F37 | (* racemate) C$_{18}$H$_{24}$O$_3$ = 288.38 | A | −45.0% |
| F38 | (* racemate) C$_{18}$H$_{24}$O$_3$ = 288.38 | B | −45.0% |

TABLE 3-continued

| Example # | Structure | % P<sub>TAK-875</sub> | % ΔMW<sub>TAK-875</sub> |
|---|---|---|---|
| F39 | $C_{16}H_{17}F_3O_3$ = 314.30 | B | −40.1% |
| F40 | $C_{17}H_{19}F_3O_3$ = 328.33 | B | −37.4% |

Experiment B2: Glucose-Dependent Insulin Release in Mouse Insulinoma Cells (MIN6).

MIN6 (mouse insulinoma) cells were seeded on a plate covered with PDL (poly-D-lysine) at 5×10⁵/well and cultured for 48 hours. After 48 hours the cells were washed twice with KRBH buffer (119 mM NaCl, 4.7 mM KCl, 1.2 mM $KH_2PO_4$, 1.16 mM $MgCl_2$, 10 mM HEPES, 2.5 mM $CaCl_2$, 25.5 mM $NaHCO_3$, 0.1% BSA, pH 7.4) and incubated in KRBH buffer with the addition of 2 mM glucose for 2 hours to lower glucose intracellular concentration. Tested compounds, after dilution to the concentration of 10-40 uM in KRBH buffer with the addition of 20 mM glucose, were added to the cells and incubated for 1 hour to induce insulin release. Negative control was KRBH buffer with the addition of 2 mM glucose. Concentration of released insulin was determined using ELISA test (Mercodia). Results of the experiment are presented in Table 4.

Table 4 present MIN6<sub>Insulin</sub> @10 uM values for representative compounds of the invention. MIN6<sub>Insulin</sub> @10 uM value is a multiplicity of insulin efflux increase in relation to control experiment, following addition of 10 uM of tested compound.

TABLE 4

| Example # | Structure | MIN6<sub>Insulin</sub> @10 uM |
|---|---|---|
| R1 | TAK-875 (fasiglifam) 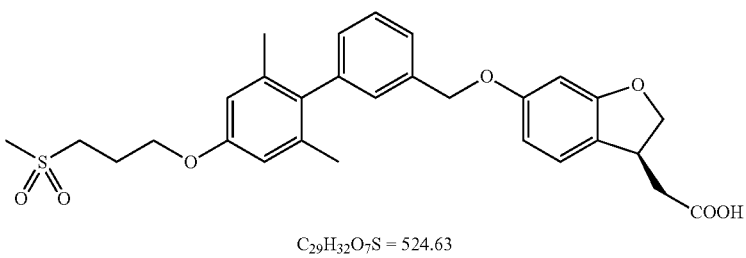 $C_{29}H_{32}O_7S$ = 524.63 | 1.336 |

TABLE 4-continued

| Example # | Structure | MIN6$_{Insulin}$ @10 uM |
|---|---|---|
| R2 | AMG-837 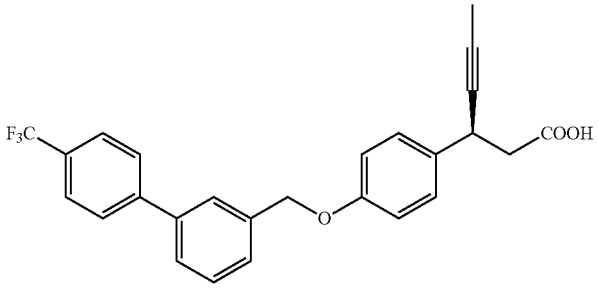 $C_{26}H_{21}F_3O_3$ = 438.44 | 1.567 |
| F24 | 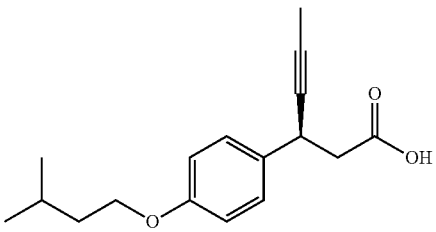 $C_{17}H_{22}O_3$ = 274.36 | 2.627 |
| F28 | 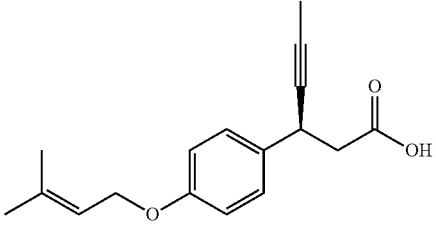 $C_{17}H_{20}O_3$ = 274.34 | 2.782 |
| F33 | 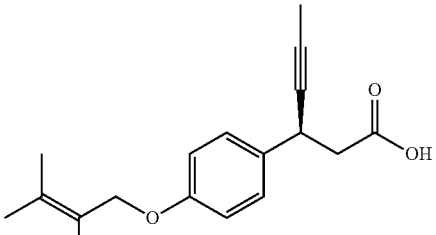 $C_{18}H_{22}O_3$ = 286.37 | 3.895 |

Experiment B3: Glucose Tolerance Test In Vivo on Rats.

To evaluate glucose lowering effect of the compounds in in vivo study, glucose tolerance test (GTT) was performed. The study was performed on male outbred Wistar HAN Crl:WI (HAN) rats from Charles River, weight about 250-300 g, 8-10 weeks old. Rats were starved for 12 hours (with free access to water).

At time point t=0 animals were given orally a single dose of a compound (by a gastric tube) and immediately (t=0) and after 6 hour (t=6 h) intraperitoneal (i.p.) glucose bolus (2 mg/kg). At time points t=0 (just before oral administration of the compounds and intraperitoneal glucose administration), 0.25, 0.5, 1, 2, 2.5, 3, 6, 6.25, 7, 8, and 9 h blood samples from tail vein were collected from each animal for glucose level determination using Accu-chek glucometer (Roche Diagnostics) and additionally at t=0.25, 0.5, 1, 2, 2.5, and 3 h blood samples from tail vein were collected for insulin level measurement using ELISA test (Mercodia).

Tested compound were prepared in 5% DMSO/40% PEG300/55% PBS vehicle and administered at the dose of 10 mg/kg body weight in a volume of 0.5 ml/100 g body weight. After 4 hours after tested compound administration animals were given standard diet to the cages. Decrease of AUC value for glucose level in blood was calculated and the results for selected compounds of the invention are presented in Table 5. Analysis was performed using GraphPad prism software.
TABLE 5
| Example # | Structure | AUC for glucose (0-540 min.) | AUC for insulin (0-180 min.) |
|---|---|---|---|
| — | Vehicle | 44940.4 | 37.8 |
| R1 | TAK-875 (fasiglifam) 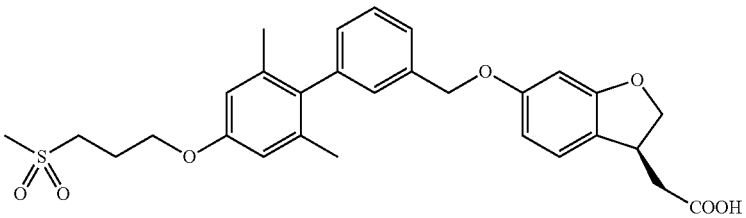 $C_{29}H_{32}O_7S = 524.63$ | 30950.6 | 210.5 |
| F6 | 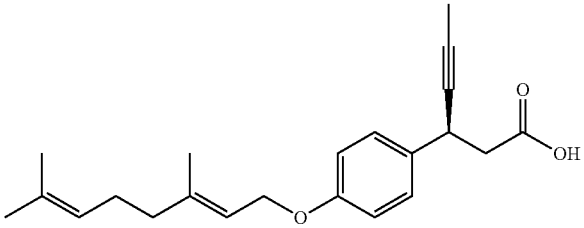 $C_{22}H_{28}O_3 = 340.46$ | 25184.1 | 492.5 |
| F24 | 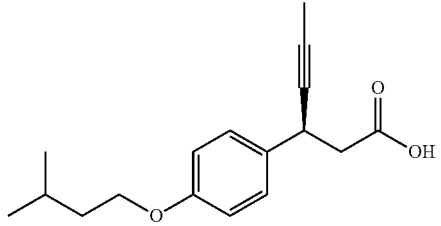 $C_{17}H_{22}O_3 = 274.36$ | 24289.7 | 329.0 |
| F28 | 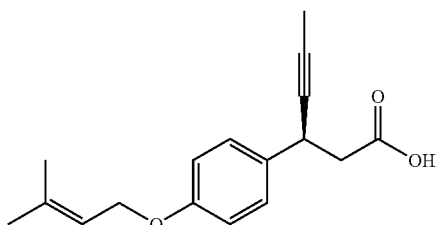 $C_{17}H_{20}O_3 = 272.34$ | 28377.4 | 499.2 |

TABLE 5-continued

| Example # | Structure | AUC for glucose (0-540 min.) | AUC for insulin (0-180 min.) |
|---|---|---|---|
| F33 | 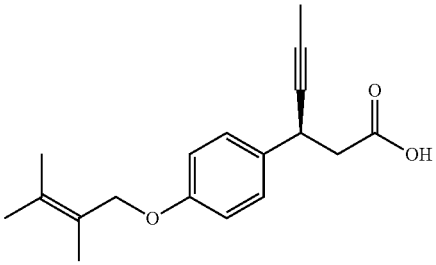 $C_{18}H_{22}O_3$ = 286.37 | 19393.1 | 519.1 |

Experiment B4: Bile Acid Transporters Inhibition in the Liver.

To evaluate the effect of a representative compound on bile acid and bilirubin transporters in the liver, inhibition study at Solvo Biotechnology was performed and the results were compared with the compound TAK-875 known for its hepatotoxic properties, including bile acid transporters inhibition at low concentrations. The compound was tested on a panel of 10 transporters: BSEP, MRP2, MRP3, MRP4 in a vesicular transport inhibition assay and NTCP, OAT1, OAT2v1, OATP1A2, OATP1B1, OATP1B3 in an uptake transporter inhibition assays.

Vesicular transport inhibition assay was performed on membrane vesicles isolated from mammal HEK293 cells overexpressing human ABC transporters. Tested compound were incubated with vesicles and substrates for respective tested transporters. Incubation was performed in the presence of 4 mM ATP or AMP in order to differentiate between uptake by a transporter and passive diffusion into vesicles. In the case of MRP2 and MRP3, reactions were performed in the presence of 2 mM glutathione. Tested compounds were added to the reaction mixture dissolved in 0.75 µl of a solvent (1% of final incubation volume). Reaction mixtures were preincubated for 15 minutes at 37±1° C. Reactions were started by the addition of 25 µl of 12 mM MgATP (or 12 mM AMP) in test buffer, as a background control, separately preincubated. Reactions were quenched by the addition of 200 µl of ice-cold washing buffer and immediate filtration on glass fiber filters mounted on the 96-well filtration plate. Filters were washed (5×200 µl of ice-cold washing buffer), dried and the amount of the substrate inside of filtered vesicles were determined by liquid scintillation counting.

Transporter uptake inhibition test was performed on mammal HEK293 cells overexpressing of a respective transporter. Cells were cultured at 37±1° C. and seeded on 96-well tissue culture plate at 1×10⁵/well. Substrate was removed prior to experiment and cells were washed twice with 100 µl of respective buffer (HK pH 7.4 for OATP1B1 and HBSS pH 7.4 for NTCP, OAT1, OAT2v1, OATP1A2, and OATP1B3). Uptake studies were performed at 37±1° C. in 50 µl of respective buffer containing radioactively tagged substrate and tested compound or solvent.

Concentration of an organic solvent was the same in all wells and did not exceed 1.5% (v/v). After experiment cells were washed twice with 100 µl of ice-cold respective buffer and lysed with 50 µl of 0.1M NaOH. Transport of radioactively tagged substrate was determined by scintillation counter measurement. The results of the experiment are presented in Table 6.

TABLE 6

| Transporter | $IC_{50}$ Example S1: 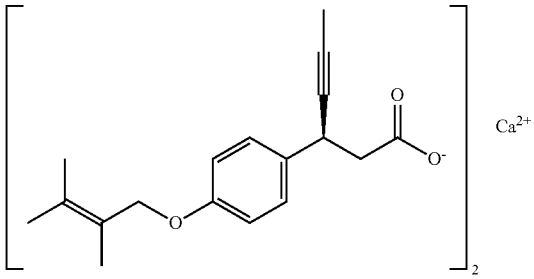 $C_{36}H_{42}CaO_6$ = 610.79 |
|---|---|
| MRP2 | n.d.* |
| MRP3 | n.d.* |
| MRP4 | 131 µM |
| BSEP | >100 µM |
| OAT1 | 245 µM |

TABLE 6-continued

| | |
|---|---|
| OAT2v1 | >300 μM |
| OATP1A2 | 118 μM |
| OATP1B1 | 17.9 μM |
| OATP1B3 | 42.9 μM |
| NTCP | 46.8 μM |

$IC_{50}$
Compound R1:

| Transporter | TAK-875 (fasiglifam) |
|---|---|

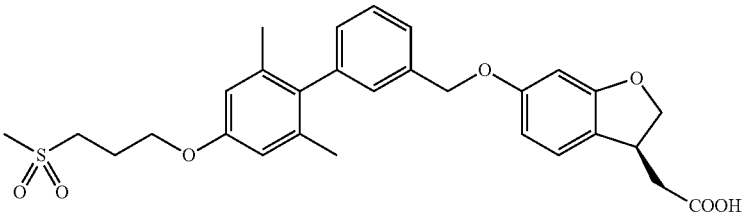

$C_{29}H_{32}O_7S = 524.63$

| | |
|---|---|
| MRP2 | 48.1 μM |
| MRP3 | 31.8 μM |
| MRP4 | 6.9 μM |
| BSEP | 30 μM |
| OAT1 | 34.8 μM |
| OAT2v1 | 62.8 μM |
| OATP1A2 | 10.6 μM |
| OATP1B1 | 0.49 μM |
| OATP1B3 | 3.44 μM |
| NTCP | 53.1 μM |

*n.d. means lack of inhibition of respective receptor up to the tested compound level of 100 μM.

Experiment B5: Von Frey Test on Diabetes STZ-Treated Mice.

von Frey test was used to assess the influence of the compound of Example S1 on tactile allodynia (pain in response when touched) in neuropathic test on diabetes animals (male Albino Swiss mice pretreated with streptozocine to induce the disease). Tactile allodynia was assessed by electronic von Frey apparatus (Bioseb) equipped with a flexible filament. Reaction to stimuli was assessed using growing applied pressure (from 0 to 10 g) on a plantar side of the hind foot of mice. Pregabalin was a control, as reference healthy mice with preserved normal response to the stimuli were used. In the day of the experiment, mice were placed separately in cages with a wire mesh bottom for 1 h for habituation to experimental conditions. After habituation period, each mouse was treated 3 times alternately, with 30 s intervals between each measurement, to obtain starting values (before administration of the compound) of pain sensitivity. Subsequently, mice were treated by oral administration with the compound of Example S1, pregabalin or vehicle and after 60 minutes animals were tested again. The results are presented in Table 7 as mean value for all mice in a given group (n=7-10).

TABLE 7

| | | Applied pressure causing the response [g] | | |
|---|---|---|---|---|
| Compound | Dose p.o. | Sick animal (neuropathic) after compound administration | Sick animal (neuropathic) | Healthy animal |
| Example S1 | 3 mg/kg | 1.85 | 1.67 | 3.36 |
| | 10 mg/kg | 2.34 | | |
| | 30 mg/kg | 3.36 | | |

TABLE 7-continued

| | | Applied pressure causing the response [g] | | |
|---|---|---|---|---|
| Compound | Dose p.o. | Sick animal (neuropathic) after compound administration | Sick animal (neuropathic) | Healthy animal |
| Pregabalin | 3 mg/kg | 2.04 | | |
| | 10 mg/kg | 2.65 | | |
| | 30 mg/kg | 4.11 | | |

The invention claimed is:
1. A compound of formula (I)

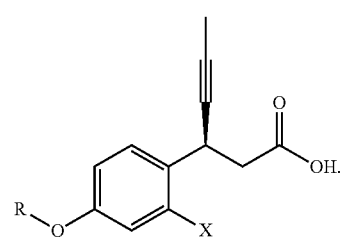

(Ia)

wherein:
R represents:
  a straight or branched, primary or secondary acyclic hydrocarbyl C3-15 group, which can be saturated or unsaturated, or
  a straight or branched, primary or secondary acyclic hydrocarbyl C3-15 group, which can be saturated or unsaturated and wherein one or more hydrogen is replaced with a fluorine;

X represents a hydrogen or a halogen, and
* denotes a chiral center,
or a salt thereof,
with the proviso that formula (I) excludes:
3-(4-([2E,3Z])-2-propylidenepent-3-en-1-yl]oxy)phenyl) hex-4-ynoic acid and (3R/S)-3-[4-(prop-2-yn-1-yloxy) phenyl]hex-4-ynoic acid.

2. The compound according to claim 1, wherein R represents a straight saturated acyclic hydrocarbyl C4-C15 group.

3. The compound according to claim 1, wherein R represents a branched saturated acyclic hydrocarbyl C4-C15 group.

4. The compound according to claim 1, wherein R represents a straight unsaturated acyclic hydrocarbyl C4-C15 group.

5. The compound according to claim 1, wherein R represents a branched unsaturated acyclic hydrocarbyl C4-C15 group.

6. The compound according to claim 4 wherein the unsaturated bonds of the straight unsaturated acyclic hydrocarbyl C4-15 group comprise[s] only double bonds.

7. The compound according to claim 1 wherein R represents a straight or branched, primary or secondary acyclic hydrocarbyl C4-15 group, which can be saturated or unsaturated and wherein one or more hydrogen atoms is replaced with a fluorine atom.

8. The compound according to claim 7 wherein R represents a straight saturated acyclic hydrocarbyl C4-C15 group.

9. The compound according to claim 7 wherein R represents a branched saturated acyclic hydrocarbyl C4-C15 group.

10. The compound according to claim 7 wherein R represents a straight unsaturated acyclic hydrocarbyl C4-C15 group.

11. The compound according to claim 7 wherein R represents a branched unsaturated acyclic hydrocarbyl C4-C15 group.

12. The compound according to claim 10 wherein the unsaturated bonds of the straight unsaturated acyclic hydrocarbyl C4-15 group comprise[s] only double bonds.

13. The compound according to claim 1 wherein X represents a hydrogen.

14. The compound according to claim 1 wherein X represents a halogen.

15. The compound according to claim 1 wherein one, two or three hydrogens at the same carbon atom[s] are replaced with one, two, or three fluorines to form a $CH_2F$, $CHF_2$ or $CF_3$ group, respectively.

16. The compound according to claim 1 in the form of a single enantiomer, single diastereoisomer, or a mixture of enantiomers or diastereoisomers.

17. The compound according to claim 1 in the form of a single enantiomer or diastereoisomer having the structure (Ia)

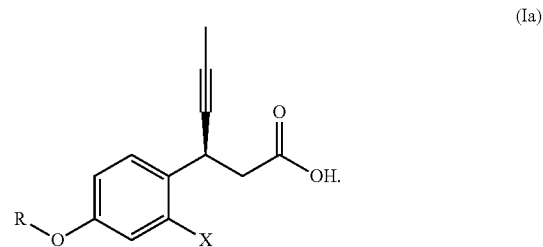

(Ia)

18. The compound according to claim 1 which is (3S)-3-{4-[(2,3-dimethylbut-2-en-1-yl)oxy]phenyl}hex-4-ynoic acid or a pharmaceutically acceptable salt[s] thereof.

19. A pharmaceutical composition comprising the compound of the formula (I) as defined in claim 1 and pharmaceutical excipients.

20. A method of treatment of diseases mediated by GPR40 in a subject in need thereof, said method comprising administering to said subject an effective amount of the compound of the formula (I) as defined in claim 1, and wherein said subject is a mammal.

21. The method of claim 20, wherein the subject is a human.

22. The compound according to claim 14, wherein the halogen is fluorine.

23. A pharmaceutically acceptable salt of the compound of claim 1.

* * * * *